(12) United States Patent
Berlin

(10) Patent No.: US 11,583,444 B2
(45) Date of Patent: Feb. 21, 2023

(54) IMAGE GUIDANCE METHODS AND APPARATUS FOR GLAUCOMA SURGERY

(71) Applicant: Michael S. Berlin, Beverly Hills, CA (US)

(72) Inventor: Michael S. Berlin, Beverly Hills, CA (US)

( * ) Notice: Subject to any disclaimer, the term of this patent is extended or adjusted under 35 U.S.C. 154(b) by 0 days.

(21) Appl. No.: 17/656,956

(22) Filed: Mar. 29, 2022

(65) Prior Publication Data
US 2022/0287881 A1     Sep. 15, 2022

Related U.S. Application Data

(63) Continuation of application No. 17/452,204, filed on Oct. 25, 2021, now Pat. No. 11,318,047, which is a (Continued)

(51) Int. Cl.
*G06K 9/00* (2022.01)
*A61B 18/18* (2006.01)
(Continued)

(52) U.S. Cl.
CPC ...... *A61F 9/00781* (2013.01); *A61B 1/00163* (2013.01); *A61B 34/20* (2016.02);
(Continued)

(58) Field of Classification Search
CPC ........... A61B 17/22; A61B 18/18; G06K 9/00
(Continued)

(56) References Cited

U.S. PATENT DOCUMENTS

| 4,607,622 A * | 8/1986 | Fritch .................... A61B 1/317 606/4 |
| 4,911,148 A | 3/1990 | Sosnowski |

(Continued)

FOREIGN PATENT DOCUMENTS

| FR | 2653657 | 5/1991 |
| GB | 2561860 | 10/2018 |

(Continued)

OTHER PUBLICATIONS

"NanEye / NanEye Stereo, Miniature Camera Module," Datasheet—Public, v2-02, 38 pages (2018).
(Continued)

*Primary Examiner* — Seyed H Azarian
(74) *Attorney, Agent, or Firm* — FisherBroyles, LLP; John K. Shimmick

(57) ABSTRACT

An imaging probe comprises a camera or endoscope with an external detector array, in which the probe is sized and shaped for surgical placement in an eye to image the eye from an interior of the eye during treatment. The imaging probe and a treatment probe can be coupled together with a fastener or contained within a housing. The imaging probe and the treatment probe can be sized and shaped to enter the eye through an incision in the cornea and image one or more of the ciliary body band or the scleral spur. The treatment probe may comprise a treatment optical fiber or a surgical placement device to deliver an implant. A processor coupled to the detector can be configured with instructions to identify a location of one or more of the ciliary body band, the scleral spur, Schwalbe's line, or Schlemm's canal from the image.

13 Claims, 22 Drawing Sheets

Related U.S. Application Data continuation of application No. 17/303,846, filed on Jun. 9, 2021, now Pat. No. 11,191,670, which is a continuation of application No. 17/248,548, filed on Jan. 28, 2021, now Pat. No. 11,071,647, which is a continuation of application No. PCT/US2020/040558, filed on Jul. 1, 2020.

(60) Provisional application No. 62/994,181, filed on Mar. 24, 2020, provisional application No. 62/869,267, filed on Jul. 1, 2019.

(51) Int. Cl.
| | |
|---|---|
| *A61F 9/007* | (2006.01) |
| *A61B 90/00* | (2016.01) |
| *A61F 9/008* | (2006.01) |
| *A61B 34/20* | (2016.01) |
| *G06N 20/00* | (2019.01) |
| *A61F 2/14* | (2006.01) |
| *A61M 27/00* | (2006.01) |
| *G02B 23/24* | (2006.01) |
| *A61B 1/00* | (2006.01) |
| *A61B 34/00* | (2016.01) |
| *A61B 1/04* | (2006.01) |
| *G06T 3/40* | (2006.01) |

(52) U.S. Cl.
CPC ............ *A61B 90/36* (2016.02); *A61B 90/361* (2016.02); *A61B 90/39* (2016.02); *A61F 2/14* (2013.01); *A61F 9/007* (2013.01); *A61F 9/008* (2013.01); *A61M 27/002* (2013.01); *G02B 23/243* (2013.01); *G02B 23/2423* (2013.01); *G06N 20/00* (2019.01); *A61B 1/00096* (2013.01); *A61B 1/00165* (2013.01); *A61B 1/042* (2013.01); *A61B 34/25* (2016.02); *A61B 2034/256* (2016.02); *A61F 2009/00865* (2013.01); *A61F 2009/00868* (2013.01); *G06T 3/4046* (2013.01)

(58) Field of Classification Search
USPC ....... 382/100, 103, 106, 128–133, 156, 162, 382/168, 173, 181, 189, 199, 224, 232, 382/254, 260, 276, 287, 291, 305, 321; 600/4, 478, 114; 606/4, 107
See application file for complete search history.

(56) References Cited

U.S. PATENT DOCUMENTS

| | | | |
|---|---|---|---|
| 5,693,003 | A | 12/1997 | Wolfelschneider |
| 6,296,608 | B1 | 10/2001 | Daniels |
| 6,764,439 | B2 | 7/2004 | Schaaf |
| 8,230,866 | B2 | 7/2012 | Hauger |
| 9,510,973 | B2 | 12/2016 | Wardle |
| 9,579,234 | B2 | 2/2017 | Wardle |
| 9,820,883 | B2 * | 11/2017 | Berlin ..................... A61F 9/008 |
| 9,826,900 | B2 | 11/2017 | Heeren |
| 10,064,757 | B2 | 9/2018 | Berlin |
| 10,188,275 | B2 | 1/2019 | Sonnenschein |
| 10,285,856 | B2 | 5/2019 | Tu |
| 10,363,168 | B2 | 7/2019 | Schieber |
| 10,517,760 | B2 | 12/2019 | Berlin |
| 10,709,547 | B2 | 7/2020 | Schieber |
| 11,185,443 | B2 | 5/2021 | Berlin |
| 11,058,582 | B2 | 7/2021 | Berlin |
| 11,071,647 | B2 | 7/2021 | Berlin |
| 11,185,444 | B1 | 11/2021 | Berlin |
| 11,191,670 | B1 | 11/2021 | Berlin |
| 11,197,779 | B2 | 11/2021 | Van Meter |
| 11,197,780 | B2 | 12/2021 | Haffner |
| 11,318,045 | B2 | 5/2022 | Berlin |
| 11,318,046 | B2 | 5/2022 | Berlin |
| 11,318,047 | B2 | 5/2022 | Berlin |
| 2002/0188285 | A1 | 12/2002 | Brown |
| 2003/0045780 | A1 | 3/2003 | Utsui |
| 2003/0097151 | A1 | 5/2003 | Smedley |
| 2003/0229303 | A1 | 12/2003 | Haffner |
| 2004/0024345 | A1 | 2/2004 | Gharib |
| 2005/0250788 | A1 | 11/2005 | Tu |
| 2006/0041193 | A1 | 2/2006 | Wright |
| 2006/0173397 | A1 | 8/2006 | Tu |
| 2007/0118014 | A1 | 5/2007 | Fuerst |
| 2009/0163898 | A1 | 6/2009 | Gertner |
| 2009/0292170 | A1 | 11/2009 | Boebel |
| 2010/0179652 | A1 * | 7/2010 | Yamamoto ............... A61B 8/10 600/478 |
| 2010/0204609 | A1 * | 8/2010 | Worth .................... A61B 1/313 600/114 |
| 2011/0118611 | A1 | 5/2011 | Luciano |
| 2012/0283557 | A1 | 11/2012 | Berlin |
| 2012/0300032 | A1 | 11/2012 | Ookoba |
| 2014/0275763 | A1 | 9/2014 | King |
| 2014/0288485 | A1 | 9/2014 | Berlin |
| 2014/0336465 | A1 | 11/2014 | Demers |
| 2015/0025320 | A1 | 1/2015 | Rogers |
| 2016/0143778 | A1 | 5/2016 | Aljuri |
| 2017/0042736 | A9 * | 2/2017 | Berlin ................. A61F 9/00802 |
| 2017/0202708 | A1 * | 7/2017 | Berlin ................. A61F 9/00802 |
| 2018/0360310 | A1 | 12/2018 | Berlin |
| 2018/0369017 | A1 | 12/2018 | Schieber |
| 2019/0000561 | A1 | 1/2019 | Decker |
| 2019/0117459 | A1 | 4/2019 | Berlin |
| 2019/0159662 | A1 * | 5/2019 | Papas ................. A61B 1/00032 |
| 2020/0085620 | A1 | 3/2020 | Euteneuer |
| 2020/0179171 | A1 | 6/2020 | Crimaldi |
| 2020/0193600 | A1 * | 6/2020 | Shameli .................... G06T 7/80 |
| 2020/0197221 | A1 | 6/2020 | Schieber |
| 2020/0222238 | A1 | 7/2020 | Schieber |
| 2021/0030590 | A1 | 2/2021 | Blanda |
| 2021/0154449 | A1 | 5/2021 | Haffner |
| 2021/0330499 | A1 | 10/2021 | Wardle |
| 2021/0361479 | A1 | 11/2021 | Wardle |
| 2021/0393110 | A1 | 12/2021 | Ohse |
| 2022/0287879 | A1 | 9/2022 | Berlin |
| 2022/0287880 | A1 | 9/2022 | Berlin |

FOREIGN PATENT DOCUMENTS

| | | |
|---|---|---|
| WO | 2000067687 | 11/2000 |
| WO | 2001089437 | 11/2001 |
| WO | 2005094665 | 10/2005 |
| WO | 2018049246 | 3/2018 |
| WO | 2018232397 | 12/2018 |
| WO | 2020215062 | 10/2020 |
| WO | 2020215064 | 10/2020 |
| WO | 2020215066 | 10/2020 |
| WO | 2020215067 | 10/2020 |
| WO | 2020215068 | 10/2020 |
| WO | 2020215069 | 10/2020 |
| WO | 2020215071 | 10/2020 |
| WO | 2020215073 | 10/2020 |
| WO | 2021003304 | 1/2021 |
| WO | 2021055751 | 3/2021 |

OTHER PUBLICATIONS

As-filed patent application for U.S. Appl. No. 17/656,933, filed Mar. 29, 2022 (103 pages).
As-filed patent application for U.S. Appl. No. 17/656,949, filed Mar. 29, 2022 (103 pages).
Bende, et al., "Fiberoptic Partial Coherence Interferometry (PCI): A Novel Approach to Locate Schlemm's Canal for MIGS Surgery," ARVO 2016 Poster.
Berlin, Michael S., et al., "Chapter 8, Excimer Laser Trabeculostomy (ELT): An Effective MIGS Procedure for Open-Angle Glaucoma," Surgical Innovations in Glaucoma, pp. 85-95 (2014). 2014.
Berlin, Michael S., et al., Chapter 16, "Excimer laser trabeculostomy (ELT): the laser-based MIGS procedure for open-angle glaucoma,"

(56) References Cited

OTHER PUBLICATIONS

New Concepts in Glaucoma Surgery Series: vol. 1, pp. 233-246 (2019).
Catalogue PolyDiagnost, 22 pages (Jul. 2018).
Fibertech, FC304 User Manual (Rev. 1), U88045-E1, 3CMOS HD Camera FC-304, Endoscopic video camera, 49 pages (Oct. 2016).
FiberTech, FL-301 User Manual (Rev. 1) U88046-E1, 3LED Light Source FL-301, Endoscope Light Source (Externally Powered), 32 pages (Oct. 2016).
Fibertech, Solid Fiber Catheter AS-611 Instructions for Use (1st Ed.), Ophthalmic Endoscope, U88033-E, 12 pages, undated but to the best of undersigned attorney's belief and knowledge is believed to be prior to Jul. 1, 2019.
Fisher, Yale L., "A Disposable Ophthalmic Endoscopic System," Arch Ophthalmol, 112:984-986 (Jul. 1994).
Formlabs, "Creating Camera Lenses with Stereolithography," retrieved from https://formlabs.com/blog/creating-camera-lenses-with-stereolithography/, 14 pages (Jan. 5, 2021).
Francis, Brian A., et al., "Endoscopic ophthalmic surgery of the anterior segment," SciVerse ScienceDirect (2013), retrieved Jan. 18, 2022 from http://www.endooptiks.com/assets/francis-survey-endoscopic-ant-seg-surgery-aug-2013.pdf.
Funk, Jens, et al., "Trabecular meshwork ablation shows promise as alternative to invasive glaucoma surgery," retrieved Mar. 17, 2021 from https://www.healio.com/news/ophthalmology/20120225/trabecular-meshwork-ablation-shows-promise-as-alternative-to-invasive-glaucoma-surgery, (Nov. 1, 2004).
Glaukos Corporation iStent inject Trabecular Micro-Bypass System, Directions for Use/Package Insert, P170043C iStent Inject IFU (Jun. 15, 2018).
Glaukos Corporation iStent Trabecular Micro-Bypass Stent, P080030c iStent Inject IFU, 23 pages (undated but believed to be prior to Jan. 28, 2021).
International Search Report and Written Opinion for International Application No. PCT/US2020/040558, 21 pages (dated Nov. 9, 2020).
Ivantis Hydrus Microstent Instructions for Use, P170034D Hydrus IFU, 21 pages (Aug. 2018).
Ivantis Hydrus Microstent Patient Information Brochure, P170034C Hydrus, 10 pages (Aug. 2018).
Berlin, Michael S., et al., "Excimer Laser Trabeculostomy (ELT): An Effective MIGS Procedure for Open-Angle Glaucoma," J.R. Samples, I.I.K. Ahmed (eds.), Surgical Innovations in Glaucoma, Springer Science+Business Media New York, pp. 85-95 (2014).
MLase AG, ExTra Operating Instructions, 703-FB 508237 Manual ExTra EN (Rev02), 37 pages (Apr. 2016).
MLaseAG, Specifications ExTra Laser for Glaucoma Treatment, 1 page (Jul. 13, 2012).
MLaseAG, Specifications FIDO Laser applicator for ExTra Laser System, 1 page (Jul. 13, 2012).
MLaseAG, Specifications FIDO laser applicator for ExTra Laser System, 1 page (Sep. 26, 2013).
Tui Laser AG, "Investigational Testing Authorization Application," 43 pages (Sep. 21, 2004).
TuiLaser AG, Bedienungsanleitung, AIDA, OM-100-GL/Version 2.2, 38 pages, English transation (Aug. 2005).
TuiLaser AG, Bedienungsanleitung, AIDA, OM-100-GL/Version 2.2, 38 pages, German version (Aug. 2005).
Office Action (non-final) for U.S. Appl. No. 17/656,933, 7 pages (dated Jul. 25, 2022).
Office Action (non-final) for U.S. Appl. No. 17/656,949, 9 pages (dated Jul. 18, 2022).
Berlin, Michael S., et al. "Excimer Laser Trabeculostomy: An Effective Microinvasive Glaucoma Surgery Procedure for Open-Angle Glaucoma," 13 sheets (Dec. 19, 2013.
Durr, Georges M., et al., "Current review of Excimer laser Trabeculostomy," Eye and Vision, 7:24, 9 pages (2020).
Hommayda, Sufian, et al., "The AIDA and the extra laser systems for excimer laser trabeculotomy proved comparalbe IOP lowering efficacy—12-month results," Int Ophthalmol 42:1507-1514 (2022).
Jacobi, Philipp C., et al., "Perspectives in trabecular surgery," Eye 14:519-530 (2000).
Loewen, Nils A. and Schuman, Joel S., "There has to be a better way: evolution of internal filtration glaucoma surgeries," Br J Ophthalmol 97(10):1228-1229 (2013).
Response to Non-Final Office Action filed for U.S. Appl. No. 17/656,933, 7 pages, dated Sep. 26, 2022.
Response to Non-Final Office Action filed for U.S. Appl. No. 17/656,949, 4 pages, dated Sep. 26, 2022.
Berlin, Michael S., et al., "Chapter 16, Excimer Laser Trabeculostomy (ELT): An Effective MIGS Procedure for Open-Angle Glaucoma," New Concepts in Glaucoma Surgery Series: vol. 1, pp. 233-246, edited by John R. Samples and Ike Ahmed, Kugler Publications, Amsterdam, The Netherlands (2019).
Toteberg-Harms, M., et al., "Cataract Surgery combined with excimer laser trabeculotomy to lower intraocular pressure: effectiveness dependent on preoperative IOP," BMC Ophthalmology 13:24, 9 pages, http://www.biomedcentral.com/1471-2415/13/24 (2013).
Notice of Allowance for U.S. Appl. No. 17/656,933, 8 pages (dated Nov. 7, 2022).
Notice of Allowance for U.S. Appl. No. 17/656,949, 7 pages (dated Oct. 14, 2022).

* cited by examiner

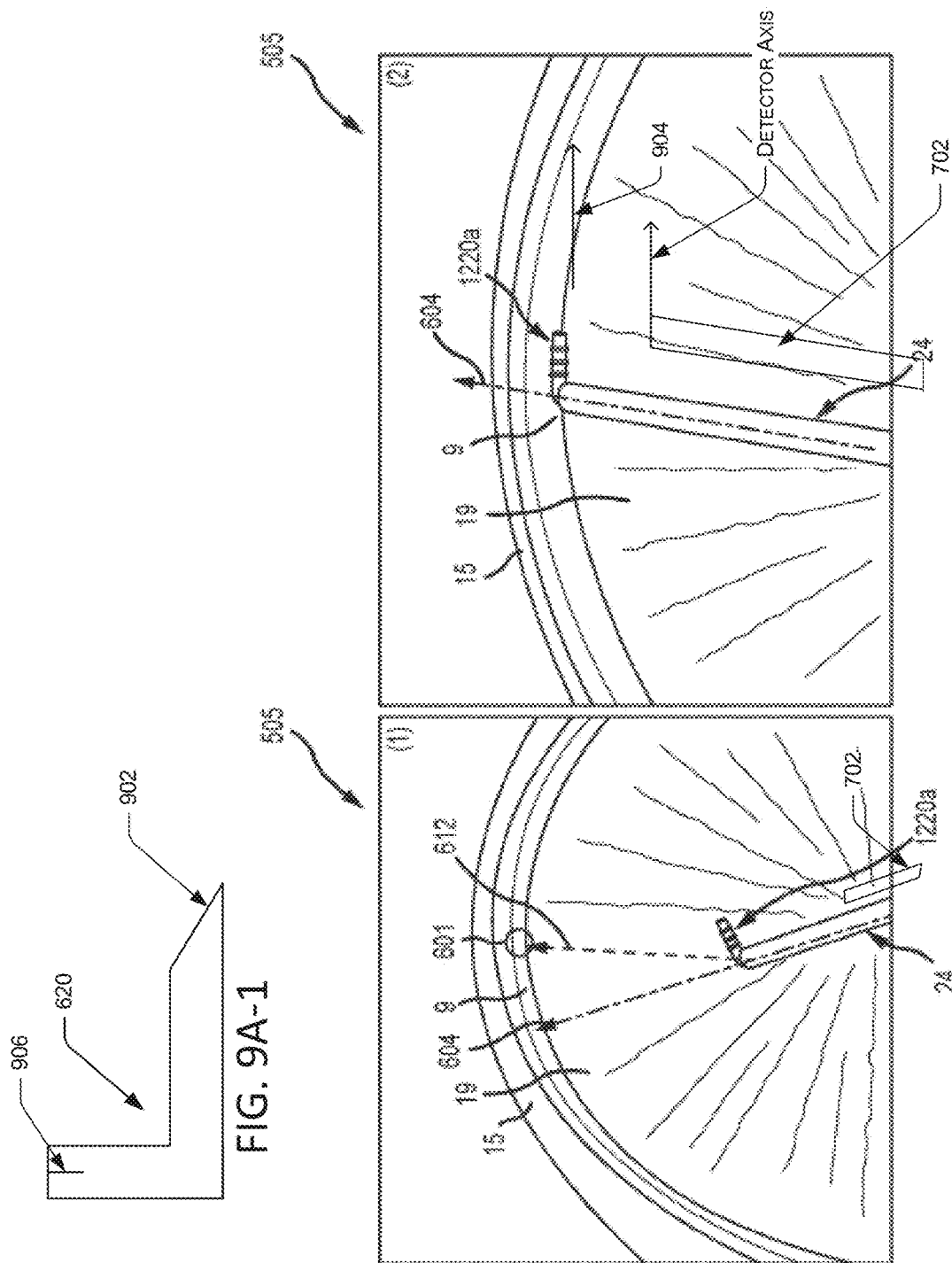

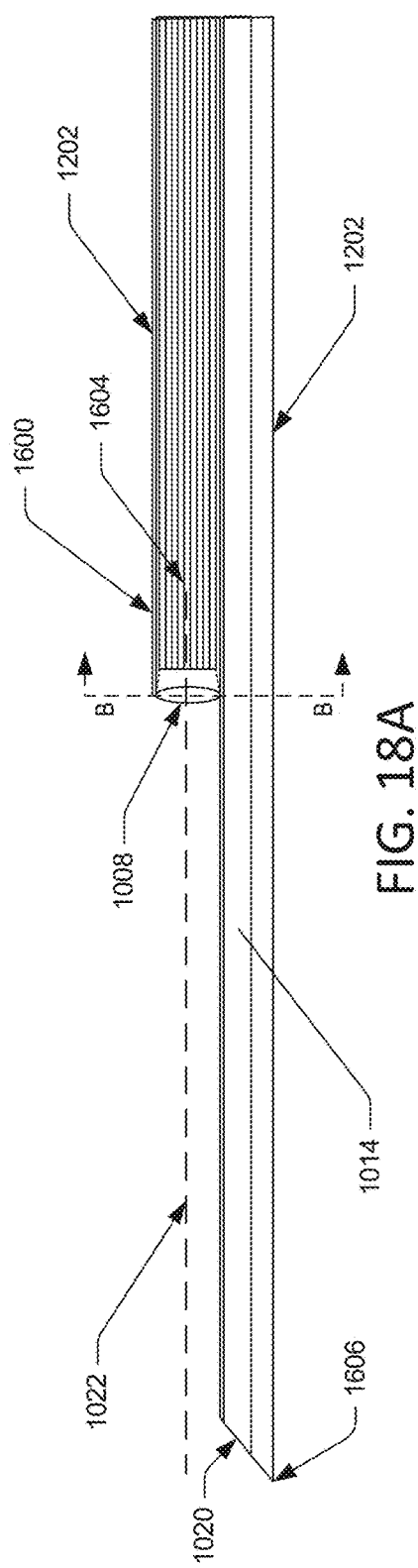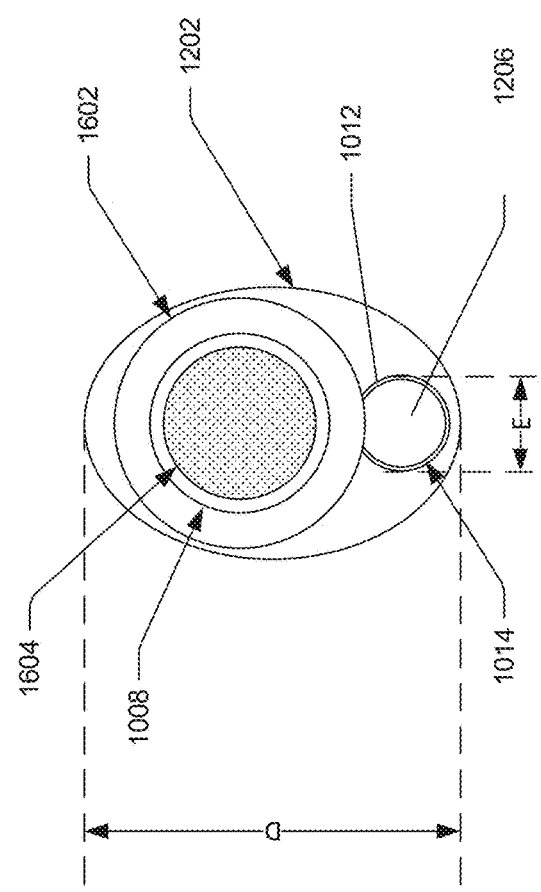

IMAGE GUIDANCE METHODS AND APPARATUS FOR GLAUCOMA SURGERY

RELATED APPLICATIONS

This application is a continuation of U.S. patent application Ser. No. 17/452,204, filed Oct. 25, 2021, now U.S. Pat. No. 11,318,047, issued May 3, 2022, which is a continuation of U.S. patent application Ser. No. 17/303,846, filed Jun. 9, 2021, now U.S. Pat. No. 11,191,670, issued Dec. 7, 2021, which is continuation of U.S. patent application Ser. No. 17/248,548, filed Jan. 28, 2021, now U.S. Pat. No. 11,071,647, issued Jul. 27, 2021, which is a bypass continuation of International Patent Application No. PCT/US2020/040558, filed Jul. 1, 2020, which claims the benefit under 35 U.S.C. § 119(e) of U.S. Provisional Patent Application No. 62/994,181, filed Mar. 24, 2020, and U.S. Provisional Patent Application No. 62/869,267, filed Jul. 1, 2019, the entire disclosures of which are incorporated herein by reference.

The subject matter of the present application is also related to International Application No. PCT/US2018/038072, filed Jun. 18, 2018, published as WO 2018/232397, the entire disclosure of which is incorporated herein by reference.

BACKGROUND

The prior methods and apparatus for treating diseases such as diseases of the eye can be less than ideal in at least some respects. One example of a disease that can be difficult to treat is glaucoma. Although some treatments can be successful, the prior approaches to treating glaucoma can be less than ideal in a least some respects. One approach to treat glaucoma is with minimally invasive glaucoma surgery ("MIGS"). With canal based MIGS, a small opening is formed in the trabecular meshwork to allow fluid to drain into Schlemm's canal. These openings can be formed in many ways, for example with implants or lasers. One approach has been to use excimer laser trabeculostomy ("ELT), in which an ultraviolet laser such as an excimer laser is used to ablate an opening in the trabecular meshwork into Schlemm's canal. Another approach has been to place an implant that extends through the trabecular meshwork into Schlemm's canal. One potentially challenging aspect of canal based MIGS procedures is alignment of a surgical instrument with Schlemm's canal, which can be approximately 200 micrometers ("µm") to 400 µm. In some instances, Schlemm's canal may not be readily visible, and the surgeon may try to estimate the location of Schlemm's canal, which can be challenging and less than ideally accurate in at least some instances. With some implantation procedures, in accurate assessment of the location of Schlemm's canal can lead to the implant not being fully placed in the canal, may lead to tearing of the trabecular meshwork, and in some instances the implant can become dislodged, for example.

With normal ocular pressure, Schlemm's canal is typically not visible from an internal view with a camera. When pressure of the eye is sufficiently low, blood can enter Schlemm's canal and improve visualization of Schlemm's canal. However, once the trabecular meshwork has been penetrated, blood from Schlemm's canal can enter the anterior chamber of the eye, making visualization of the trabecular meshwork more difficult than would be ideal.

In light of the above, it would be beneficial to have improved methods and apparatus to assist the surgeon in identifying the location of Schlemm's canal to facilitate the formation of openings in Schlemm's canal and the placement of implants.

SUMMARY

In some embodiments, a probe comprises a treatment probe comprising a treatment element and an imaging probe to image the treatment element and the anatomic structures targeted for treatment and adjacent structures from an interior of the eye. In some embodiments, the treatment element comprises one or more of an optical fiber or an implant. In some embodiments, a probe comprises a camera sized and shaped for surgical placement in an eye and a treatment probe. In some embodiments, an elongate imaging probe comprises the camera, which comprises one or more lenses and a detector sized for placement in the eye. Alternatively, or in combination, the imaging probe may comprise one or more lenses and one or more optical fibers such as an array of optical fibers or a scanning optical fiber arranged to transmit an image. In some embodiments, the treatment probe and the imaging probe are coupled to each other, such as with a fastener, so as to fix a rotational angle between an elongate axis of the imaging probe and the treatment probe. In some embodiments, the camera and the treatment probe are enclosed together in a housing. The camera and treatment probe are sized and shaped to enter the eye through an incision in the cornea and image one or more of the ciliary body band, the scleral spur, the trabecular meshwork, the juxtacanalicular trabecular meshwork, Schlemm's Canal, the inner wall of Schlemm's Canal, compression of the trabecular meshwork, sites of collector channel orifices where visible from within the anterior chamber, iris root, and other intraocular structures. The treatment probe may comprise an optical fiber or a surgical placement device to deliver an implant. A detector of the camera is sized and shaped for placement in the eye and coupled to a processor configured with instructions to identify a location of one or more of the ciliary body band, the scleral spur, Schwalbe's line, or Schlemm's canal from the image.

In some embodiments, an optical fiber coupled to the camera comprises an inclined distal end, and the processor is configured with instructions to determine an orientation of the inclined end in response to the image from the camera. The processor can be configured with instructions to display markers corresponding to locations of one or more of the iris root, the ciliary body band, the scleral spur, Schwalbe's line, or Schlemm's canal and the treatment probe and other anatomic landmarks/structures. The image from the camera and the markers can be provided to the surgeon in many ways. In some embodiments, the image from the camera placed in the eye is shown on a heads-up display of a microscope, such as an operating microscope, which can allow the surgeon to view the eye anteriorly through a microscope and to view the image of the eye from the camera inserted into the eye, while viewing the images through the oculars of the microscope. In some embodiments, a second camera or cameras coupled to a microscope, such as an operating microscope, provides a microscope image of the eye which is shown on a viewing device. The images from the second camera, the camera placed in the eye, and the markers can be shown on the display, for example, sequentially or concurrently and updating with movement of the probe. These approaches can facilitate the surgery, and in some embodiments allows the surgery to be performed without a gonioscope.

INCORPORATION BY REFERENCE

All patents, applications, and publications referred to and identified herein are hereby incorporated by reference in their entirety and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which:

FIG. 9A shows placement of an implant in accordance with some embodiments;

FIG. 9A-1 shows an implant comprising an engagement structure sized and shaped to receive a protrusion of the inserter so as to fix the angle of elongate axis of the implant with the axis of the camera.

FIG. 18A shows an example of a treatment probe and a fiber optic array with an integrated housing in accordance with some embodiments;

FIG. 18B shows a cross-sectional schematic view of an example treatment probe and camera taken along the line B-B of FIG. 18A.

DETAILED DESCRIPTION

Figure 1:
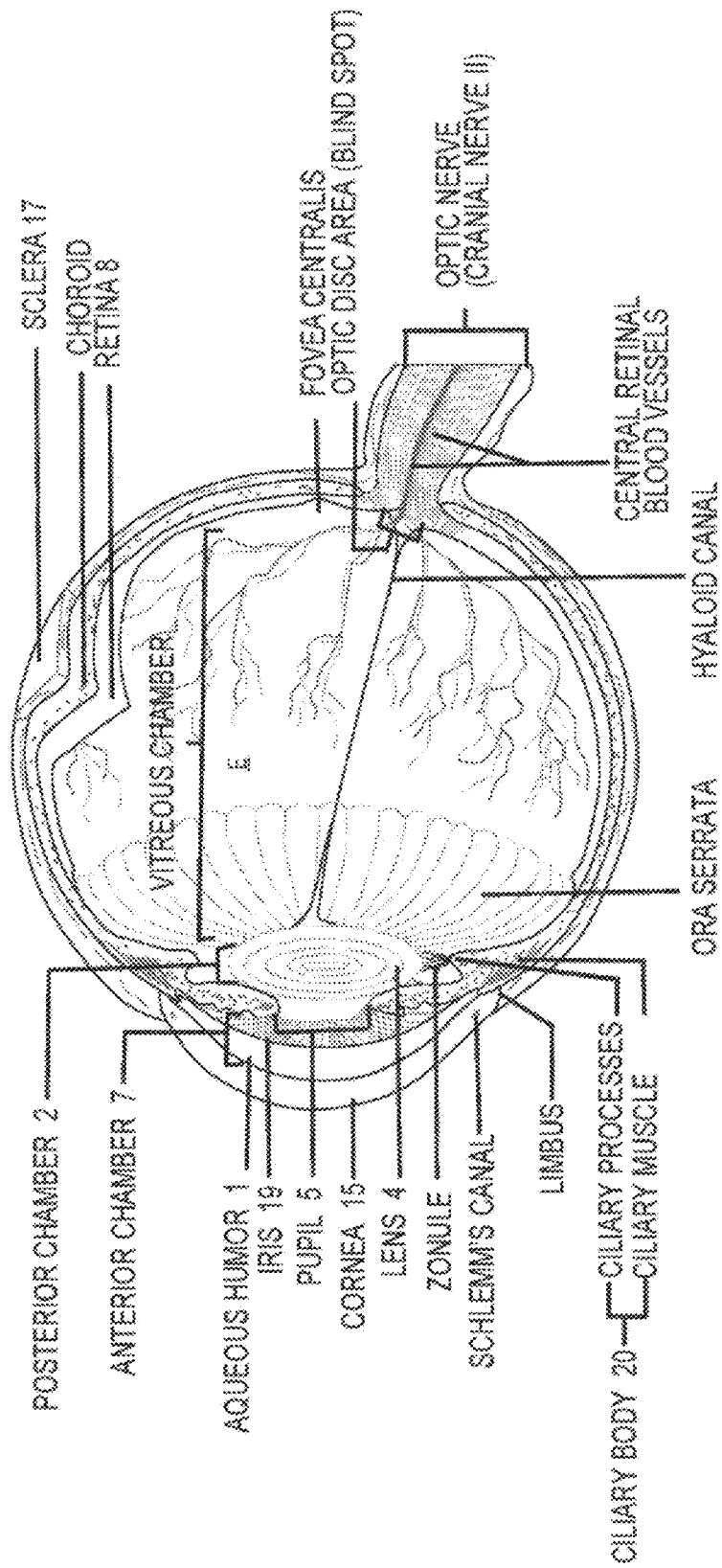
FIG. 1 shows a schematic sectional view of an eye illustrating anatomical structures.

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

Methods and systems disclosed herein can allow more ophthalmic surgeons to successfully perform MIGS procedures. For example, the disclosed methods and apparatus can allow for surgeries to more uniformly and consistently create openings to enable improved outflow of aqueous fluid from the eye's anterior chamber into Schlemm's canal, for example. In addition, the disclosed system and methods can lead to improved surgical outcomes, by allowing surgeons to identify target locations for openings into Schlemm's canal intended to increase outflow. In some cases, a target location may include a surface or layer of a tissue, or a position at a tissue, for example of the trabecular meshwork, the juxtacanalicular trabecular meshwork (JCTM), the inner wall of the Schlemm's canal, the outer wall of the Schlemm's canal, the sclera, or desired combinations thereof.

The presently disclosed methods and apparatus may include the combination of a microscope, such as a surgical microscope, image with sensing devices which enable real-time display images to be concurrently viewed by the surgeon. The real-time display image includes an image which is updated during procedures with minimal latencies. For practical purposes, the real-time augmented display shows images, including video, as events are happening. These augmented images enable the surgeon to view, target and treat locations within an eye which may not be readily visualized using the operating microscope alone, due to their location within the eye at sites in which total internal reflections precludes their visualization in the microscope image, unaided. Such structures include the trabecular meshwork and Schlemm's canal. The methods and apparatus disclosed herein enable a surgeon to view angle structures that are obscured or blocked by total internal reflection. For example, the disclosed methods and apparatus can allow images or information of those otherwise poorly visible or non-visible structures, such as the collector channel system, to be visualized using a camera inserted into the eye, such as by using endoscopic camera technologies. A surgeon can concurrently view a real image of the eye with an overlying projected image of ocular structures by the placement of an image of those structures, such as the collector channel system via, for example, an imaging system placed adjacent the treatment probe, which may be obtained earlier than a surgery, or which may be obtained in real-time during the surgery which may be registered to visible structures or markers, to enable the surgeon to identify and target preferred surgical sites. In this manner, the images viewed by the surgeon include real (optical) and projected (virtual) images combined on a display to enhance surgical visualization and targeting treatment of such tissues.

In some embodiments, the endoscope comprises imaging optics to form an image of the target tissue on an external sensor array, such as a sensor array located on a handpiece of the probe or a sensor array located on a console of a surgical workstation. In embodiments comprising a sensor array located outside the eye, the endoscope may comprise one or more optical fibers, e.g. a plurality of optical fibers, to transmit an image to the sensor array located outside the eye. In some embodiments, an image of the eye is formed on one or more ends of one or more optical fibers located within the eye and the image is transmitted via the one or more optical fibers to the sensor array located outside the eye. Alternatively, the endoscope may comprise a camera comprising the sensor array, in which the camera is inserted into the eye as described herein.

The images from either or both the microscope and the endoscope can be presented to the surgeon in many ways. For example, the images can be superimposed on an image viewed via a monitor or similar viewing devices, such as augmented reality glasses, or goggles or virtual reality glasses or goggles. In some embodiments, a real-time image from a camera inserted into the eye is presented on a binocular heads up display with an optical image of the eye from an microscope, such as an operating microscope, which allows the surgeon to view both the optical image and image from the camera while looking into the microscope. In some embodiments these images are registered to each other with common elements enabling positioning of the intraocular camera system image relative to the microscope image. Additional information can also be provided to the surgeon, such as virtual images of otherwise non-visible structures and one or more symbols to indicate both distances and movement, such as from a probe tip to trabecular meshwork to Schlemm's canal. In some embodiments, an in-situ camera can be used to identify collector channels of the eye, and enable the surgeon to identify sites by these target locations (e.g. by using a graphical visual element such as a treatment reference marker to identify a target location) displayed to the user to assist in the creation of openings at appropriate locations in the trabecular meshwork to increase flow. Some embodiments of the present disclosure encompass any of a variety of in-eye imaging modalities, including pre-operative and/or intra-operative images of the outflow system (e.g. Schlemm's canal and collector channels), which can be overlaid onto a microscope image or view. Further, image analysis algorithms can be applied to recognize anatomical features within the eye during surgery and a heads-up display can augment the real-time imaging with recognized features, guides, locations, markers, and the like to assist the surgeon in completing the surgery. In some cases, one or more images captured by an imaging sensor located within the eye can be used to generate a virtual image of the angle structures.

Such displays can be coupled to the operating microscope in order to present monocular or binocular virtual and/or augmented images from a display which is visually combined with binocular real optical images of the eye, for example. The methods and apparatus disclosed herein are well suited for utilization with ELT surgery and with an implant device such as stent surgeries which provide openings to drain fluid from the eye. However, the provided system and methods can also be applied to various other surgical procedures where fiberoptic-based imaging may be utilized, e.g. any and all surgeries using an endoscope.

In some embodiments, the endoscope comprises a stereoscopic endoscope configured to provide the user with a stereoscopic image of the treatment element from an interior of the eye. The display may comprise a stereoscopic image display to provide the user with a stereoscopic image of the treatment element to facilitate surgeries within the eye.

Although specific reference is made to the treatment of glaucoma using excimer laser trabeculostomy ("ELT"), the methods and systems disclosed herein can be used with many other types of surgeries. For example, the embodiments disclosed herein can be used with other surgical procedures, including endoscopic procedures relating to orthopedic, neurosurgical, neurologic, ear nose and throat (ENT), abdominal, thoracic, cardiovascular, epicardial, endocardial, and other applications to name a few. The presently disclosed methods and apparatus can utilize in-situ imaging to improve targeting accuracy and provide virtual visualization for enabling surgeons to perform procedures in regions that may not be readily visualized either microscopically or endoscopically. Such applications include any endoscopic procedure in which virtual visualization is augmented to real images to assist surgical accuracy in 3-dimensional space, one example of which is an endovascular procedure in which the vessel curves or bends. As used herein, the term "in-situ", as related to imaging, refers to an imaging sensor, such as any number of suitable camera systems, that is positioned at or in close proximity to the treatment site. In some cases, an in-situ imaging system is carried by or with the treatment probe and captures images from the treatment site or along the path to the treatment site to allow the surgeon to see actual anatomical features.

Certain aspects may also be used to treat and modify other organs such as brain, heart, lungs, intestines, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone, as well as body lumens and passages such as the sinuses, ureter, colon, esophagus, lung passages, blood vessels, and throat. For example, the devices disclosed herein may be inserted through an existing body lumen or inserted through an opening created in body tissue.

With reference to FIG. 1, in order to appreciate the described embodiments, a brief overview of the anatomy of the eye E is provided. As schematically shown in FIG. 1, the outer layer of the eye includes a sclera 17. The cornea 15 is a transparent tissue which enables light to enter the eye. An anterior chamber 7 is located between the cornea 15 and an iris 19. The anterior chamber 7 contains a constantly flowing clear fluid called aqueous humor 1. The crystalline lens 4 is supported and moved within the eye by fiber zonules, which are connected to the ciliary body 20. The iris 19 is attached circumferentially to the scleral spur and includes a central pupil 5. The diameter of the pupil 5 controls the amount of light passing through the lens 4 to the retina 8. A posterior chamber 2 is located between the iris 19 and the ciliary body 20.

Figure 2:
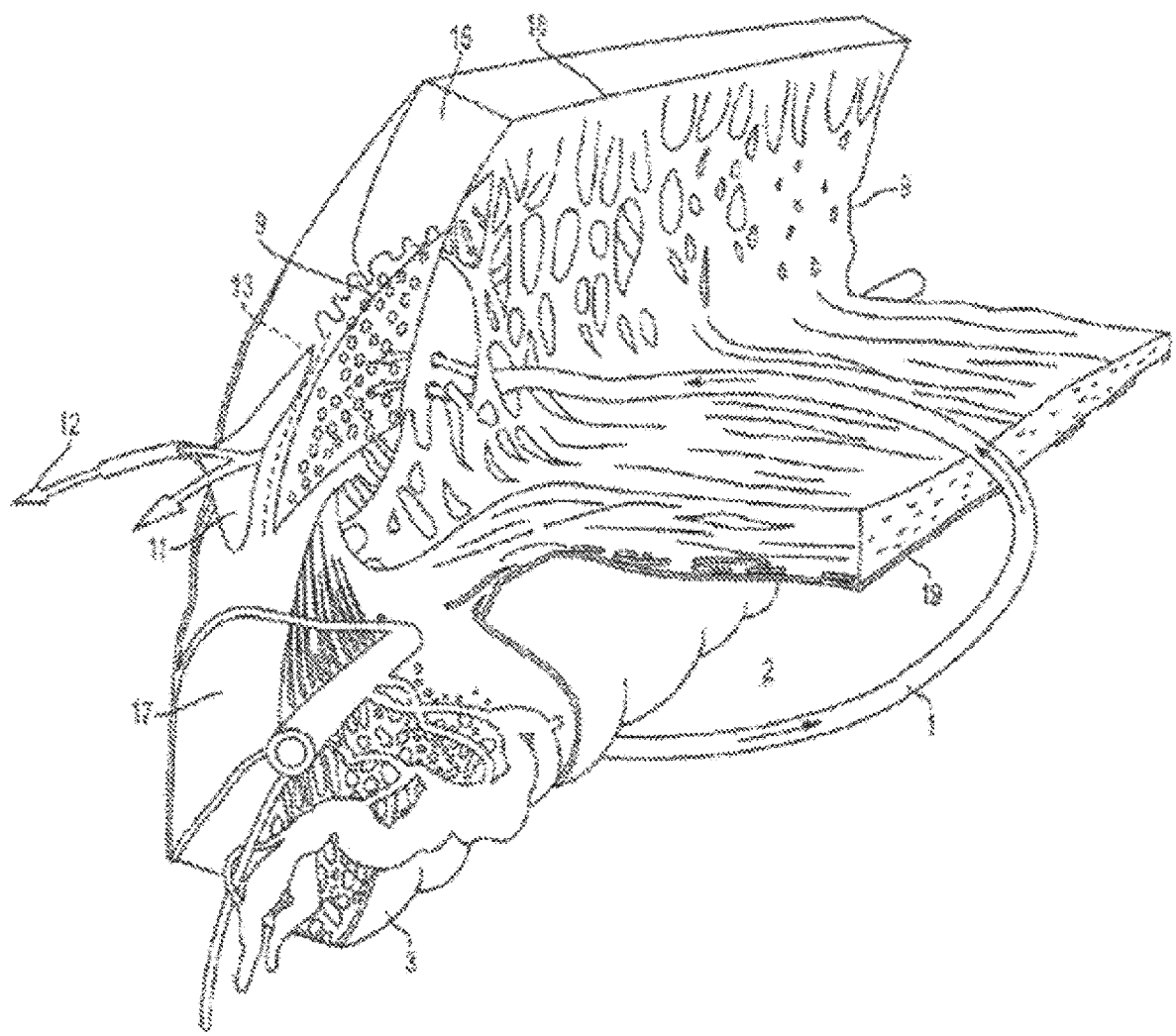
FIG. 2 shows a perspective partial view of the anatomy adjacent to the anterior chamber of an eye.

As shown in FIG. 2 the anatomy of the eye further includes a trabecular meshwork (TM) 9, a triangular band of spongy tissue within the eye that lies anterior to the iris 19 insertion to the scleral spur. The mobile trabecular meshwork varies in shape and is microscopic in size. It is generally triangular in cross-section, varying in thickness from about 100-200 µm. It is made up of different fibrous layers having micron-sized pores forming fluid pathways for the egress of aqueous humor from the anterior chamber. The trabecular meshwork 9 has been measured to about a thickness of about 100 µm at its anterior edge, Schwalbe's line 18, at the approximate juncture of the cornea 15 and sclera 17.

The trabecular meshwork widens to about 200 µm at its base where it and iris 19 attach to the scleral spur. The height of the trabecular meshwork can be about 400 µm. The passageways through the pores in trabecular meshwork 9 lead through a very thin, porous tissue called the juxtacanalicular trabecular meshwork 13, which in turn abuts the interior wall of a vascular structure, Schlemm's canal 11. The height of Schlemm's canal can be about 200 µm, or about half the height of the trabecular meshwork. Schlemm's canal (SC) 11 is filled with a mixture of aqueous humor and blood components and connects to a series of collector channels (CCs) 12 that drain the aqueous humor into the venous system. Because aqueous humor 1 is constantly produced by the ciliary body and flows through the pupil into the anterior chamber from which it passes through pores in the TM and JCTM into the SC and aqueous veins, any obstruction in the trabecular meshwork, the juxtacanalicular trabecular meshwork, or Schlemm's canal, prevents the aqueous humor from readily escaping from the anterior eye chamber. As the eye is essentially a closed globe, this results in an elevation of intraocular pressure within the eye. Increased intraocular pressure can lead to damage of the retina and optic nerve, and thereby cause eventual blindness.

The obstruction of the aqueous humor outflow, which occurs in most open angle glaucoma (i.e., glaucoma characterized by gonioscopically readily visible trabecular meshwork), is typically localized to the region of the juxtacanalicular trabecular meshwork (JCTM) 13, located between the trabecular meshwork 9 and Schlemm's canal 11, and, more specifically, the inner wall of Schlemm's canal.

When an obstruction develops, for example, at the juxtacanalicular trabecular meshwork 13, intraocular pressure gradually increases over time. Therefore, a goal of current glaucoma treatment methods is to prevent optic nerve damage by lowering or delaying the progressive elevation of intraocular pressure.

Figure 3:
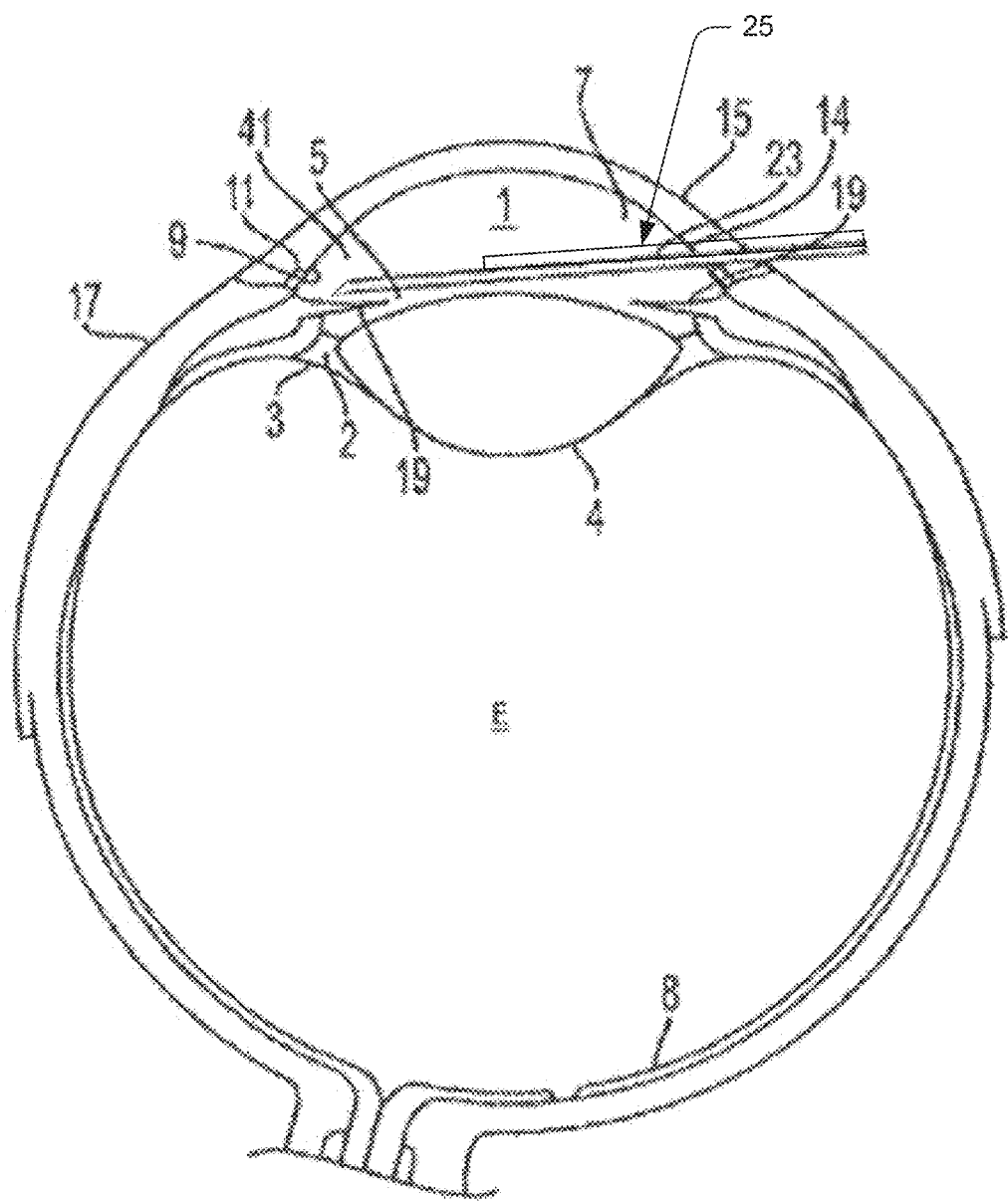
FIG. 3 shows a schematic sectional view of an eye illustrating a fiber optic probe and imaging probe crossing the anterior chamber from a corneal limbal paracentesis site toward the trabecular meshwork in the anterior chamber of the eye in accordance with some embodiments.

With reference to FIG. 3, a side sectional view of the interior anatomy of a human eye E is shown with a treatment probe comprising fiber-optic probe 23, and a camera 25 coupled to the probe inserted into the eye in accordance with some embodiments. A small self-sealing paracentesis incision 14 is created in the cornea 15. The anterior chamber can be stabilized with either a chamber maintainer using liquid flows or a viscoelastic agent. Fiber-optic probe 23 and the camera 25 can then be positioned and advanced through the incision 14 into the anterior chamber 7 until a distal end of the fiber-optic probe 23 contacts and slightly compresses the desired target TM tissues.

Photoablative laser energy produced by laser unit 31 (shown in FIG. 7) is delivered from the distal end of fiber-optic probe 23 in contact to the tissue to be ablated. The tissue to be ablated may include the trabecular meshwork 9, the juxtacanalicular trabecular meshwork 13 and an inner wall of Schlemm's canal 11. An aperture in the proximal inner wall of Schlemm's canal 11 is created in a manner which does not perforate the distal outer wall of Schlemm's canal. In some embodiments, additional apertures are created in the target tissues. Thus, the resultant aperture or apertures are effective to restore relatively normal rates of drainage of aqueous humor. The photoablative laser energy may comprise one or more types of laser energy, such as visible, ultraviolet, near infrared, or infrared laser energy, and combinations thereof. In some embodiments, the laser energy comprises 308 nm laser energy from a Xenon Chloride excimer laser. The laser may comprise pulsed energy or substantially continuous energy, for example. In embodiments, the laser energy delivered from the probe comprises femto-second or pico-second laser energy, for example.

The fiber-optic probe 23 may comprise an optical fiber or a plurality of optical fibers encapsulated by an encapsulating sheath. The diameter of a single optical fiber should be sufficiently large to transmit sufficient light energy to effectively result in photoablation of target tissues. In some embodiments, the optical fiber diameter is in a range from about 4-6 µm. A single optical fiber or a plurality of optical fibers can be used in a bundle of a diameter ranging from about 100 µm to about 1000 µm, for example. The optical fiber core and cladding can be encased within an outer metal sleeve, or shield. In some embodiments the sleeve is fashioned from stainless steel. In some embodiments, the outer diameter of sleeve is less than about 100 µm. In some embodiments, the diameter can be as small as 100 µm, as where smaller optical fibers are implemented with laser delivery systems. In some cases, the optical fiber may have a diameter of about 200 µm and the fiber-optic probe 23 may have a greater diameter such as 500 µm to encapsulate one or more optical fibers. In some embodiments, the sleeve can be flexible so that it can be bent or angled.

Figure 4A:
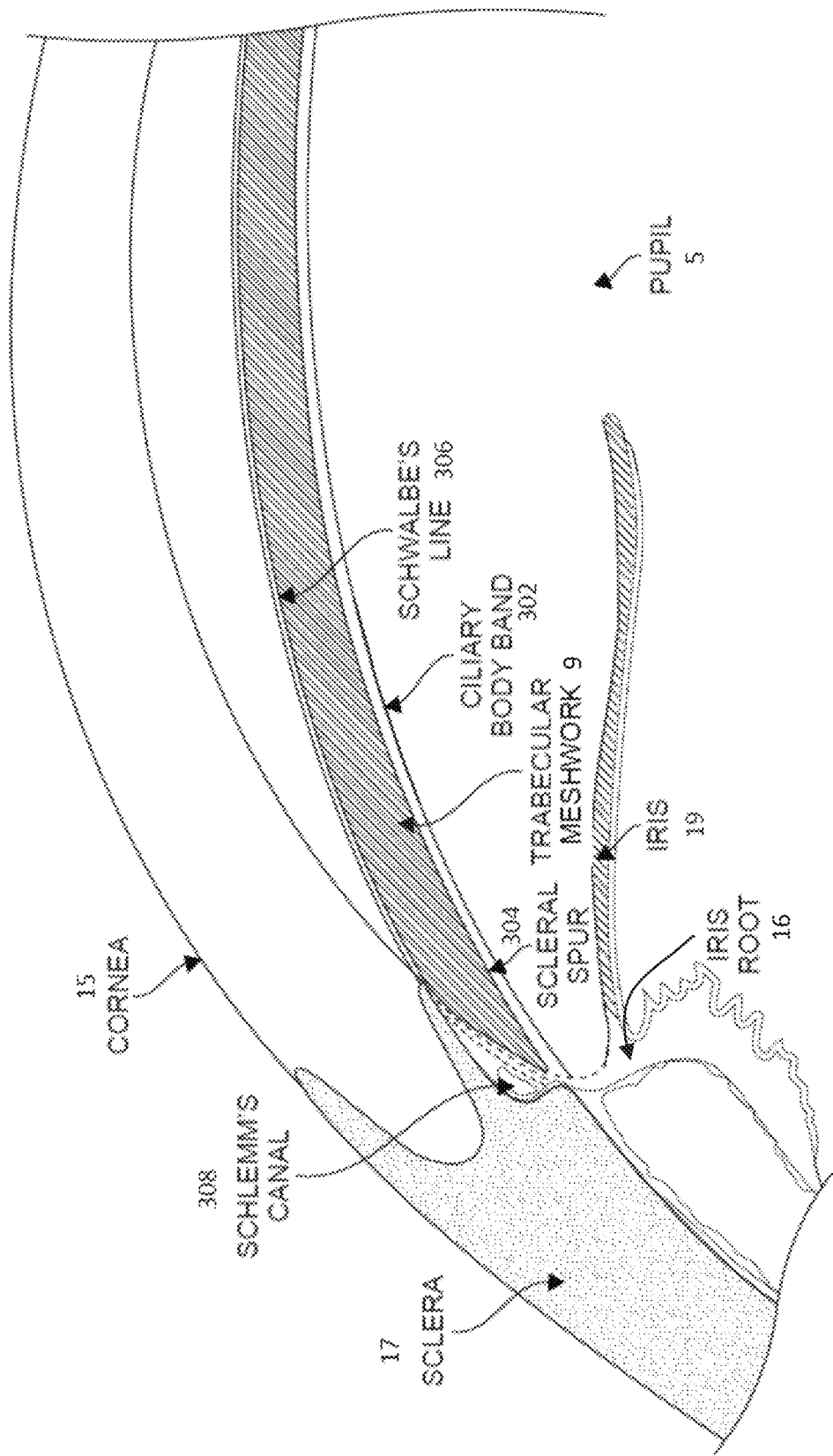
FIG. 4A shows a partial schematic view of the anatomy of the anterior chamber angle of an eye showing Schlemm's canal, the scleral spur and Schwalbe's line.
Figure 4B:
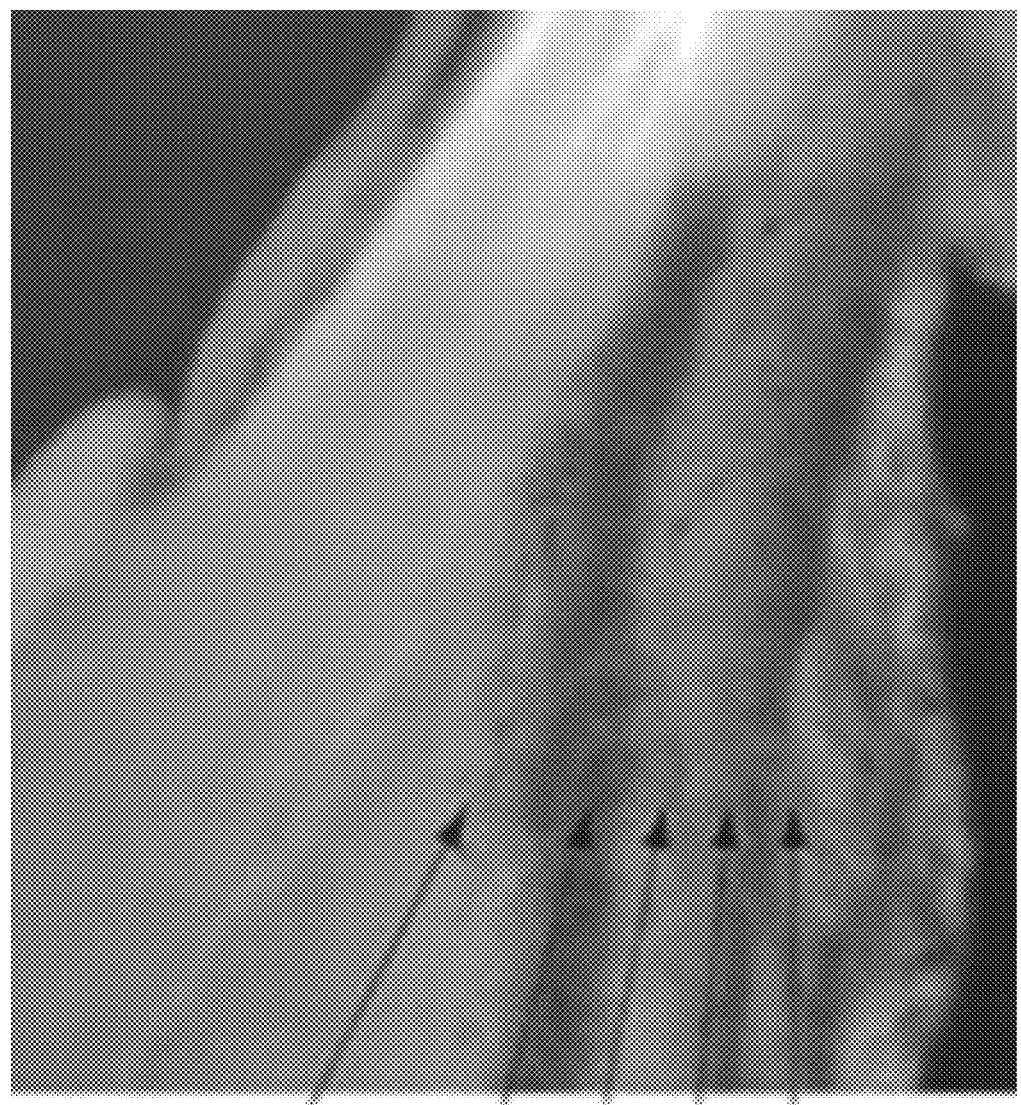
FIG. 4B shows a partial view of the anatomy of an eye and is representative of an image obtained with an endoscope or other imaging system from the viewpoint of within an eye.

FIGS. 4A and 4B show interior structures of the eye visible with an endoscope, such as an endoscope comprising a camera inserted to the eye as described herein. Structures visible with the endoscope inserted into the eye with an ab interno approach as described herein include the ciliary body band 302 and the scleral spur 304. In some embodiments, Schwalbe's line 306 can be viewed with the camera inserted into the eye. In some embodiments, Schlemm's canal 308 can be seen in the camera image, depending on the intraocular pressure of the eye during surgery. In some embodiments, the intraocular pressure of the eye is sufficiently high to limit blood from entering Schlemm's canal 308, and Schlemm's canal may not be readily visible with the endoscope inserted into the eye as described herein, such as by an endoscope comprising a camera inserted into the eye as described herein. Also, in some embodiments, Schwalbe's line 306 may not be readily visible in the image provided by the endoscope inserted into the eye, such as an endoscope comprising a camera inserted into the eye or an external sensor array as described herein. The methods and apparatus disclosed herein can be well suited for identifying or estimated the locations structures of the eye that may not be readily visible from the endoscope inserted into the eye, so as to assist the surgeon with the placement of the treatment probe.

Figure 5A:
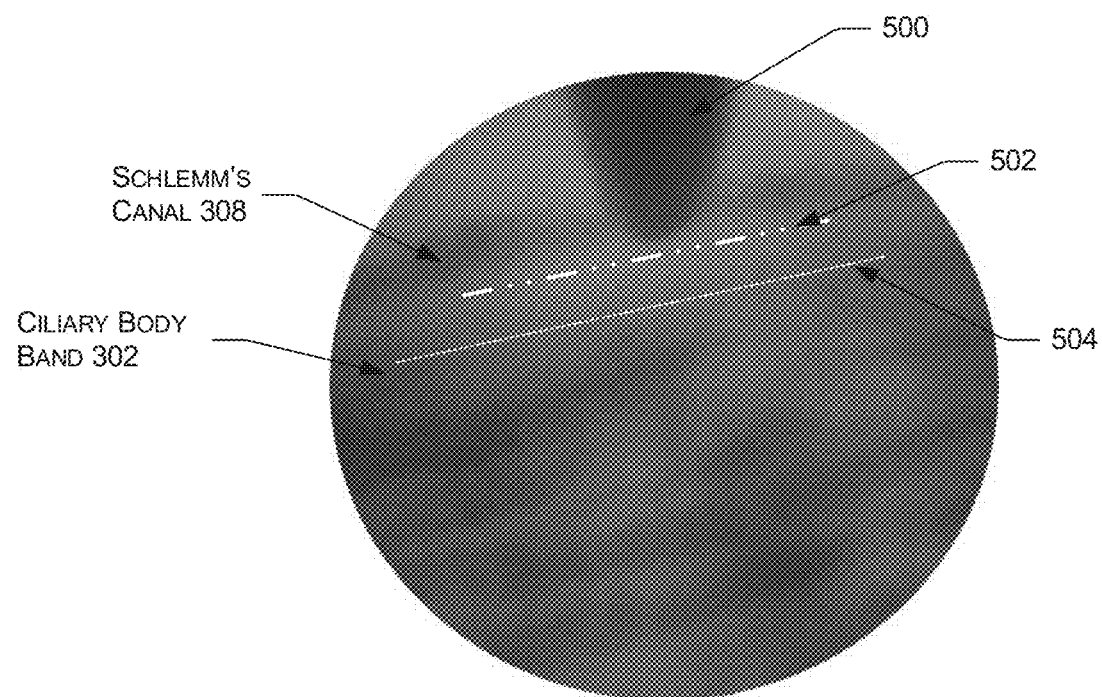
FIG. 5A shows an exemplary image overlaid with markers in accordance with some embodiments with the probe rotated with respect to the target tissue.
Figure 5B:
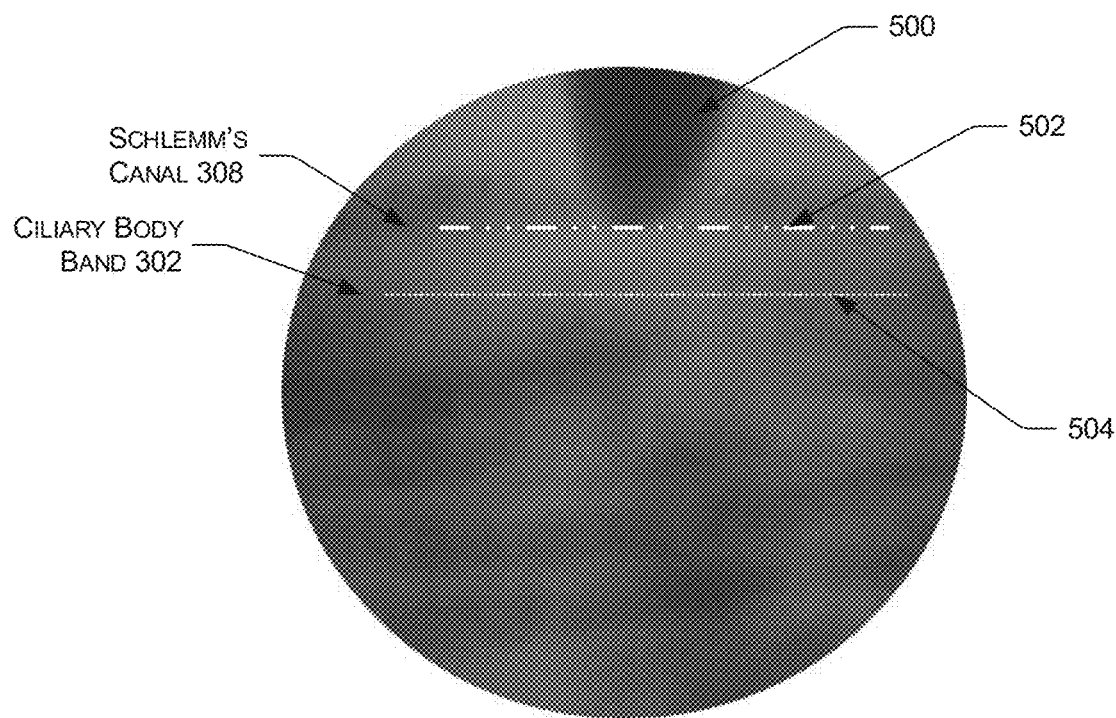
FIG. 5B shows an exemplary image as in FIG. 5A in accordance with some embodiments with the probe rotationally aligned with the target tissue.

FIGS. 5A and 5B show images shown on a heads-up display from an in situ camera with markers presented on a display visible to a surgeon as described herein, in accordance with some embodiments. The processor-identified location of the ciliary body band 302 and the processor-determined location of Schlemm's canal 308 are shown with markers presented on the display visible to the surgeon. For example, a camera as described herein can be advanced with a treatment probe 500 and capture real-time imaging data during a procedure. The real time imaging data can be used by a processor to determine a location of Schlemm's canal 308 in response to one or more of the ciliary body band 302, iris root or the scleral spur 304. The processor can be configured to display an estimated location of Schlemm's canal 308 with indicia such as markers, to assist the surgeon with placement of the probe on the trabecular meshwork adjacent Schlemm's canal, so that the surgeon can accurately place the probe on the trabecular meshwork overlying Schlemm's canal 308. This approach can be helpful when Schlemm's canal 308 is not readily visible in the camera image. Alternatively, or in combination, the processor can be configured to determine the location of Schlemm's canal 308 from the location of Schlemm's canal 308 as shown in the image, for example when Schlemm's canal 308 comprises sufficient contrast to be visible such as may occur with cataract surgery. Although FIG. 5A shows markers on the real time images from the camera inserted into the eye of the patient, in some embodiments the images are shown on the heads up display without markers and the fixed orientation between the camera and the probe allows the surgeon to determine the orientation of the probe in response to the images.

FIG. 5A illustrates a treatment probe 500 shown in the image, which may comprise an optical fiber within a housing. In some embodiments, the camera comprises an axis that is fixed rotationally in relation to an axis of the probe. A camera may be affixed to, carried by, or be disposed within a shared housing with the treatment probe 500, such that the camera captures images of the treatment probe 500 during a procedure. The camera may aid a surgeon in delivering the treatment probe 500 to a target location, such as for performing a procedure, delivering and installing an implantable device, or for surveying areas of interest within a patient. As illustrated, the treatment probe 500 is placed in proximity to Schlemm's canal 308 and the ciliary body band 302. One or more of these anatomical features may be visible through the camera system and are recognizable by a user. According to some embodiments, the camera is coupled to a controlling unit, as will be described in further detail. The controlling unit may comprise a processor and instructions performable by the processor. In some embodiments, the instructions comprise one or more image analysis algorithms that can detect anatomical features and landmarks. In some instances, the controlling unit is able to identify anatomical features and augment the camera view by overlaying information, such as markers, for example a Schlemm's canal identifier 502, a ciliary body band identifier 504, or some other identifier or a combination of identifiers, onto the camera imaging data as described herein. For instance, the controlling unit, by executing one or more feature recognition algorithms, may recognize the Schlemm's canal 308 and place a Schlemm's canal identifier 502. In some cases, the system may recognize Schlemm's canal 308 based upon a difference in contrast in the analyzed image. For example, Schlemm's canal 308 may be identified based upon a difference in contract of greater than 5%. Although Schlemm's canal may comprise a generally annular structure in three-dimensional space, when viewed from within the anterior chamber, Schlemm's canal may resemble a line which may be substantially straight or somewhat curved depending on the field of view and the angle at which the camera approaches the site.

In some embodiments, the controlling unit augments the camera imaging data by placing a Schlemm's canal identifier 502 that closely follows Schlemm's canal 308. The Schlemm's canal identifier 502 can resemble a line and can be updated to remain in an overlaid position with respect to the anatomical feature even as the camera moves. The augmented layer or at least some of the graphical elements of an augmented image can be mapped or matched to the optical image using object recognition techniques or pattern matching techniques, such as feature point recognition, edge detection, classifiers, spatial pyramid pooling, convolutional neural networks, or any of a number of suitable object recognition algorithms, or a combination of techniques. The Schlemm's canal identifier 502 can be placed on the images substantially in real time, for example with a latency of no more than five video frames, for example with a latency within a range from one to four video frames.

Alternatively, or in combination, the controlling unit may recognize and identify other anatomical features, such as the ciliary body band 302, as illustrated. Here, the controlling unit augments the camera image data by overlaying a ciliary body band identifier 504 to follow the general shape of the ciliary body band 302. While the illustrated markers can be substantially straight lines, the markers may take other shapes and may be contoured to follow the anatomical contours at the imaged site. The markers may optionally denote the boundaries of selected anatomical features, such as Schwalbe's line, scleral spur, or Schlemm's canal 308. For example, a plurality of dashed lines can be used to indicate the estimated anterior and posterior boundaries of Schlemm's canal 308 with a central line extending along an estimated central location of Schlemm's canal as shown in the camera image. This approach can be helpful when Schlemm's canal is not readily visible in the image viewed by the surgeon.

Other information, such as distances, arrows, directions, text, or other information may be likewise used to augment the camera imaging data. In some embodiments, the system may use identifiable features to locate other features. For example, the system may identify the scleral spur, and based upon the magnification, average distances and features sizes, the system may be able to identify the approximate location of Schlemm's canal 308 based upon the recognized features, even if the imagery doesn't readily show Schlemm's canal 308. For example, a processor may be configured with instructions to determine a location of Schlemm's canal 308 in response to identifying one or more of the ciliary body band 302 or the scleral spur and to display the location on a subsequent image from the detector array of the camera As shown in FIG. 5A, it is readily apparent that the camera is in a rotated orientation with respect to Schlemm's canal 308. In some procedures, it may be helpful to orient the treatment probe 500 with Schlemm's canal 308. By using the methods and apparatus disclosed herein, a user can quickly determine whether the treatment probe 500 is rotationally aligned with one or more structures of the eye such as one or more of the iris root, the ciliary body band 302, the scleral spur, or Schlemm's canal 308. The markers, such as the Schlemm's canal identifier 502 can provide further useful information for aligning the treatment probe 500 with Schlemm's canal 308, which can be helpful when Schlemm's canal 308 is not readily visible from the image of the camera array inserted into the eye for example.

As shown in FIG. 5B, once a user has rotated the treatment probe 500 and camera, the camera image and associated data shows that Schlemm's canal 308 and the associated Schlemm's canal identifier 502 are substantially horizontal. In some cases, where the Schlemm's canal identifier 502, and as a result, Schlemm's canal 308 itself, is horizontal, then the user is assured that the treatment probe 500 is aligned with Schlemm's canal 308. Of course, other marker information may be used or displayed to augment the camera imaging data and may aid a user in approaching and orienting the treatment probe 500 with respect to any anatomical feature of interest.

Figure 6A:
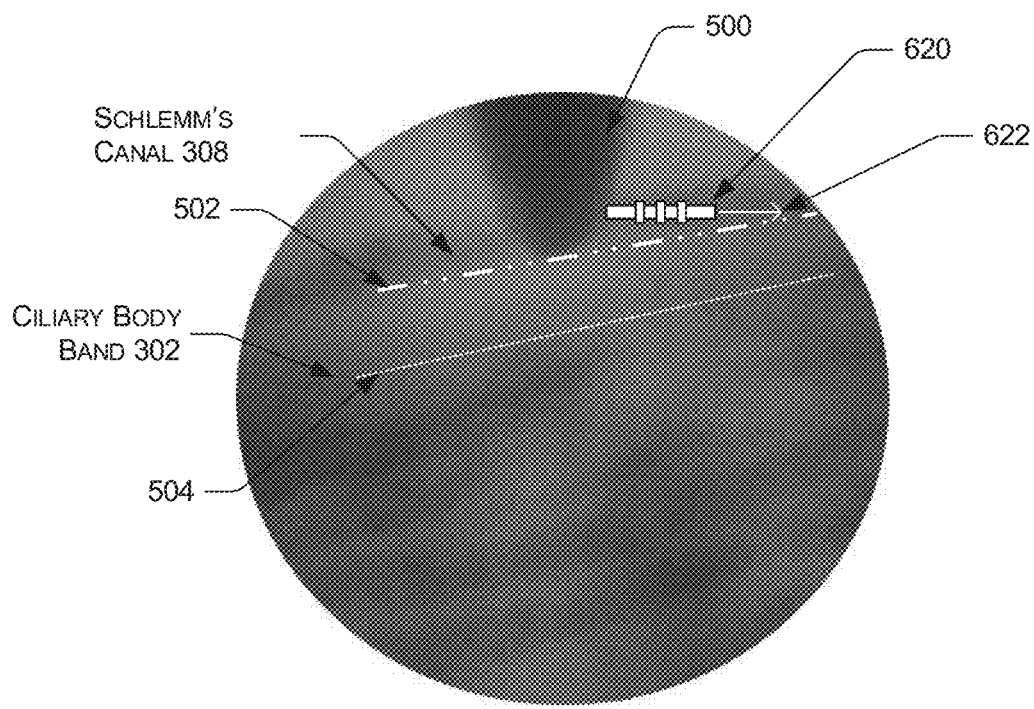
FIG. 6A shows an exemplary image overlaid with treatment markers in accordance with some embodiments with the implantation axis of the implant rotated with respect to Schlemm's canal.
Figure 6B:
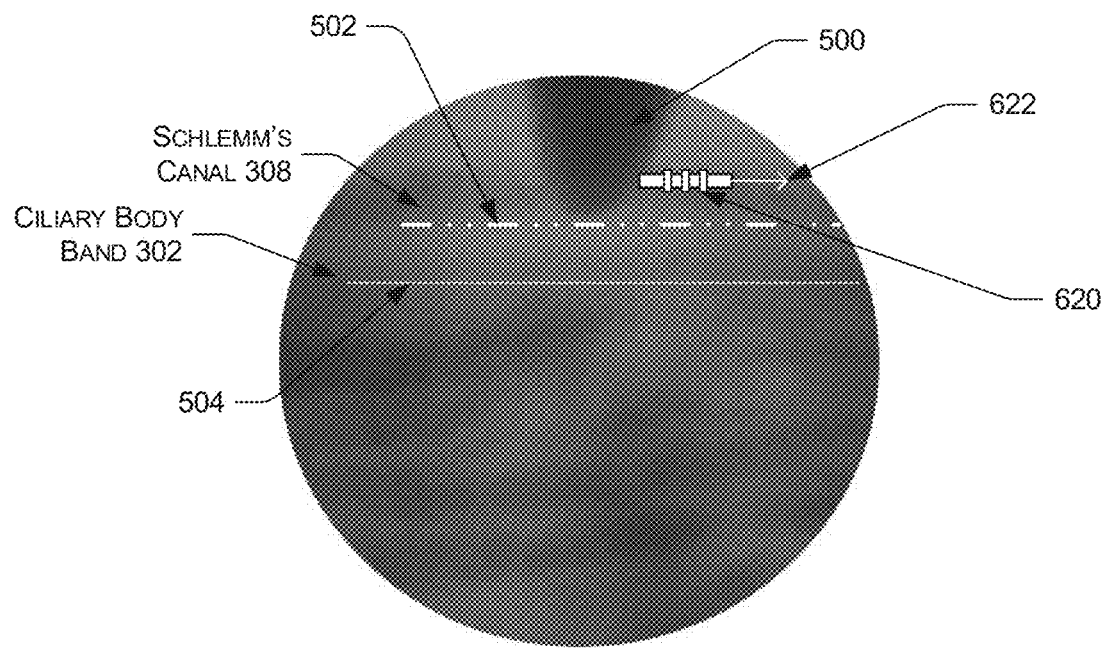
FIG. 6B shows an exemplary image overlaid with markers showing an implantation axis of the implant aligned with Schlemm's canal in accordance with some embodiments.

With reference to FIGS. 6A and 6B, a treatment probe 500 is shown in proximity of Schlemm's canal 308 and the ciliary body band 302. As illustrated, the treatment probe 500 carries a device, such as an implant 620, to the treatment site. In some embodiments, the implant 620 comprises elongate implantation axis 622 sized and shaped to extend along Schlemm's canal 308, and the implant 620 can be inserted into Schlemm's canal 308 by aligning the elongate implantation axis 622 with an elongate axis of Schlemm's canal 308, which can be helpful for appropriate delivery of the implant 620. For example, the implant 620 may comprise a sharp end sized and shaped to penetrate the trabecular meshwork and slide along Schlemm's canal 308. The fixed orientation of the camera relative to one or more of the probe 500 or the implant 620 can allow the user to align the implant with Schlemm's canal 308 with reference to structures shown in the image from the camera placed in the eye, such as with reference to one or more of the ciliary body band 302 or the scleral spur, for example without computer generated markers and when Schlemm's canal 308 is not readily apparent in the image from the camera placed in the eye. In some embodiments, the controlling unit may augment the camera images to show a Schlemm's canal identifier 502 to aid the user in locating Schlemm's canal 308 and also for determining the orientation of the treatment probe 500. As illustrated in FIG. 6A, the treatment probe 500, and thus the implant 620, is misaligned with respect to Schlemm's canal 308 and should be reoriented in order to properly deliver the implant.

As illustrated in FIG. 6B, the treatment probe 500 has been rotated to coincide with the orientation of Schlemm's canal 308. This may be done by viewing the camera image data to verify that Schlemm's canal 308 is substantially horizontal. In the alternative, or in addition, the augmented camera image data may show a Schlemm's canal identifier 502, which can be rotated by reorienting the treatment probe 500 and camera until the Schlemm's canal identifier 502 is substantially horizontal. In some embodiments, the camera and treatment probe 500 are rotated until the elongate implantation axis 622 of the implant 620 is substantially parallel with the Schlemm's canal identifier 502, for example parallel to within about 10 degrees and in some embodiments parallel to within about 5 degrees. In some instances, the treatment probe 500 and camera are rotated or repositioned until the elongate implantation axis 622 of the implant 620 is aligned with the Schlemm's canal identifier 502. This can increase the accuracy of implant delivery and deployment, and can be helpful when Schlemm's canal 308 is not readily visible in the image, for example.

In some embodiments, additional identifiers or markers are overlaid to augment the camera image data. Some of these may include identification of other anatomical features, such as a ciliary body band identifier 504 for example, distances between anatomical features, size of anatomical features, distance of the distal end of the probe from anatomical features, directional arrows other directions to aid in moving the treatment probe 500, along with other useful information.

Figure 7:
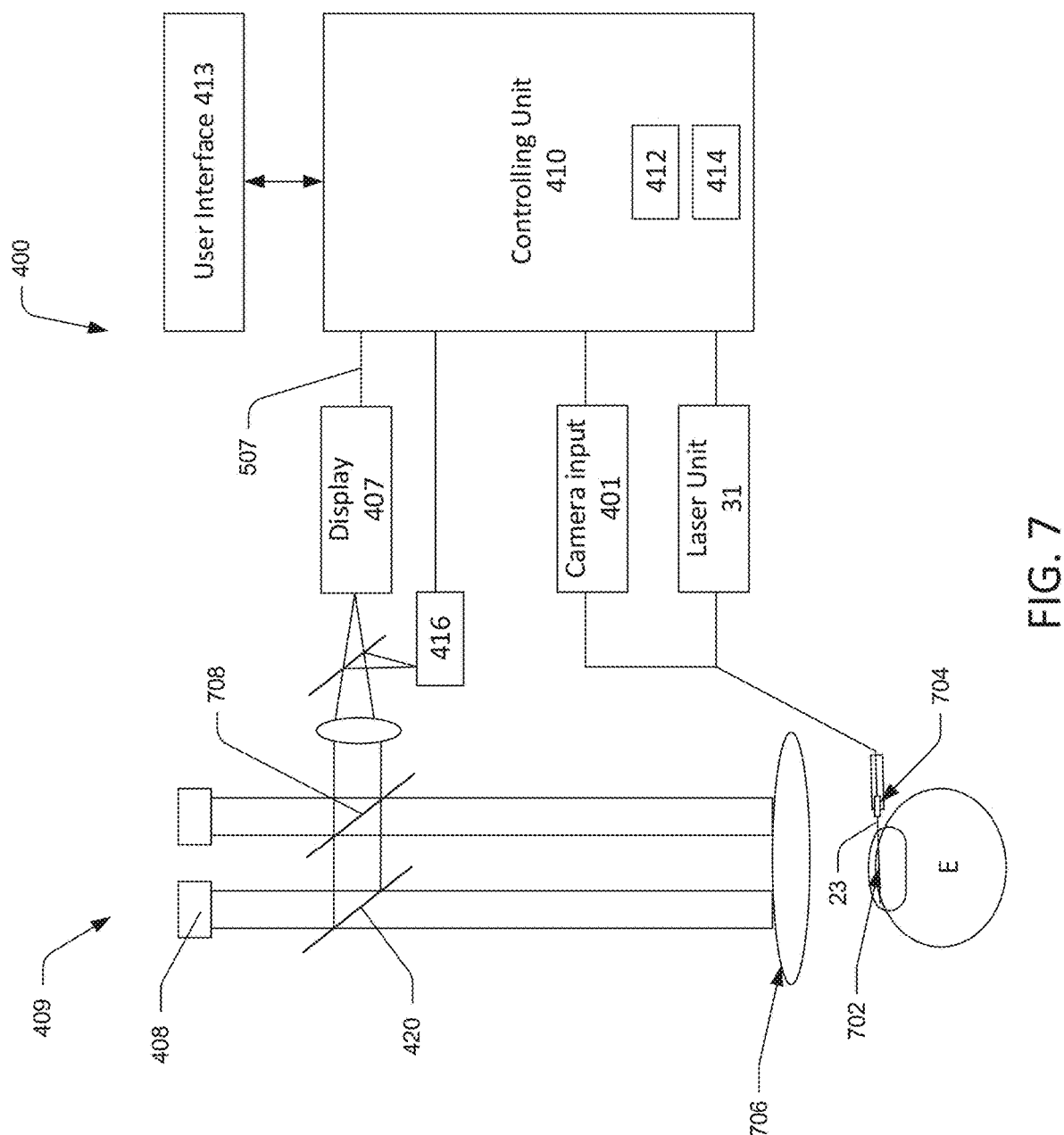
FIG. 7 shows an apparatus for eye surgery in accordance with some embodiments.

With reference to FIG. 7, a system 400 for aiding a physician to perform a surgical procedure on an eye E, is illustrated in accordance with some embodiments. The surgical operation procedure may comprise inserting an elongate probe 23 from an opening into the eye across an anterior chamber to a target tissue region comprising a trabecular meshwork and a Schlemm's canal. In some embodiments, the system 400 may comprise an optical microscope 409 for the surgeon to view the eye during the procedure in real-time. A camera input 401 receives a feed from the camera 702 placed in the eye as input. The camera input 401 is operatively coupled a processor 414 of the controlling unit 410. The processor of the controlling unit 410 can be configured with instructions to identify locations of structures of the eye and overlay indicia such as markers on the input camera images. In conjunction with the optical microscope 409, a camera 702 placed in the eye may provide a camera input 401 to the controlling unit 410. In some embodiments, a second camera 416 comprising a detector array is optically coupled to the microscope 409 to receive optical images from the operating microscope 409, and optically coupled to the processor 414 of the control unit 410. The control unit 410 can receive the image data from the camera 416 and process the image data to provide visual image data on the heads-up display 407 and overlay the visual image data on an anterior optical image of the operating microscope 409. The microscope 409 may comprise a binocular surgical operating microscope, for example. The system 400 may comprise a camera 702 that is delivered in situ along with the treatment probe 23 to provide imaging of one or more target locations before, during, or after the procedure. The camera 702 of the probe may comprise any suitable camera device, and in some cases, may comprise a CCD or CMOS imaging sensor carried on or within an endoscopic camera. Images captured by the camera may be processed by an image processing apparatus 412 of the controlling unit 410 to generate a plurality of augmented images visualized by the physician in real time.

The augmented images can be shown on a display of the heads up display 407, and combined with optical images from the microscope 409 with an internal beam splitter 420 to form monocular or binocular images as is known to one of ordinary skill in the art. As described herein, a microscope view may comprise one or more of an optical microscope image, a camera image from a camera 702 placed in the eye, a microscope image and an overlaid virtual image, or a microscope image in combination with imaging captured by the camera 702 with or without an overlaid virtual image, for example. When a microscope view includes an overlaid image, the overlaid image can be registered with the microscope image using elements which enable such alignment. Similarly, when the view includes imaging from the camera and an overlaid virtual image, the overlaid image can be registered with the imaging from the camera using elements which enable such alignment.

The images can be provided to the surgeon in many ways. For example, the surgeon can view the images with an augmented reality display such as glasses or goggles and view the surgical site through the operating microscope 409.

In some embodiments, the surgeon views the images with a virtual reality display. Alternatively or in combination, the eye can be viewed with an external monitor, and the images of the eye viewed with the external monitor with markings placed thereon as described herein. The images viewed by the surgeon may comprise monocular images or stereoscopic images, for example.

According to some embodiments, a surgeon may first view a surgical instrument, such as a probe 23, in the microscope or a video image from the operating microscope. In some cases, the surgeon may alternatively, or additionally, view images captured by the camera 702 showing the probe 23. According to some embodiments, a surgeon may view images from the microscope 409 and images captured from the camera 702 through the oculars of the microscope 409. Alternatively or in combination, the surgeon may view an augmented image or view, where additional information is overlaid on one or more of the optical microscope image or the camera image. When there is an image captured by the camera overlaid on the image from the microscope image, the surgeon can view both the microscope image and concurrently the overlaid camera image. Furthermore, the image processing apparatus 412 can detect anatomical features of the eye as described herein, and overlay markers onto the microscope image or the camera image to help guide a surgeon in identifying and locating these features. The augmented images may be presented to the physician through an eyepiece (or eyepieces) or oculars of the microscope and/or a display of the microscope, and in some embodiments may be viewed on a monitor screen. This may be beneficial to allow a surgeon to maintain a stereoscopic view of an operative site through the oculars of the microscope while simultaneously viewing superimposed or adjacent images or information concurrently either stereoscopically or monocularly, for example. Real-time images captured by the camera 702 in situ and real time treatment information can be superimposed to the live view of one or both oculars. In some embodiments, the apparatus and methods disclosed provide a real-time view including real and augmented images from both outside and inside of the anterior chamber during these surgeries.

The optical microscope 409 may be operatively coupled to the endoscope inserted into the eye in many ways. The optical microscope 409 may comprise a binocular microscope such as a stereo-microscope comprising imaging lens elements to image an object onto an eyepiece(s) comprising an ocular 408. The endoscope placed in the eye is configured to capture optical images of the eye, and may comprise any endoscope as described herein. The optical images may be transmitted to the controlling unit 410 for processing. The endoscope may comprise optical elements (e.g., lens, mirrors, filters, prisms, etc. to form an image on a sensor array as described herein. The sensor array may capture color images, greyscale images and the like, and may be introduced with the treatment probe 23 and moved with the treatment probe 23, or the treatment probe 23 may move independently of the endoscope while maintaining rotational alignment with the treatment probe 23. In some instances, the treatment probe 23 and the endoscope as described herein move together during insertion to a location of interest, and then the treatment probe 23 and the endoscope as described herein can move independently of the other while maintaining rotational alignment. The probe 23 may be the same treatment probe 500 as described herein with various embodiments. The probe 23 may be configured with a handpiece 704 to allow insertion, manipulation, or withdrawal of the probe 23, such as by a user, an actuator, a robotic arm, or otherwise.

The endoscopic images may be acquired at an appropriate image frame resolution and/or an appropriate image frame rate, and the resolution may comprise resolution of the camera inserted into the eye or optical resolution of an external sensor array optically coupled to a lens near the end of the endoscope. The image frame resolution may be defined by the number of pixels in a frame. The image resolution of the detector of the camera place in the eye may comprise any of the following resolutions: 160×120 pixels, 249×250, 250×250, 320×240 pixels, 420×352 pixels, 480×320 pixels, 720×480 pixels, 1280×720 pixels, 1440×1080 pixels, 1920×1080 pixels, 2048×1080 pixels, 3840×2160 pixels, 4096×2160 pixels, 7680×4320 pixels, or 15360×8640 pixels. The resolution of the array detector, e.g. the detector placed in the eye or the external detector, may comprise a resolution within a range defined by any two of the preceding pixel resolutions, for example within a range from 160×120 pixels to 250×250 pixels, e.g. 249×250 pixels. The imaging device or camera may have pixel size smaller than 1 micron, 2 microns, 3 microns, 5 microns, 10 microns, 20 microns and the like. The camera inserted into the eye may have a footprint on the order of 2 mm×2 mm, or 1 mm×1 mm, 0.8 mm×0.8 mm, or smaller, which is suitable for insertion alongside a treatment probe 500. The external sensor array may comprise similar dimensions.

The captured images from the sensor array, e.g. the camera inserted into the eye or the external sensor array, may comprise a sequence of image frames captured at a specific capture rate. In some embodiments, the sequence of images may be captured at standard video frame rates such as about 24p, 25p, 30p, 43p, 48p, 50p, 60p, 62p, 72p, 90p, 100p, 120p, 300p, 50i or 60i, or within a range defined by any two of the preceding values. In some embodiments, the sequence of images may be captured at a rate less than or equal to about one image every 0.0001 seconds, 0.0002 seconds, 0.0005 seconds, 0.001 seconds, 0.002 seconds, 0.005 seconds, 0.01 seconds, 0.02 seconds, 0.05 seconds, or 0.1 seconds. In some cases, the capture rate may change depending on user input and/or external conditions under the guidance of the control unit 410 (e.g. illumination brightness).

The images captured by the sensor array, e.g. the camera inserted into the eye or the external sensor array, may be captured in real time, such that images are produced with reduced latency, that is, with negligible delay between the acquisition of data and the rendering of the image. Real time imaging allows a surgeon the perception of smooth motion flow that is consistent with the surgeon's tactile movement of the surgical instruments (e.g. the elongate probe and the probe tip) during surgery. Real time imaging may include producing images at rates of about or faster than 30 frames per second (fps) to mimic natural vision with continuity of motion, and at twice that rate to avoid flicker (perception of variation in intensity). In some embodiments, the latency may comprise a time interval from capturing the images from the camera until information is shown to the user, which may be no more than about 100 ms, for example 50 ms or less. In some embodiments, the latency comprises no more than one or two frames of the image shown on the display.

In some embodiments, the optical microscope 409 may be coupled to an electronic display device 407. The electronic display 407 may comprise a heads-up display device (HUD). The HUD may or may not be a component of the microscope system 409. The HUD may be optically coupled into the field-of-view (POV) of one or both of the oculars 408. The display device may be configured to project augmented images from input 401 generated by the controlling unit 410 to a user or surgeon. The display device 407 may alternatively or additionally be configured to project images captured by the camera to a user or surgeon. The display device may be coupled to the microscope via one or more optical elements such as beam-splitter or mirror 420 such that a physician looking into the eyepieces 408 can perceive in addition to the real image, camera imaging, augmented images, or any combination represented and presented by the display device 407. The display device may be visible through a single ocular to the surgeon or user. Alternatively, the HUD may be visible through both eyepieces 408 and visible to the surgeon as a stereoscopic binocular image combined with the optical image formed with components of the microscope, for example.

The display device of heads-up display 407 is in communication with the controlling unit 410. The display device may provide augmented images produced by the controlling unit 410 in real-time to a user. As described herein, real time imaging may comprise capturing the images with no substantial latency and allows a surgeon the perception of smooth motion flow that is consistent with the surgeon's tactile movement of the surgical instruments during surgery. In some cases, the display device 407 may receive one or more control signals from the controlling unit 410 for adjusting one or more parameters of the display such as brightness, magnification, alignment and the like. The image viewed by a surgeon or user through the oculars or eyepieces 408 may be a direct optical view of the eye, images displayed on the display 407 or a combination of both. Therefore, adjusting a brightness of the images on the HUD may affect the view of the surgeon through the oculars. For instance, processed information and markers shown on the display 407 can be balanced with the microscope view of the object. The processor may process the camera image data, such as to increase contrast of the image data so the visible features are more readily detectable or identifiable.

The heads up display 407 may be, for example, a liquid crystal display (LCD), a LED display, an organic light emitting diode (OLED), a scanning laser display, a CRT, or the like as is known to one of ordinary skill in the art.

Alternatively or in combination, the display 407 may comprise an external display. For example, the display 407 may not be perceivable through the oculars in some embodiments. The display 407 may comprise a monitor located in proximity to the optical microscope 409. The display 407 may comprise a display screen, for example. The display 407 may comprise a light-emitting diode (LED) screen, OLED screen, liquid crystal display (LCD) screen, plasma screen, or any other type of screen. The display device 407 may or may not comprise a touchscreen. A surgeon may view real-time optical images of the surgical site and imaging provided by the in-situ camera 702 simultaneously from the display 407.

The resolution of the endoscope can be configured in many ways with appropriate optics and sensor resolution to image the target tissue at an appropriate resolution. The sensor array of the endoscopic camera or the external sensor array may comprise a suitable resolution for viewing tissue structures of the eye as described herein and may comprise a resolution within a range from less than 1 to 10 microns, for example within a range from about 3 to 6 microns, for example. In some embodiments, the sensor array such as the camera sensor array or the external sensor array, comprises a spatial resolution, e.g. image spatial resolution, within a range from about 10 μm to about 80 μm for tissue contacting the inclined distal end of the probe (or contacting the implant). In some embodiments, the resolution is within a range from about 20 μm to about 40 μm.

In some embodiments, lights that are present for the operating microscope provide sufficient illumination. In some embodiments, the camera placed in the eye may optionally comprise a light source suitable for producing images having suitable brightness and focus. In some embodiments, the camera placed in the eye may comprise a light-emitting diode (LED), an optical fiber for illumination, or MicroLED. In some embodiments, one or more color filters can be applied to the imaging captured by the camera in order to help isolate, locate, or otherwise identify tissue structures of interest. The camera placed in the eye may be at least partially controlled by the controlling unit 410. Control of the camera 702 by the controlling unit may include, for example, activation of the sensor array, parameters set-up, focus, brightness, contrast, application of one or more filters, or customizable control parameters.

The camera placed in the eye may comprise a miniature image sensor having a high signal to noise ratio. The camera may comprise a lens and a sensor array. In some embodiments, one or more lenses of the camera comprises borofloat glass, for example. The sensor array may have any suitable number pixels arranged in a row and column array. In some embodiments, the pixel array comprises 249×250 pixels, which may comprise rolling shutter pixels, for example. In some embodiments, the pixels have a pitch of 3 μm, which results in an optical area of 1.06 mm diameter, for example.

The system 400 may further comprise a user interface 413. The user interface 413 may be configured to receive user input and provide output information to a user. The user input may be related to control of a surgical tool such as the probe 23. The user interface 413 may receive an input command related to the operation of the optical microscope (e.g., microscope settings, camera acquisition, etc.). The user interface 413 may receive an indication related to various operations or settings about the camera. For instance, the user input may include a selection of a target location, a selection of a treatment reference marker, displaying settings of an augmented image, customizable display preferences and the like. The user interface 413 may include a screen such as a touch screen and any other user interactive external device such as handheld controller, mouse, joystick, keyboard, trackball, touchpad, button, verbal commands, gesture-recognition, attitude sensor, thermal sensor, touch-capacitive sensors, foot switch, or any other device.

In some embodiments, the camera placed in the eye is used for guiding the probe 23 and visualization of the target site. In some embodiments, the camera 702 can be configured to view tissue and the probe tip. In some embodiments, the lens of the camera is located at a distance of about 10 mm from the probe tip, for example at least about 6 mm from the probe tip. These distances allow the probe tip to be seen on the camera image to target Schlemm's canal.

The controlling unit 410 may be configured to generate an augmented layer comprising the augmented information. The augmented layer may be a substantially transparent image layer comprising one or more graphical elements. The terms "graphical element" and "graphical visual element" may be used interchangeably throughout this application. The augmented layer may be superposed onto the optical view of the microscope, optical images or video stream, and/or displayed on the display device. In some embodiments, the augmented layer is superimposed onto the optical view of the microscope, such that the transparency of the augmented layer allows the optical image to be viewed by a user with graphical elements overlaid on top of it. In some embodiments, the augmented layer may comprise real time camera images or other information obtained by one or more of the camera 702 placed in the eye or camera 416.

As described herein, the fusing of the optical microscopic image data, the camera image data, the augmented information, or any combination, may comprise incorporating the augmented information into the optical microscopic image or the camera image data, or both. The augmented image data may comprise one or more graphical elements associated with the depth information, target location, orientation information, tissue identification information, or various other supplemental information. The graphical elements may be overlaid onto the optical microscopic image and/or the camera image with a beam splitter 708, for example. A graphical element can be directly overlaid onto an image of any object visible in the optical microscopic image. A graphical element may also include any shape, boundary, or contour surrounding an image of any object in the optical microscopic image. The object may be, for example, an instrument inserted into the eye (e.g., probe), a portion of the probe, target tissues as described herein, and the like.

In some embodiments, the graphical elements may be configured to dynamically change as a position or an orientation of the probe or instrument changes relative to a target location. For example, a graphical element may indicate a location of a distal end of the probe shown in the optical image, or relative location or spacing between tissues such as inner wall of SC, TM and the like. The graphical elements may be configured to dynamically show the change in spacing between the tissue walls or distance between the tip and a target location substantially in or near real-time on the optical image, as the relative distance between the probe tip and a target location changes, and/or when the probe tip compresses on tissue (e.g., the probe tip contacting the surface of trabecular meshwork).

In some embodiments, the augmented information may comprise an orientation of the probe relative to the target location. The graphical elements may indicate the orientation of the probe relative to the target location. The graphical elements may be configured to dynamically show the orientation of the probe relative to the target location substantially in or near real-time on the optical image, as the orientation between the probe and the target location changes. In some instances, a graphical element may indicate an orientation or axial location of the elongated probe. To indicate orientation (e.g., direction), the graphical element may be provided in the form of an arrow, or a line. The graphical element may be configured to change dynamically based on movement/advancing of the probe.

The augmented layer or at least some of the graphical elements can be mapped or matched to the optical image using object recognition techniques or pattern matching techniques, such as feature point recognition, edge detection, classifiers, spatial pyramid pooling, convolutional neural networks, or any of a number of suitable object recognition algorithms, or a combination of techniques. A feature point can be a portion of an image (e.g., scleral landmarks, collector channel patterns, iris landmarks, etc.) that is uniquely distinguishable from the remaining portions of the image and/or other feature points in the image. A feature point may be detected in portions of an image that are relatively stable under perturbations (e.g., when varying illumination and brightness of an image).

Figure 8:
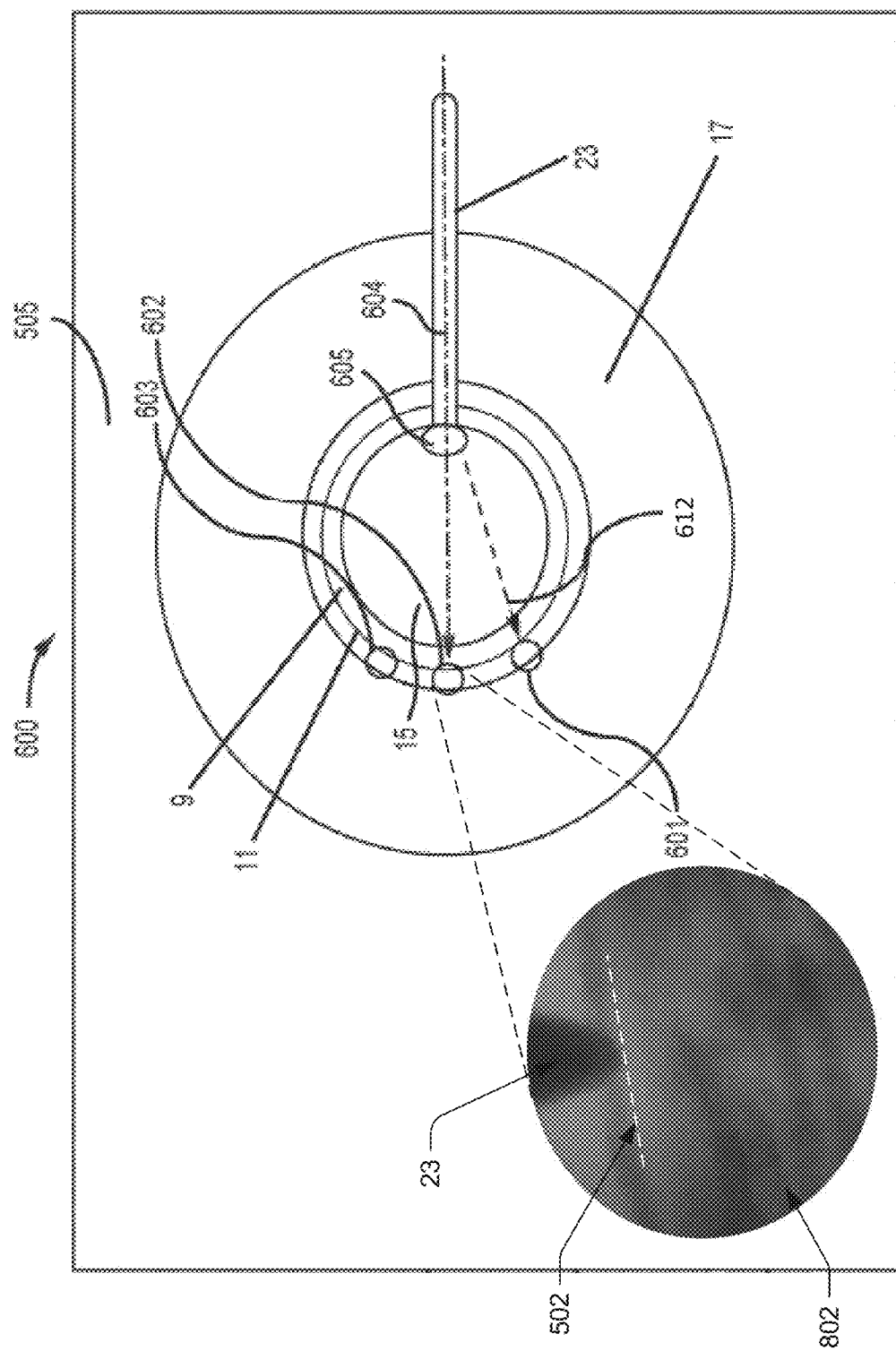
FIG. 8 shows an augmented image comprising an optical operating microscope view and an internal camera view overlaid with treatment markers.

With reference to FIG. 8, an exemplary augmented image providing an augmented view 600 is shown. As described herein, the augmented image 600 may be viewed binocularly by a user or surgeon through oculars of the microscope, and may be displayed on a heads-up display, an external display device, or a display coupled to a user interface. The augmented image or view may comprise an optical image 505 or an optical path view through the oculars of an optical microscope. The optical image 505 may comprise a top-down view of the eye. The optical image 505 or optical view may show anterior of an eye. The optical image 505 or optical view may further show an elongated probe 23. The augmented image or view 600 may comprise a plurality of graphical visual elements and one or more camera images 802 from the camera adjacent to or overlaid over the optical image 505, for example by optically coupling the display to the optical path of the microscope, such as with a beam splitter. The plurality of graphical visual elements may comprise different shapes and/or colors corresponding to different objects such that different objects shown in the optical image 505 can be easily distinguished from one another. For example, the camera image may be overlaid with an identification and location of Schlemm's Canal, such as a Schlemm's canal identifier 502, which may also provide an indication of the rotational orientation of the probe relative to the anatomical features.

The plurality of graphical visual elements may comprise one or more treatment reference markers 601, 602, 603 mapped to the one or more target locations. As discussed elsewhere herein, treatment reference markers 601, 602, 603 may correspond to target locations which are not optically visible to the surgeon in the optical image from the operating microscope. According to some embodiments, target locations may be located ab interno, and treatment of the target locations may involve an ab interno approach. In some cases, the one or more target locations may be determined or identified based on preoperative or intraoperative images. As discussed elsewhere herein, preoperative and/or intraoperative images may be obtained using either ab interno approaches and/or ab externo approaches, for example. The treatment reference markers 601, 602, 603 may be registered with one or more camera images 802. In some embodiments, a view from a microscope, such as an operating microscope, can view the probe. Additionally, the view from the probe can be superimposed on the microscope view, and the augmented view may show the end of the probe and the two images can be aligned or registered with one another. This provides the surgeon additional visual information about the position, location, orientation, and direction of the probe relative to anatomical markers. In some cases, the images from the microscope and the probe are aligned with one another enabling visible anatomical markers from both image sources to be aligned in an overlaid image, or in a picture-in-picture image. In some instances, the images from the microscope and the probe are provided to a surgeon in real-time, or in such a way that the images provide real-time information to the surgeon during a procedure.

According to some embodiments, a treatment reference marker or target location can be selected based on a location in the target tissue region that would provide a significant increase in outflow following the formation of a channel therethrough (e.g. channel passing through the trabecular meshwork, the juxtacanalicular trabecular meshwork, and the inner wall of Schlemm's canal, thus providing fluid communication between the anterior chamber and Schlemm's canal). Such a selection can be based on an identification of certain regions in collector channel networks or fields that are denser, or that contain larger vessels, or a larger distribution of vessels, or that are less obstructed, or that correspond to circumferential flow areas provided by Schlemm's canal. During real time imaging, the one or more treatment reference markers 601, 602, 603 may be superimposed over the microscope imaging, the camera imaging, or both, to the target locations by detecting a pattern of the target location identified from the preoperative imaging or real time camera imaging. In some cases, a user or surgeon may be prompted to select a target location(s) or treatment reference marker(s) through the user interface 413. In some cases, a user or surgeon may be prompted to rank or order selected target locations for treatment. Hence, the user or surgeon can specify a desired sequence in which the target locations will be treated during the surgical procedure. For example, the user or surgeon can specify that treatment reference marker 601 corresponds to a target location that will be treated first, that treatment reference marker 602 corresponds to a target location that will be treated second, and that treatment reference marker 603 corresponds to a target location that will be treated third.

As discussed elsewhere herein, treatment reference markers can be selected based on locations (e.g. locations in a target tissue region) that have been determined to correspond to bigger collector channels, more dense collector channel networks or fields, and/or and greater outflow. In some cases, the treatment reference markers can be selected in an automated fashion. In some cases, the treatment reference markers can be selected manually. Systems can be configured to guide the surgeon to direct the laser fiber to each of the selected treatment reference markers, sequentially. In some cases, a plurality of treatment reference markers may be shown simultaneously such as in the beginning of a procedure for a user to select a target location. In some cases, the plurality of treatment reference markers may be shown sequentially as the surgical operation progresses.

The plurality of graphical visual elements may also comprise a probe line 604 coaxial with the elongate probe 23. The probe line 604 shows an orientation of the probe in relation to the one or more target locations. The plurality of graphical visual elements may also comprise a distal tip marker 605 overlapping with the distal end of the elongated probe. Both of the probe line and the distal tip marker may dynamically change locations with respect to the actual positions and orientation of the elongate probe shown in the optical image or view 505, as the probe is moved within the anterior chamber of the eye. Hence, for example, a surgeon can use microscope to see the probe 23 as it enters the anterior chamber and can watch the probe as it moves relative to the eye. A detection mechanism can detect the probe 23, and an automated system or processor can generate the probe line 604 in response to the detection. Similarly, the automated system or processor can generate the guidance arrow 612.

The plurality of graphical visual elements may further comprise one or more guidance arrows or markers 612 extending from the distal tip marker 605 towards the one or more treatment reference markers (e.g., marker 601). The one or more guidance arrows 612 may be configured to guide the physician in aligning the distal end of the elongate probe to point towards the one or more target locations during the procedure or guide the physician in advancing the elongate probe towards the one or more target locations during the procedure. As discussed elsewhere herein, the one or more target locations may not be optically visible to the surgeon in the microscope view 505, and the camera imaging may be superimposed to allow the surgeon to see real-time imaging of the distal tip of the probe.

For example, upon a selection of a target location, a guidance arrow 612 may be generated pointing from the distal end of the probe (or the distal tip marker 605) to the selected target location (or the corresponding treatment reference marker) such that the physician may advance the probe parallel or coaxial to the guidance arrow. The one or more guidance arrows 612 may point radially from within the anterior chamber in different directions toward the target tissue region comprising the trabecular meshwork and the Schlemm's canal. As discussed elsewhere herein, the height of Schlemm's canal may be about half the height of the trabecular meshwork. In some cases, the one or more guidance arrows may automatically appear when the distal end of the probe is located at a predetermined distance away from the target location, for example when the distal end of the probe is located about 6 mm or less from the target location. Alternatively, the one or more guidance arrows may appear in response to a user input indicating a target location selected from the plurality of target locations.

A specific anatomical identifier may be superimposed over the microscope imaging or the camera imaging and may aid the surgeon in location the position and orientation of anatomical features. For example, a Schlemm's Canal Identifier 502 may be provided as an overlay on the camera imaging to show a surgeon the location and orientation of Schlemm's canal. As illustrated, the camera (and probe) are rotated relative to Schlemm's canal. Based upon this real-time imaging, the surgeon can reorient the probe until the Schlemm's Canal Identifier 502 is substantially horizontal and the probe is then aligned with Schlemm's canal. Other indicia, such as a horizontal marker can be overlaid so the surgeon rotate the probe until the Schlemm's Canal Identifier become substantially parallel with the horizontal marker. In some embodiments, the image from the camera placed in the eye is shown on the heads up display without markers, so that the surgeon can manipulate the probe with rotation to align the probe with structures visible in the image such as one or more of the ciliary body band 302, the iris root 16, or the trabecular meshwork 9, for example, which can be helpful to rotationally align the probe with Schlemm's canal for implantation or laser treatment with an inclined optical fiber as described herein.

In some cases, real time or substantially real-time camera images may be displayed overlying the microscope image in a picture-within-picture format. Alternatively, or in combination, information derived from the camera image may be overlaid on the microscope image. In some embodiments, when the distal end of the probe is within a predetermined distance to the selected target location, a marker or indicia may be overlaid on the microscope and/or camera imaging.

Advantageously, embodiments of the present invention provide systems and methods that enable the surgeon to effectively and accurately move and position a surgical instrument or probe, such as an excimer laser trabeculotomy (ELT) device, throughout various desired or target locations in the peripheral anterior chamber by viewing real time imaging from an in situ camera delivered with the treatment probe 500.

Embodiments of the present disclosure also enable the surgeon to effectively and accurately move and position a surgical instrument or probe, such as a laser trabeculotomy ("ELT") device, by viewing real-time imaging data from a camera located in close proximity to the probe as described herein.

Figure 9B:
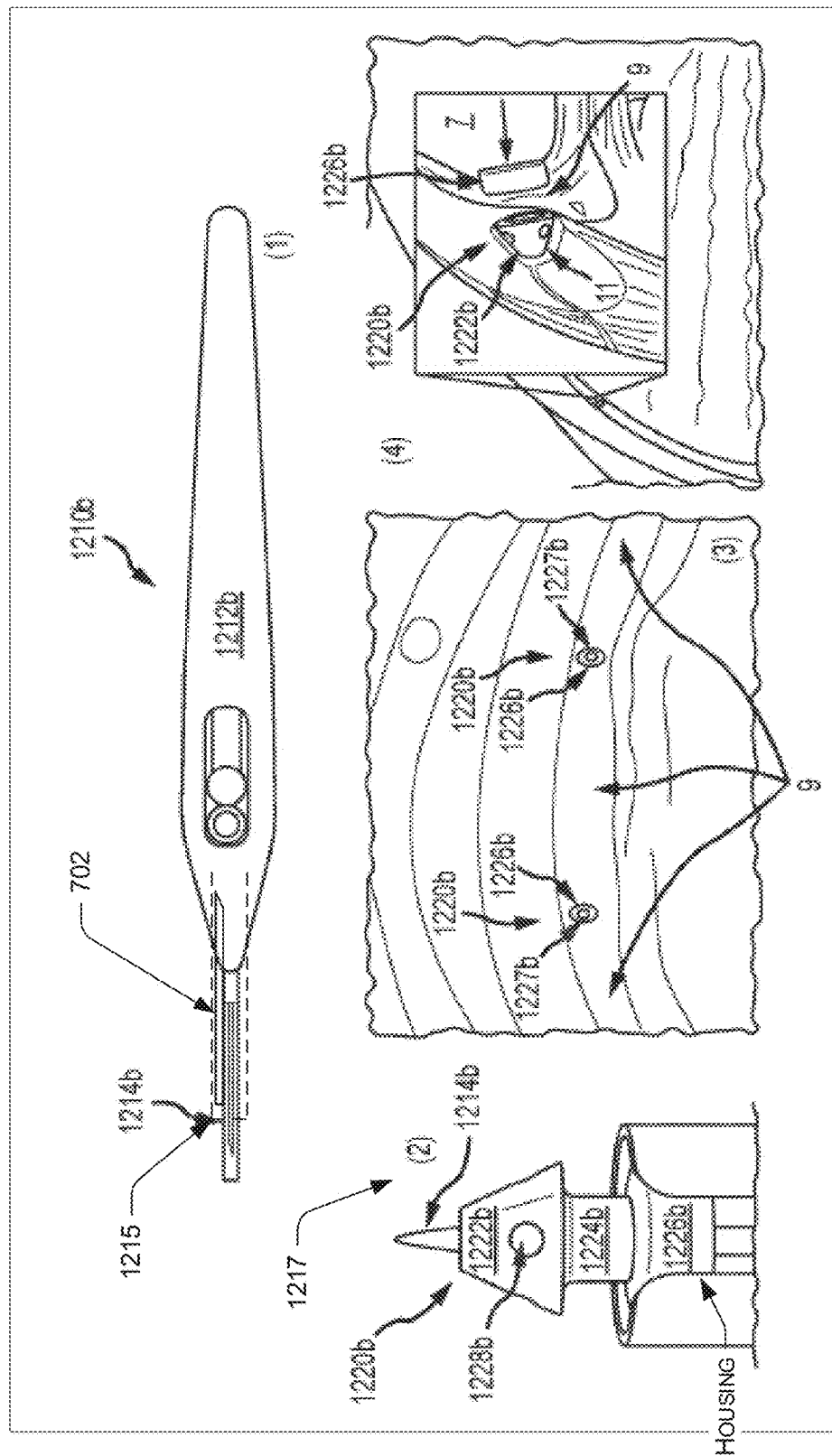
FIG. 9B shows an instrument for placement of an implant in Schlemm's canal and placement of implants in Schlemm's canal in accordance with some embodiments.

FIGS. 9A and 9B show examples of implants 620 and instruments that can be used to place implants 620 in the trabecular meshwork, in accordance with some embodiments. The implanted device 1220a may comprise a substantially elongated shape, and may any suitable implant and may be the same implant 620 as described elsewhere herein.

As illustrated in the anterior view of an eye depicted in FIG. 9A, augmented information may be overlaid onto the optical view or image 505 of the eye and the instrument in a similar as described elsewhere herein. For instance, one or more treatment reference markers 601 and an arrow or probe line 604 co-axial to the instrument 24 may be superimposed to the optical image 505. The images shown in FIG. 9A can be combined with an image from the camera placed on the eye and provided on the heads up display as described herein.

In some embodiments, the implant 620 comprises an elongate structure extending along an elongate axis sized and shaped for placement by sliding the implant along Schlemm's canal, for example with a sharp end 902 as described herein. The detector placed in the eye may comprise an axis extending along rows or columns of the detector, in which the axis of the detector is aligned with the elongate axis of the implant 620 to within about five degrees, for example to within about 3 degrees, for example to within about two degrees. For example, the axis of the camera 702 may comprise a row of detectors of the array, and the row of detectors can be aligned with the elongate axis of the implant so that the elongate axis of the implant. Alternatively, the columns of the detector array may extend along the elongate axis 904 of the implant. This can allow the user to tell when the elongate axis 904 of the implant is aligned with Schlemm's canal, for example.

A guidance arrow 612 may be displayed to guide the advancing direction and orientation of the instrument 24. In some cases, the camera 702 may be co-axial or enclosed in a housing of the instrument 24 to provide a relative position of the distal end of the instrument with respect to treatment location. In some embodiments, the camera 702 will be carried by the instrument.

In some embodiments, an elongate probe 24 may comprise one or more implants 1220a, such as an implant, loaded thereon, and the implants 1220a may be implanted in the trabecular meshwork 9 and configured to connect the anterior chamber to the Schlemm's canal and create a permanent opening into Schlemm's canal. Embodiments of the methods and apparatus described herein can be configured to aid a physician in advancing and implanting the one or more implants 1220a at target locations with aid of the graphical visual elements (e.g. treatment reference markers and arrows) registered with a real microscope image of the eye or a real camera image of the eye, or a combination of images. While the implant 1220a can be any suitable implant, in some cases, the implant will be an implant and that term will be used herein to refer to an implant delivered by the treatment probe 24. For example, the disclosed system may be configured to aid the physician in advancing and sliding an implant 1220a sideways into Schlemm's canal and positioning the implant permanently in Schlemm's canal with aid of the graphical visual elements (e.g. treatment reference marker 601, probe line 604, Schlemm's canal identifier, ciliary body band identifier, and/or guidance arrow 612) registered with the microscope image.

In some embodiments, one or more of the inserter or the implant comprises an engagement structure to align the elongate structure of the implant with the axis of the camera. As shown in FIG. 9A-1 a proximal portion of the implant may comprise a channel such as a slot or groove 906 sized and shaped to receive a protrusion of the inserter so as to fix the angle of elongate axis of the implant with the axis of the camera.

In some cases, the system may be configured to aid the physician in advancing a plurality of implants along an elongate axis 604 of the elongate probe, injecting the plurality of implants into Schlemm's canal, and positioning the plurality of implants permanently in Schlemm's canal, with aid of the graphical visual elements registered with the microscope image. For example, as depicted in FIG. 9B, Panel (1), an elongate probe 1210b includes a housing 1212b and an insertion mechanism 1214b. The probe 1210b may be the same as other embodiments described herein and may be used with the systems and methods described herein. The insertion mechanism 1214b may comprise a stylet and an inserter housing configured to be inserted into a patient's eye. The stylet may comprise a distal tip which is visible with the camera inserted into the eye to facilitate placement. The optical axis of the camera as described herein may extend substantially parallel to an elongate axis of the stylet, e.g. within about 2 degrees, or be inclined in relation to the stylet, such that the tip of the stylet appears approximately centered in the image from the camera place in the eye, e.g. appears within about 20 pixels of the center of the image from camera placed in the eye as described herein. The inserter housing 1215 may comprise a treatment probe 500 and a camera, as described herein. As depicted in Panel (2), the insertion mechanism 1214b can be loaded with an implant 1220b, and the implant 1220b can include a head 1222b, a thorax 1224b, a flange 1226b, and an outflow orifice 1228b. A stylet tip 1217 on the insertion mechanism 1214b aids in aligning and inserting the implant. FIG. 9B, Panel (3) depicts two implants 1220b which have been implanted into the trabecular meshwork 9, as viewed from the anterior chamber. As shown here, the flange 1226b of each implant 1220b includes an inlet orifice 1227b, which is in fluid communication with one or more outflow orifices (not shown).

These implants can be placed in the eye with a heads up display and camera placed in the eye as shown and described with reference to FIG. 9A For example, camera guidance embodiments as discussed with reference to FIGS. 6A and 6B can be used to help guide the surgeon to implant an implant at a target location in the trabecular meshwork corresponding to Schlemm's canal. In some cases, the target location can correspond to the location of a collector channel or be based on the distribution or density of multiple collector channels. With returning reference to FIG. 9B, as depicted in Panel (4), when an implant 1220b is implanted in the eye, the flange 1226b resides in the anterior chamber 7, the thorax (not visible) resides in the trabecular meshwork 9, and the head 1222b resides in Schlemm's canal. Because the inlet orifice is in fluid communication with the outflow orifices, aqueous humor can flow from the anterior chamber into Schlemm's canal.

The system can also be configured to aid the physician in positioning an implant in an anterior chamber angle 28 with aid of the graphical visual elements registered with the microscope image or the camera image, or both. The in-situ camera imaging guidance embodiments as disclosed herein are well suited for assisting the surgeon in delivering the implant (while loaded on the elongate probe) to the anterior chamber angle. For example, camera guidance embodiments as discussed with reference to FIGS. 6A and 6B can be used to help guide the surgeon to place an implant at a target location in the anterior chamber angle.

Figure 10:
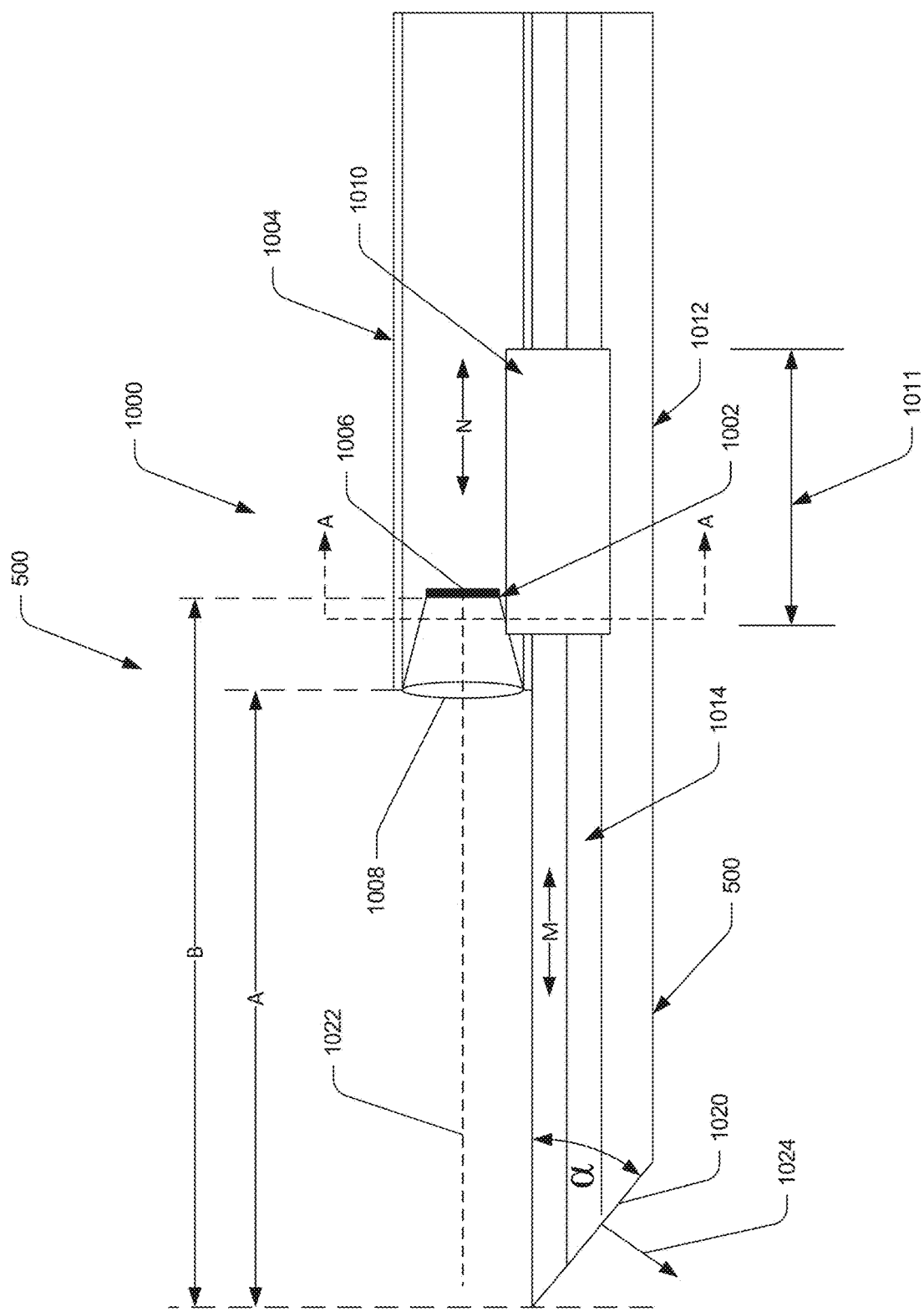
FIG. 10 shows an example of a treatment probe and a camera in accordance with some embodiments.

With reference to FIG. 10 an example treatment probe 500 and camera 1002 are illustrated in accordance with some embodiments. The camera 1002 is contained within a camera housing 1004 and comprises a detector array 1006 and a lens 1008. As described elsewhere herein, the detector array 1006 may comprise an array with any suitable resolution for example within a range from 200×200 to 300×300 pixels, for example.

A fastener 1010 such as a clip has a fastener length 1011 and may be used to couple the camera housing 1004 to an optical fiber housing 1012. The optical fiber housing 1012 may comprise an optical fiber 1014 configured to deliver light energy to a treatment site. The optical fiber housing 1012 and the optical fiber 1014 may comprise a treatment probe 500 and the camera 1002 and camera housing 1004 may comprise an imaging probe 1000. The optical fiber housing 1012 may be configured with one or more structures that cooperate with the fastener 1010 to secure the optical fiber housing 1012 and the camera housing 1004 in a fixed relative rotational orientation. In other words, the fastener 1010 may secure the camera housing 1004 and the optical fiber housing 1012 together such that neither the camera housing 1004 or the optical fiber housing 1012 can rotate substantially about their longitudinal axes independently of the other, for example no more than about 2 degrees. The fastener 1010 may be permanently affixed to either the camera housing 1004 or the optical fiber housing 1012 and selectively engage the other. Alternatively, the fastener 1010 may comprise a separate part configured to couple to the treatment probe 500 and the imaging probe 1000.

The distal end of the treatment probe 500 may be formed with an inclined surface 1020 having an angle α relative to the longitudinal axis of the treatment probe 500. In some embodiments, the distal end of the treatment probe 500 or the distal end of the optical fiber 1014, or both, are inclined at an angle α of about 45 degrees to about 65 degrees and optionally at an angle within a range from about 50 degrees to about 60 degrees. In some embodiments the angle α of the distal end of the treatment probe 500 is the same as the angle of the distal end of the optical fiber 1014. In some embodiments, the angle α of the distal end of the treatment probe 500 is within 10 or fewer degrees of the angle of the distal end of the optical fiber 1014.

While the illustrated embodiment shows a single optical fiber 1014, it should be appreciated that a bundle of optical fibers could be used with the disclosed systems and methods. In some examples, the treatment probe 500 comprises a bundle of optical fibers that each have a distal end at or near the angle of the distal end of the treatment probe 500.

In some embodiments, the camera housing 1004 can translate along its longitudinal axis in a direction N independently of the optical fiber housing. In some cases, the translation distance of the camera housing 1004 is fixed, such that there are limits to the translation distance of the camera housing 1004 relative to the optical fiber housing 1012. In some embodiments, the distal end of the probe extends beyond the lens 1008 of the 1002 camera by a distance A within a range from about 2 mm to about 10 mm, or within a range from about 2.5 mm to about 5 mm. In embodiments, in which the camera housing 1004 can translate independently of the optical fiber housing 1012, the translation distance may be bounded by these dimensions, such that the lens 1008 of the camera 1002 can be moved to about 2 mm to about 10 mm from the distal end of the optical fiber housing 1012.

Similarly, the detector array 1006 may be positioned a distance B from the distal end of the treatment probe 500. The distance B may be within the range of from about 2.5 mm to about 10.5 mm and optionally within the range of from about 3 mm to about 6 mm. The camera housing 1004 may be limited in its translational range of motion relative to the optical fiber housing 1012 such that the detector array 1006 may be limited within the range of from about 2.5 mm to about 10.5 mm at the limits of its longitudinal travel. The travel limits may be provided by any suitable structure or mechanism, such as slots, grooves, protrusions, bosses, stops, and the like.

The treatment probe 500 may be translated in a direction M, and the camera housing 1004 may be secured to the treatment probe 500 such that the camera housing 1004 is translated along with the treatment probe 500. In some embodiments, the camera housing 1004 may have a rigid attachment to the optical fiber housing 1012 and be selectively released to provide a degree of freedom for translating along its longitudinal axis within translational limits, as described herein.

The camera 1002 of the imaging probe 1000 may comprise an optical axis 1022. The optical axis 1022 may extend approximately parallel to an elongate axis of the optical fiber 1014, for example parallel to within about 5 degrees. Although the optical axis 1022 can be inclined relative to the elongate axis of the treatment probe 500 as described herein. In some embodiments, the optical fiber 1014 comprises an inclined distal end 1020. The rows and columns of the detector array 1006 can be aligned with the inclined distal end of the probe, so that the images from the camera placed in the eye are aligned with the inclined distal end 1020 of the probe. The inclined distal end 1020 may comprise a substantially flat surface that defines a surface normal vector 1024. The camera 1002 can be positioned in relation to the surface normal vector 1024 in many ways. In some embodiments the surface normal vector 1024 and the optical axis 1022 extend along a common plane. In some embodiments, the inclined distal end 1020 faces away from the optical axis 1022, for example with the surface normal vector 1024 directed away from the optical axis 1022. In alternative embodiments, the inclined distal end 1020 faces toward the optical axis 1022, for example with the surface normal vector 1024 directed toward the optical axis.

In some embodiments, the rows and columns of the detector array 1006 are aligned with the inclined distal end 1020 of the probe 500, such that the columns of the array extend in a direction corresponding to the component of the surface normal vector 1024 extending away from the elongate axis of the optical fiber. Alternatively the rows and columns of the detector array 1006 can be rotated relative to the inclined distal end 1020 of the fiber, and a processor used to rotate the image shown to the surgeon in order to align the image of the eye from the camera placed in the eye with the inclined distal end 1020 of the probe.

Figure 11:
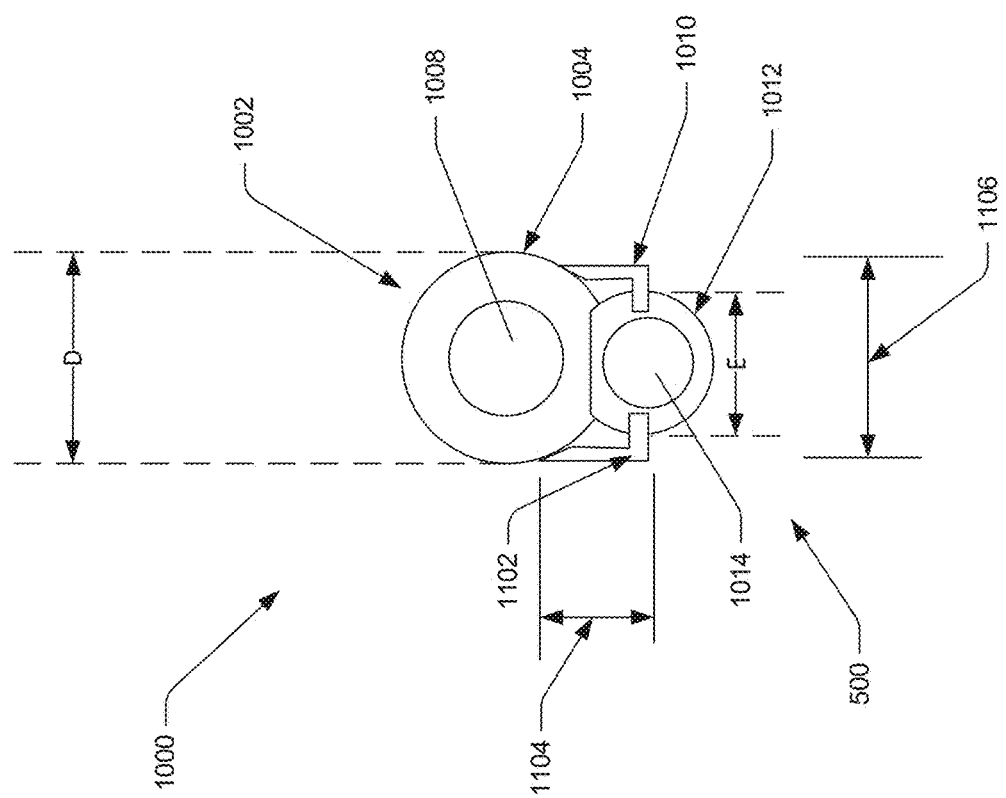
FIG. 11 shows a cross sectional schematic view of an example treatment probe and camera taken along the line A-A from FIG. 10 in accordance with some embodiments.

FIG. 11 is a cross-sectional schematic view of the probe 500 of FIG. 10 taken along the line A-A. The probe 500 may have a camera 1002 comprising a camera housing 1004 and a lens 1008. An optical fiber housing 1012 may comprise one or more optical fibers 1014. The optical fiber housing 1012 may be affixed to the camera housing 1004 to prevent independent rotation of the camera housing 1004 or the optical fiber housing 1012.

According to some embodiments, a fastener 1010 may affix the optical fiber housing 1012 to the camera housing 1001. The fastener 1010 may comprise a clip which may be secured in a longitudinal groove of the optical fiber housing 1012. In some embodiments, the clip is affixed to the camera housing 1004 and comprises an engagement structure 1102 such as, for example, a flat engaging surface, a slot, a key, a groove, an aperture, a protrusion, or other suitable structure. In some embodiments, the clip couples the optical fiber housing 1012 to the camera housing 1004 with a fixed angular orientation.

In some embodiments, the camera housing 1004 or the optical fiber housing 1012, or both, have flat engaging surfaces to provide intimate surface contact between the camera housing 1004 and the optical fiber housing 1012, and to orient the optical fiber housing 1012 for receiving the fastener.

The camera housing 1004 has a maximum dimension D within the range of about 0.8 mm to about 1.2 mm. The optical fiber housing 1012 has a maximum cross-sectional dimension E within the range of from about 300 μm to about 600 μm. While the camera housing 1004 and the optical fiber housing 1012 are represented schematically as having a generally cylindrical cross section, the respective housings may have any suitable cross-sectional shape, such as ovoid, hexagonal, octagonal, circular, or any suitable shape.

In some embodiments, the fastener 1010 may comprise a clip or an aperture to engage one or more of the camera housing 1004, the inserter housing 1215, or the optical fiber housing 1012 and optionally the clip comprises the engagement structure 1102 sized and shaped to receive the camera housing 1004, the inserter housing 1215, the optical fiber housing 1012, or a combination.

The fastener may allow the camera housing 1004 to slide in relation to the inserter housing 1215 or the optical fiber housing 1012 while the rotational orientation of the camera 1002 to the inserter housing 1215 or the optical fiber housing 1012 remains fixed.

The imaging probe 1000 comprising the camera 1002 may be fastened to the treatment probe 500 with the fastener, such that the rotational orientation of the camera 1002 relative to the rotational orientation of the instrument is fixed, that is, the camera 1002 cannot substantially rotate independently of the treatment probe 500, e.g. more than five degrees, for example no more than two degrees, e.g. no more than one degree. In some embodiments, the rotation orientation is fixed by use of cooperating structures that reduces the likelihood of relative rotation between the camera 1002 and the instrument. In some embodiments, a clip secures the camera 1002 or the camera housing 1004 to the instrument and fixes the rotational orientation, for example, prevents the camera 1002 from rotating relative to the instrument. This may be accomplished by any suitable structure or method, but in some examples, is accomplished by one or more clips that fix the rotational of the camera 1002 or camera housing 1004 relative to the probe 500 or optical fiber housing 1023. This may also be accomplished by abutting the fiber optic of the instrument against a flat surface of the sensor array. In some embodiments a fastener 1010 couples the inserter housing 1215 or the optical fiber housing 1012 to the camera housing 1004 with a fixed angular or rotational orientation. The fastener may comprise an engagement structure which may be a flat surface, a slot, a key, a keyway, a groove, an aperture, a protrusion, a boss, or some other suitable structure for fixing the orientation of one or more of the optical fiber housing 1012, the camera housing 1004, or the inserter housing 1215.

In some embodiments, a fastener 1010 comprises a clip that engages the camera housing 1004, the inserter housing 1215, or the optical fiber housing 1012 and in some cases, the clip engages with the camera housing 1004, the inserter housing 1215, or the optical fiber housing 1012 to provide a fixed orientation. Alternatively or in combination, the fastener 1010 comprises an aperture sized and shaped to receive the camera housing 1004, the inserter housing 1215, or the optical fiber housing 1012 and to provide a fixed orientation. In some instances, the fastener 1010 allows the camera housing 1004 to slide relative to the inserter housing 1215 or the optical fiber housing 1012.

In some embodiments, the fastener 1010 fixes a distance between the distal end of the treatment probe 500 and the detector array 1006. The fastener 1010 may comprise a stop, a pair of stops, an interlocking mechanism, a nesting mechanism, a circumferentially extending channel, a circumferentially extending protrusion, an annular protrusion, an annular recess, or some other suitable structure that provides a stop to limit the relative distance between the distal end of the probe 500 and the detector array 1006. In some embodiments, distance between the distal end of the probe 500 and the detector array are fixed, while in other cases there is relative movement therebetween up to the limits provided by the fastener.

FIG. 10 shows a length of the fastener 1010 extending along an elongate direction of the imaging probe 100 and the treatment probe 500. FIG. 11 shows a first direction transverse to the elongate direction of the treatment probe 500 and the imaging probe 1000. The fastener 1010 can be sized and shaped to extend around at least a portion of the camera housing 1004 and a portion of the inserter housing 1215 as described herein or the optical fiber housing 1012 as described herein. The fastener 1010 comprises a first distance 1104 transverse to the camera housing 1004 and the inserter housing 1215 or the optical fiber housing 1012, and a second distance 1106 transverse to the camera housing 1004 and the inserter housing 1215 or the optical fiber housing 1012 as shown in FIG. 11. The elongate distance 1011 of the fastener 1010 may comprise a third distance along an elongate axis the camera housing 1004 and the inserter housing 1215 or the optical fiber housing 1012. In some embodiments, the second distance is less than the first distance, and the third distance is greater than the second distance and the first distance. In some embodiments, the first distance is within a range from about 1.0 mm to about 2 mm, the second distance within a range from about 0.8 to 1.5 mm and the third distance within a range from about 2 mm to about 20 mm, for example. In some embodiments these ranges are smaller, for example the first distance can be within a range from about 1.3 to about 1.7 mm, the second distance can be within a range from about 1.0 to 1.3 mm, and the third distance within a range from about from about 2 mm to about 10 mm. The third distance along the elongate direction can be longer than the first transverse distance and the second transverse distance to add stiffness to the coupling between the imaging probe and the treatment probe 500.

Figure 12A:
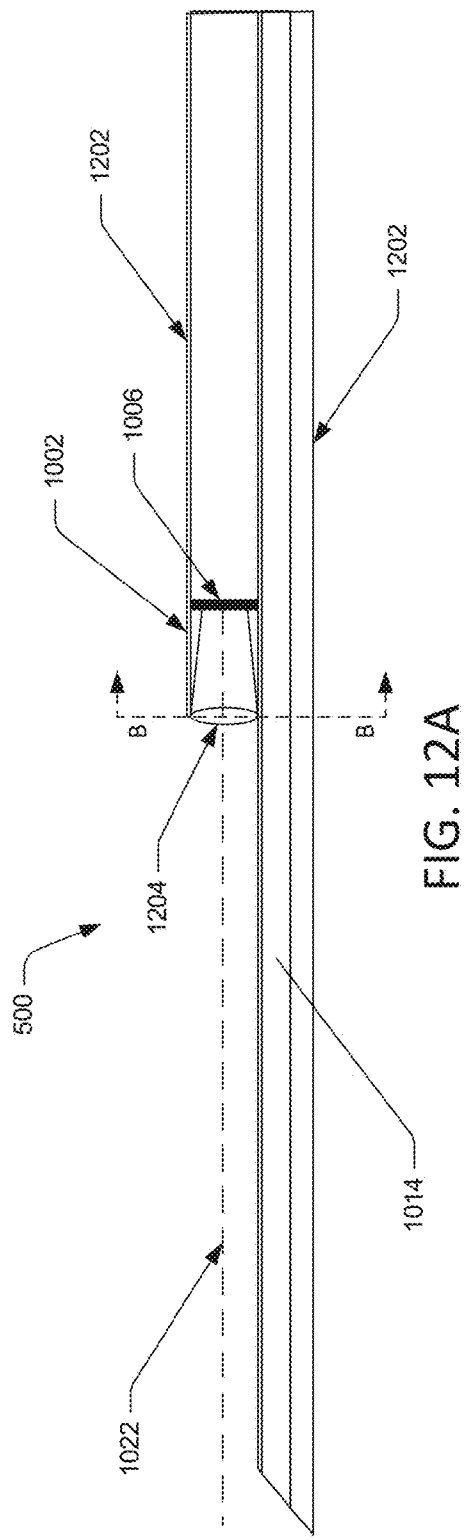
FIG. 12A shows an example of a treatment probe and a camera in accordance with some embodiments.
Figure 12B:
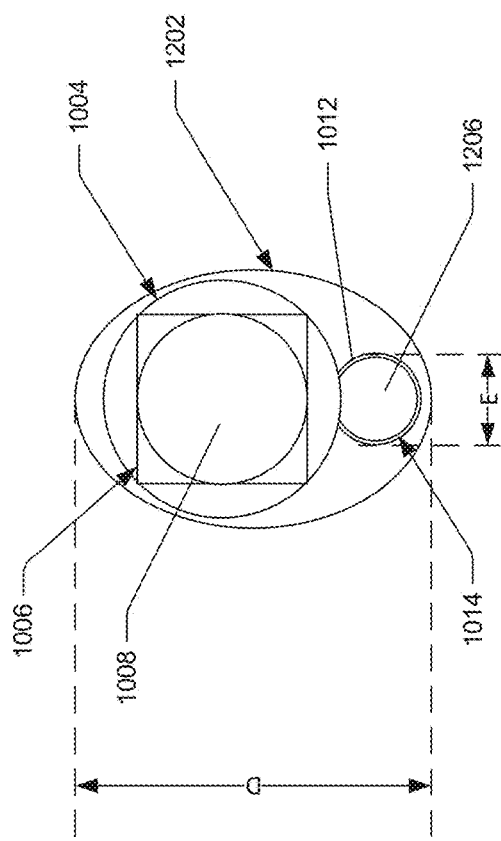
FIG. 12B shows a cross sectional schematic view of an example treatment probe and camera taken along the line B-B of FIG. 12A in accordance with some embodiments.

With reference to FIGS. 12A and 12B, an example of a treatment probe 500 and camera 1002 enclosed within a housing 1202 is shown, in accordance with some embodiments. The treatment probe 500 comprises an integrated housing 1202 that encloses an optical fiber and a camera. The camera 1002 may comprise a detector array 1006, a lens 1008, and circuitry to couple the camera 1002 to a controlling unit as described herein. The integrated housing 1202 may comprise an aperture 1204 to allow a lens 1008 of the camera 1002 to view features of interest. An optical axis 1022 extends from the detector array 1006 and through the lens 1008 toward the distal end of the probe. The optical fiber 1014 has a distal end that is spaced a distance from the lens 1008, as previously described.

FIG. 12B is a cross-sectional schematic view of the probe of FIG. 12A taken along the line B-B. The integrated housing 1202 has a maximum dimension D that is selected to allow insertion of the probe into the eye to access a treatment location, such as within the anterior chamber of a patient's eye. In some embodiments, the maximum dimension D is within the range of from about 0.5 mm to about 3 mm, or from about 1 mm to about 2 mm, for example In some embodiments, the probe comprises a length within a range from about 10 mm to about 50 mm sized for insertion into the eye. The length of the probe, in some cases, is selected to allow the probe to reach and compress the trabecular meshwork with the inclined distal end within the eye of a patient.

The optical fiber core 1206 and cladding may be encased by an optical fiber housing 1012. The optical fiber housing 1012 may comprise any suitable material, but in some cases is stainless steel. The optical fiber housing 1012 has a maximum cross-sectional dimension E within the range of from about 300 µm to about 1000 µm. In some embodiments, the optical fiber housing 1012 has a diameter within a range from about 100 µm to about 500 µm, or 150 µm to about 300 µm, and optionally within a range from about 150 µm to about 250 µm. The camera housing 1004 may comprise a maximum cross-sectional dimension within the range of from about 0.8 mm to about 1.2 mm. As shown in FIG. 12B, in some embodiments, the integrated housing 1202 encloses both the camera 1002 and the optical fiber 1014 and may comprise any suitable cross-sectional shape and size. In some embodiments, the integrated housing 1202 is sized and shaped to deliver the camera 1002 and optical fiber 1014 to the anterior chamber of a patient's eye, and more specifically, deliver the optical fiber 1014 toward the trabecular meshwork to deliver laser energy to the trabecular meshwork. In some embodiments the optical fiber 1014 comprises an inclined distal end to uniformly comprise the trabecular meshwork to form one or more openings into Schlemm's canal.

Figure 13:
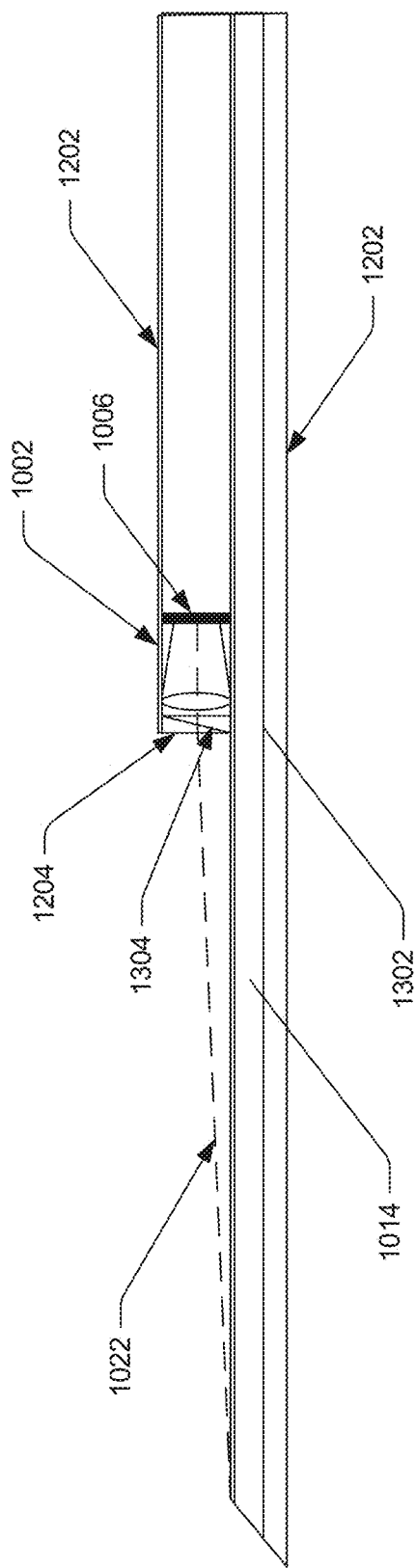
FIG. 13 shows an example of a treatment probe and a camera in accordance with some embodiments.

FIG. 13 shows a probe 500 comprising an optical axis 1022 inclined relative to an elongate axis 1302 of the treatment probe 500. The probe 500 may be similar, or identical, to probes shown and described in other figures, and may share components with embodiments of probes described herein. The inclined optical axis 1022 can decrease movement of out of focus tissue as the probe 500 is advanced toward the target location, and may facilitate movement of the treatment probe 500 toward the target tissue. Although the treatment probe 500 is shown having an integrated housing 1202 that comprises a camera 1002 and an optical fiber 1014, the optical fiber 1014 and camera 1002 can be coupled to each other with a fastener as described herein, so as to incline the optical axis 1022 in relation to the distal end of the probe 500. The inclined optical axis 1022 can be combined with the implant placement devices as described herein. For example, the optical axis 1022 can be oriented toward the distal tip of the implant placement probe or the implant on the distal end of the probe.

In some embodiments, a prism 1304 is located along the optical path to deflect the optical axis 1022. The prism 1304 may comprise a discrete optical element located along the optical path with the lens. Alternatively, the prism 1304 may be located on a surface of the lens. In some embodiments, the lens comprises a wedge in order to deflect light along the optical path.

In some embodiments, the inclined optical axis 1022 of the camera 1002 may allow the camera 1002 to image an implant carried by the integrated housing 1202 with the implant approximately centered in the camera image. Alternatively or in combination, the inclined optical axis 1022 may allow the camera 1002 to image the distal tip of the optical fiber 1014 approximately centered in the image, to allow the surgeon to use the distal tip to aim the probe 500 at the treatment site. In some embodiments, the camera 1002 is slidable relative to the integrated housing 1202, and the optical axis 1022 can thereby be moved, such as to pass through the distal tip of the optical fiber 1014 or beyond. For example, the imaging probe can be coupled to the treatment probe 500 with a slidable fastener as described herein. Alternatively, the camera 1002 can be slidable relative to the treatment probe 500 within the integrated housing 1202.

Figure 14:
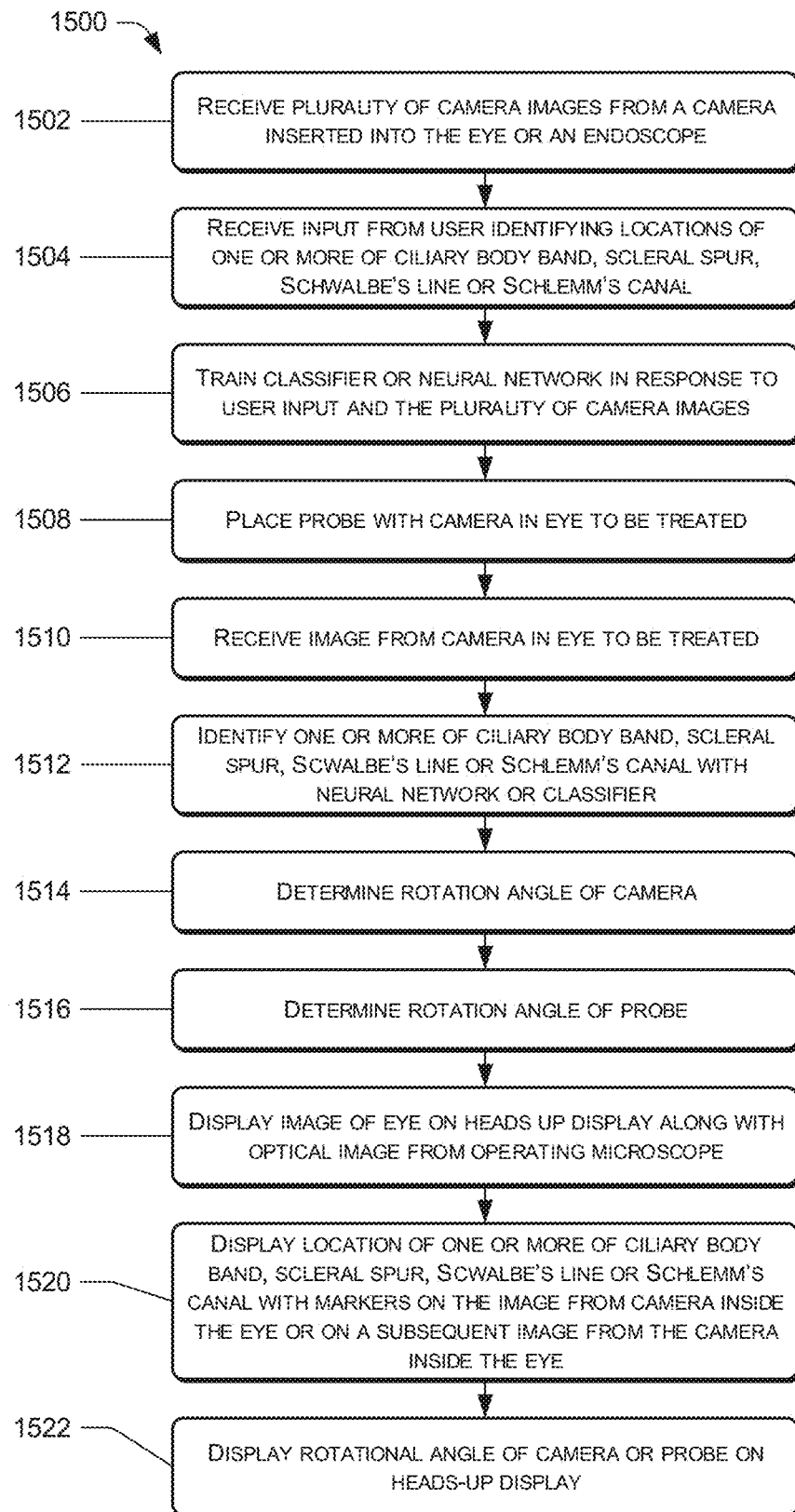
FIG. 14 is a flowchart diagram showing methods in accordance with some embodiments.

FIG. 14 shows a method 1500 of treating an eye, in accordance with some embodiments. At a step 1502, a system receives a plurality of camera images from a camera inserted in the eye of a patient or in an endoscope. In some embodiments, an endoscope comprising a lens and a fiber optic array transmits light captured at the treatment site to a detector array outside the patient that creates images. At a step 1504, user input is received that identifies anatomical locations such as one or more of ciliary body band, scleral spur, Schwalbe's line, or Schlemm's canal. The user input may be provided by a user such as a surgeon with a touch screen display identifying locations of one or more of the ciliary body band, the iris root, the scleral spur, Schwalbe's line or Schlemm's canal. At a step 1506, a classifier or neural network is trained in response to user input and the plurality of camera images, which may additionally or alternatively comprise endoscope images. The classifier or neural network, in some cases, is trained in feature recognition such that the classifier or neural network can detect and identify anatomical features within the eye of a patient, such as one or more of ciliary body band, scleral spur, Schwalbe's line, or Schlemm's canal, for example. The classifier or neural network may comprise any combination of suitable image processing algorithms. In some embodiments, the neural network comprises a convolutional neural network as is known to one of ordinary skill in the art of training neural network. The classifier may comprise any suitable classifier, such as machine learning, for example supervised machine learning such as machine learning with Bayesian statistics, for example random forest as is known to one of ordinary skill on the art. Image processing algorithms such as edge detection can be used as input to the classifier. Once the neural network or classifier, or both have been trained, the trained classifier or neural network can be used to identify structures of the eye and provide markers as disclosed herein.

At a step 1508, the probe with the camera is placed in an eye to be treated. According to some embodiments, the probe with the camera comprises an endoscope or a fiberscope to image the eye to be treated. Alternatively to placing the detector array inside the eye, the detector array can be located outside the eye as described herein.

At a step 1510, the processor receives images from the camera or endoscope placed in the eye. The images may be acquired at a desired framerate. In some embodiments, the framerate approximates smooth motion, such as about 15 fps, 20 fps, 25 fps, 30 fps, or greater.

At a step 1512, anatomical features are identified, such as one or more of a ciliary body band, scleral spur, Schwalbe's line, or Schlemm's canal, such as by using a neural network or a classifier.

At a step 1514, a rotation angle of the camera or endoscope relative to the one or more anatomical features is determined.

At a step 1516, a rotation angle of the probe is determined. In some embodiments, the rotation angle of the probe is fixed with respect to the rotation angle of the camera or endoscope, and thus determining the rotation angle of the camera results in the same rotation angle of the probe.

At a step 1518, an image of the eye from the interior of the eye provided by the endoscope is displayed on a heads up display along with an optical image from an operating microscope. The endoscope may comprise a camera inserted into the eye, which provides the image, or an endoscope with an external sensor array, which provides the image. This image may be presented as a picture in picture display and may be displayed through one or both eyepieces of a microscope. Although reference is made to a heads-up display, the display may comprise one or more of a two-dimensional display, e.g. a monitor, heads-up display of an operating microscope, an augmented reality display, a virtual reality display, a three-dimensional display, or a stereoscopic image display, e.g. with depth perception.

At a step 1520 a marker is shown on the image from the camera or endoscope placed in the patient. The marker can be overlaid on of one or more of the ciliary body band, scleral spur, Schwalbe's line, or Schlemm's canal. The one or more markers can be placed on the image used to identify the tissue structure, or on a subsequent image from the camera or endoscope inside the eye. In some cases, the markers are overlaid on the images from the camera or endoscope to present an augmented image.

At a step 1522, the rotational angle of the camera, the endoscope, or the probe is shown on the heads-up display. The rotation angle may be a numerical value, one or more lines, or an angle with respect to a horizontal line, or some other indicia indicating a rotation angle of the probe or the camera, for example a green light when the probe is rotationally aligned within an appropriate tolerance, for example to within 5 degrees.

One or more steps of the method of FIG. 14 may be performed with circuitry or processor instructions as described herein, for example, one or more of a processor or a logic circuitry of the systems described herein. The circuitry may be programmed to provide one or more steps, and the program may comprise program instructions stored on a computer readable memory or programmed steps of the logic circuitry such as with programmable array logic or a field programmable gate array, for example.

Although FIG. 14 shows a method in accordance with some embodiments, a person of ordinary skill in the art will recognize many variations and adaptations in accordance with the teachings disclosed herein. For example, steps of the method can be removed. Additional steps can be provided. Some of the steps can be repeated. Some of the steps may comprise sub-steps. Some of the steps can be repeated. The order of the steps can be changed.

The convolutional neural network may be used to classify image data, and this, or an alternative machine learning algorithm, may be applied to result in the generation of markers and other indicia used to augment images from an in-situ camera or endoscope, or images from an operating microscope, or both. The result is the generation of augmented images that allow a surgeon to quickly identify anatomical features and determine that the probe is properly aligned with the anatomical features, such as for deploying an implantable device that requires proper alignment and/or orientation.

Figure 15:
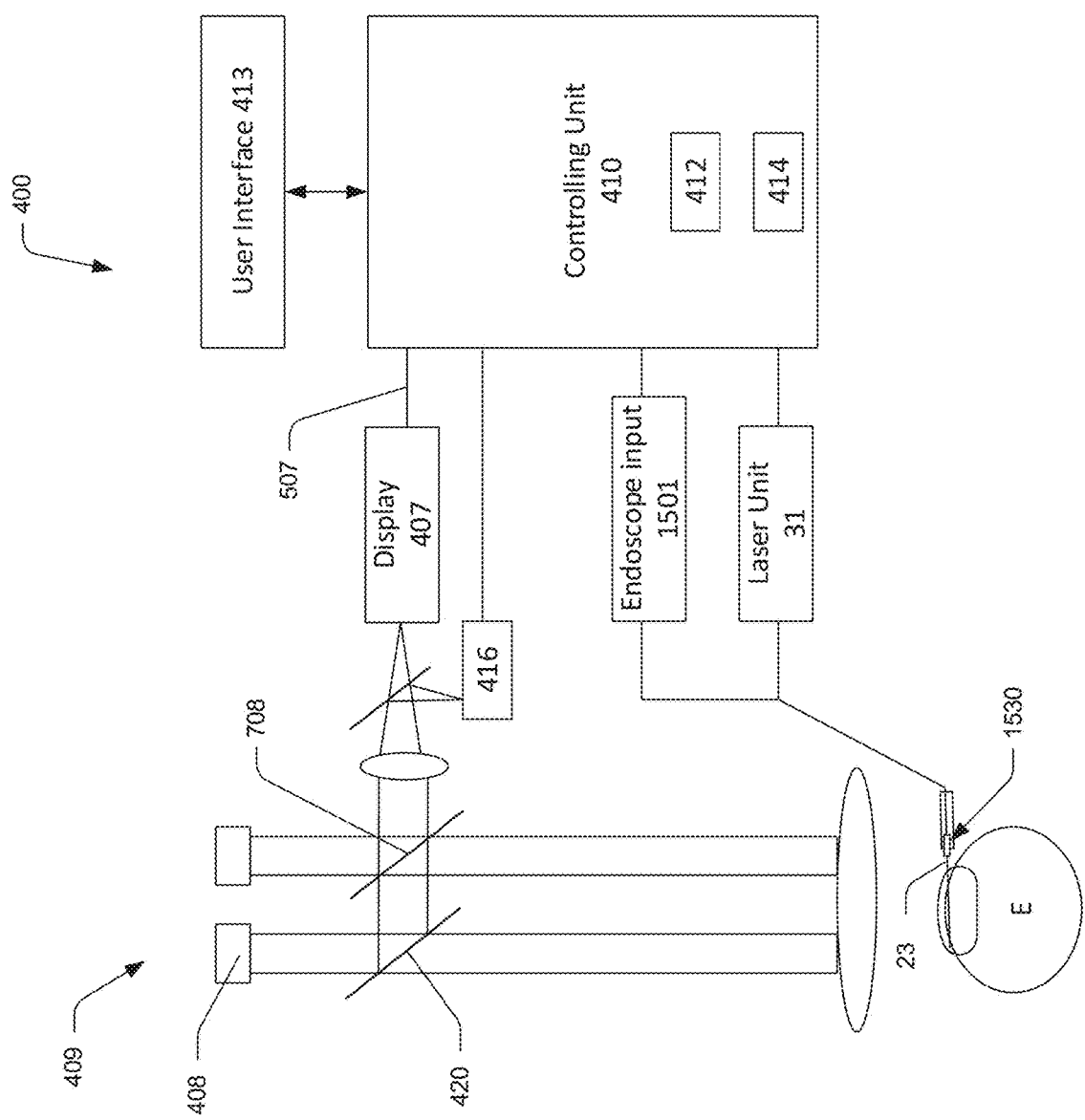
FIG. 15 shows an apparatus for eye surgery in accordance with some embodiments.

With reference to FIG. 15, a system 400 for aiding a physician to perform a surgical procedure on an eye E with an endoscope 1530, is illustrated in accordance with some embodiments. The surgical operation procedure may comprise inserting an elongate probe 23 from an opening into the eye across an anterior chamber to a target tissue region comprising a trabecular meshwork and a Schlemm's canal. In some embodiments, the system 400 may comprise an optical microscope 409 for the surgeon to view the eye during the procedure in real-time. An endoscope input 1501 receives a feed from the endoscope placed in the eye as input. The feed may comprise an optical feed or an electrical feed, and combinations thereof. In some embodiments, the endoscope is coupled to the endoscope input 1501 with a flexible cable. The flexible cable may comprise an ordered array of optical fibers, in which the arrangement of optical fibers is substantially fixed on both ends to transmit an image of the eye to the eye to the endoscope input 1501. The distal end of the optical fiber array can be substantially fixed with respect to a lens that forms and image on the distal end of the optical fiber array, and the proximal end of the optical fiber array can be substantially fixed with respect to a detector array that receives the image from the array of optical fibers. In some embodiments, the substantially fixed arrangement on both ends can allow rotation of the probe while maintaining orientation of the image formed on the distal end of the optical fiber array with respect to the image transmitted from the proximal end of the optical fiber array to the detector array.

The endoscope input 1501 is operatively coupled to a processor 414 of the control unit 410. The endoscope input 1501 may comprise an input from a sensor of a camera placed in the eye or an external sensor array as described herein. The processor 414 of the control unit 410 can be configured with instructions to identify locations of structures of the eye and overlay indicia such as markers on the input endoscope images. In conjunction with the optical microscope 409, an endoscope placed in the eye may provide an endoscope input 1501 to a controlling unit 410. In some embodiments, a camera 416 comprising a detector array is optically coupled to the optical microscope 409 to receive optical images from the operating microscope, and optically coupled to the processor of the control unit 410. The control unit 410 can process the images from the camera 416 and process the images to provide visual image data on the heads up display 407 to overlay the visual image data on an anterior optical image of the operating microscope. Although reference is made to a heads-up display, the display 407 may comprise one or more of a two-dimensional display, e.g. a monitor, heads-up display of an operating microscope, an augmented reality display, a virtual reality display, a three-dimensional display, or a stereoscopic image display, e.g. with depth perception.

The microscope may comprise a binocular surgical operating microscope, for example. The system 400 may comprise an endoscope 1530 that is delivered in situ along with the treatment probe 23 to provide imaging of one or more target locations before, during, or after the procedure. The endoscope 1530 of the probe 23 may comprise any suitable imaging device, and in some cases, may comprise one or more optical fibers, such as a fiber optic array. A lens may focus light onto the one or more optical fibers which convey the imaging data from within the eye to the endoscope input 1501. A detector array may be positioned within the endoscope input, in a handpiece of the system, or anywhere within the system to receive the light conveyed by the one or more optical fibers and convert the light into imaging data. In some embodiments, the detector array may be a CCD or CMOS imaging sensor located outside the eye of the patient, and may be contained within an endoscope handpiece, in the endoscope input 1501, or within the controlling unit 410. Images conveyed by the endoscope and captured by the detector array may be processed by an image processing apparatus 412 of the controlling unit 410 to generate a plurality of augmented images visualized by the physician in real time.

The augmented images can be shown on a display of the heads up display 407, and combined with optical images from the microscope with an internal beam splitter 708 to form monocular or binocular images as is known to one of ordinary skill in the art. As described herein, a microscope view may comprise one or more of an optical microscope image, an image from an endoscope placed in the eye, a microscope image and an overlaid virtual image, or a microscope image in combination with imaging captured by the endoscope with or without an overlaid virtual image, for example. When a microscope view includes an overlaid image, the overlaid image can be registered with the microscope image using elements which enable such alignment. Similarly, when the view includes imaging from the endoscope and an overlaid virtual image, the overlaid image can be registered with the imaging from the endoscope using elements which enable such alignment.

The images can be provided to the surgeon in many ways. For example, the surgeon can view the images with an augmented reality display such as glasses or goggles and view the surgical site through the operating microscope. In some embodiments, the surgeon views the images with virtual reality display. Alternatively, or in combination, the eye can be viewed with an external monitor, and the images of the eye viewed with the external monitor with markings placed thereon as described herein. The images viewed by the surgeon may comprise monocular images or stereoscopic images, for example.

According to some embodiments, a surgeon may first view a surgical instrument, such as a probe, in the microscope or a video image from the operating microscope. In some cases, the surgeon may alternatively, or additionally, view images captured by the endoscope showing the probe. According to some embodiments, a surgeon may view images from the microscope and images captured from the endoscope through the oculars of the microscope. Alternatively or in combination, the surgeon may view an augmented image or view, where additional information is overlaid on one or more of the optical microscope image or the endoscope image. When there is an image captured by the endoscope overlaid on the image from the microscope image, the surgeon can view both the microscope image and concurrently the overlaid endoscope image. Furthermore, the image processing apparatus 412 can detect anatomical features of the eye as described herein, and overlay markers onto the microscope image or the endoscope image to help guide a surgeon in identifying and locating these features. The augmented images may be presented to the physician through an eyepiece (or eyepieces) or oculars of the microscope and/or a display of the microscope, and in some embodiments may be viewed on a monitor screen. This may be beneficial to allow a surgeon to maintain a stereoscopic view of an operative site through the oculars of the microscope while simultaneously viewing superimposed or adjacent images or information concurrently either stereoscopically or monocularly, for example. Real-time images captured by the endoscope in situ and real time treatment information can be superimposed to the live view of one or both oculars. In some embodiments, the apparatus and methods disclosed provide a real-time view including real and augmented images from both outside and inside of the anterior chamber during these surgeries.

The optical microscope 409 may be operatively coupled to an endoscope inserted into the eye in many ways. The optical microscope 409 may comprise a binocular microscope such as a stereo-microscope comprising imaging lens elements to image an object onto an eyepiece(s) comprising an ocular 408. The endoscope placed in the eye is configured to capture optical images of the eye. The optical images may be transmitted to the controlling unit 410 for processing. The endoscope placed in the eye may comprise optical elements (e.g., lens, mirrors, filters, prisms, etc.). The endoscope may capture color images, greyscale images and the like, and may be introduced with the probe and moved with the probe, or the probe may move independently of the endoscope while maintaining rotational alignment with the probe. In some instances, the probe and the endoscope move together during insertion to a location of interest, and then the probe or the endoscope can move independently of the other while maintaining rotational alignment.

Although reference is made to the endoscope and treatment probe 500 inserted through the same incision, in some embodiments the endoscope and treatment probe 500 are inserted through different incisions with the endoscope placed to image the target tissues. For example, the imaging probe can be inserted through a first incision and the treatment probe 500 inserted through a second incision and vice versa.

The endoscope images may be acquired at an appropriate image frame resolution. The image frame resolution may be defined by the number of pixels in a frame. The image resolution of the detector that receives light transmitted by one or more optical fibers of a fiber optic array of the endoscope placed in the eye may comprise any of the following resolutions: 160×120 pixels, 249×250, 250×250, 320×240 pixels, 420×352 pixels, 480×320 pixels, 720×480 pixels, 1280×720 pixels, 1440×1080 pixels, 1920×1080 pixels, 2048×1080 pixels, 3840×2160 pixels, 4096×2160 pixels, 7680×4320 pixels, or 15360×8640 pixels. The resolution of the array detector coupled to the endoscope may comprise a resolution within a range defined by any two of the preceding pixel resolutions, for example within a range from 160×120 pixels to 250×250 pixels, e.g. 249×250 pixels. The imaging device may have a pixel size smaller than 1 micron, 2 microns, 3 microns, 5 microns, 10 microns, 20 microns and the like. The detector array may have a footprint on the order of 2 mm×2 mm, or 1 mm×1 mm, 0.8 mm×0.8 mm, or smaller, or any other desirable size to detect light transmitted by the fiber optic array.

The images from the endoscope may comprise a sequence of image frames captured at a specific capture rate. In some embodiments, the sequence of images may be captured at standard video frame rates such as about 24p, 25p, 30p, 43p, 48p, 50p, 60p, 62p, 72p, 90p, 100p, 120p, 300p, 50i or 60i, or within a range defined by any two of the preceding values. In some embodiments, the sequence of images may be captured at a rate less than or equal to about one image every 0.0001 seconds, 0.0002 seconds, 0.0005 seconds, 0.001 seconds, 0.002 seconds, 0.005 seconds, 0.01 seconds, 0.02 seconds, 0.05 seconds, or 0.1 seconds. In some cases, the capture rate may change depending on user input and/or external conditions under the guidance of the control unit 410 (e.g. illumination brightness).

The images captured by the endoscope may be captured in real time, such that images are produced with reduced latency, that is, with negligible delay between the acquisition of data and the rendering of the image. Real time imaging allows a surgeon the perception of smooth motion flow that is consistent with the surgeon's tactile movement of the surgical instruments (e.g. the elongate probe and the probe tip) during surgery. Real time imaging may include producing images at rates faster than 30 frames per second (fps) to mimic natural vision with continuity of motion, and at twice that rate to avoid flicker (perception of variation in intensity). In some embodiments, the latency may comprise a time interval from capturing the images from the endoscope until information is shown to the user, which may be no more than about 100 ms, for example 50 ms or less. In some embodiments, the latency comprises no more than one or two frames of the image shown on the display. In some instances, the terms "endoscope" and "fiberscope" may be used interchangeably. A fiberscope is a flexible optical fiber bundle that can be used to view or capture images by transmitting light from a distal end of the optical fiber bundle, through total internal reflection, to a location at a proximal end of the optical fiber bundle. In some instances, a detector array can be positioned at the proximal end of the optical fiber bundle to capture imaging data corresponding to a location near the distal end of the optical fiber bundle. In some instances, the endoscope may include an imaging bundle, an illumination bundle, one or more energy delivery bundles, or any combination.

In some embodiments, the optical microscope 409 may be coupled to an electronic display device 407. The electronic display 407 may comprise a heads-up display device (HUD). The HUD may or may not be a component of the microscope system 409. The HUD may be optically coupled into the field-of-view (POV) of one or both of the oculars. The display device may be configured to project augmented images from input 507 generated by the controlling unit 410 to a user or surgeon. The display device 407 may alternatively or additionally be configured to project images captured by the endoscope to a user or surgeon. The display device may be coupled to the microscope via one or more optical elements such as beam-splitter or mirror 420 such that a physician looking into the eyepieces 408 can perceive in addition to the real image, endoscope imaging, augmented images, or any combination represented and presented by the display device 407. The display device may be visible through a single ocular to the surgeon or user. Alternatively, the HUD may be visible through both eyepieces 408 and visible to the surgeon as a stereoscopic binocular image combined with the optical image formed with components of the microscope, for example.

The display device of heads up display 407 is in communication with the controlling unit 410. The display device may provide augmented images produced by the controlling unit 410 in real-time to a user. As described herein, real time imaging may comprise capturing the images with no substantial latency and allows a surgeon the perception of smooth motion flow that is consistent with the surgeon's tactile movement of the surgical instruments during surgery. In some cases, the display device 407 may receive one or more control signals from the controlling unit for adjusting one or more parameters of the display such as brightness, magnification, alignment and the like. The image viewed by a surgeon or user through the oculars or eyepieces 408 may be a direct optical view of the eye, images displayed on the display 407 or a combination of both. Therefore, adjusting a brightness of the images on the HUD may affect the view of the surgeon through the oculars. For instance, processed information and markers shown on the display 407 can be balanced with the microscope view of the object. The processor may process the endoscope image data, such as to increase contrast of the image data so the visible features are more readily detectable or identifiable.

The heads up display 407 may be, for example, a liquid crystal display (LCD), a LED display, an organic light emitting diode (OLED), a scanning laser display, a CRT, or the like as is known to one of ordinary skill in the art.

Alternatively or in combination, the display 407 may comprise an external display. For example, the display 407 may not be perceivable through the oculars in some embodiments. The display 407 may comprise a monitor located in proximity to the optical microscope. The display 407 may comprise a display screen, for example. The display 407 may comprise a light-emitting diode (LED) screen, OLED screen, liquid crystal display (LCD) screen, plasma screen, or any other type of screen. The display device 407 may or may not comprise a touchscreen. A surgeon may view real-time optical images of the surgical site and imaging provided by the in-situ endoscope simultaneously from the display 407.

The endoscope inserted into the eye may comprise a fiber optic array suitable for capturing imaging at a resolution for viewing tissue structures of the eye as described herein and may provide images having a resolution within a range from less than 1 to 10 microns, for example within a range from about 3 to 6 microns, for example. In some embodiments, the endoscope may have a spatial resolution within a range from about 10 μm to about 80 μm for tissue adjacent tissue contacting the inclined distal end of the probe and optionally wherein the resolution is within a range from about 20 μm to about 40 μm.

In some embodiments, lights that are present for the operating microscope provide sufficient illumination. In some embodiments, the endoscope placed in the eye may optionally comprise a light source suitable for producing images having suitable brightness and focus. In some embodiments, the endoscope placed in the eye may comprise a light-emitting diode (LED), one or more optical fibers for illumination such as an illumination bundle, or MicroLED. In some embodiments, one or more color filters can be applied to the imaging captured by the endoscope in order to help isolate, locate, or otherwise identify tissue structures of interest. The endoscope placed in the eye may be at least partially controlled by the controlling unit. Control of the endoscope by the controlling unit may include, for example, activation of the detector array for capturing images, controlling illumination, parameters setup, focus, brightness, contrast, application of one or more filters, or customizable control parameters.

The endoscope placed in the eye may be coupled to an image sensor having a high signal to noise ratio. The endoscope may comprise a lens and a fiber optic array coupled to a sensor array, or detector array. In some embodiments, one or more lenses of the endoscope comprises borofloat glass, for example. The sensor array may have any suitable number pixels arranged in a row and column array. In some embodiments, the pixel array comprises 249×250 pixels, which may comprise rolling shutter pixels, for example. In some embodiments, the pixels have a pitch of 3 μm, which results in an optical area of 1.06 mm diameter, for example.

The system 400 may further comprise a user interface 413. The user interface 413 may be configured to receive user input and output information to a user. The user input may be related to control of a surgical tool such as the probe 23. The user input may be related to the operation of the optical microscope (e.g., microscope settings, image acquisition, etc.). The user input may be related to various operations or settings about the image capture system. For instance, the user input may include a selection of a target location, a selection of a treatment reference marker, displaying settings of an augmented image, customizable display preferences and the like. The user interface may include a screen such as a touch screen and any other user interactive external device such as handheld controller, mouse, joystick, keyboard, trackball, touchpad, button, verbal commands, gesture-recognition, attitude sensor, thermal sensor, touch-capacitive sensors, foot switch, or any other device.

In some embodiments, the endoscope placed in the eye is used for guiding the probe 23 and visualization of the target site. In some embodiments, the endoscope can be configured to view tissue and the probe tip. In some embodiments, the lens of the endoscope is located at a distance of about 10 mm from the probe tip, for example at least about 6 mm from the probe tip. These distances allow the probe tip to be seen on the endoscope image to target Schlemm's canal.

The controlling unit 410 may be configured to generate an augmented layer comprising the augmented information. The augmented layer may be a substantially transparent image layer comprising one or more graphical elements. The terms "graphical element" and "graphical visual element" may be used interchangeably throughout this application. The augmented layer may be superposed onto the optical view of the microscope, optical images or video stream, and/or displayed on the display device. The transparency of the augmented layer allows the optical image to be viewed by a user with graphical elements overlay on top of it. In some embodiments, the augmented layer may comprise real time endoscope images or other information obtained by one or more of the endoscope placed in the eye or camera 416.

As described herein, the fusing of the optical microscopic image data, the endoscope image data, the augmented information, or any combination, may comprise incorporating the augmented information into the optical microscopic image or the endoscope image data, or both. The augmented image data may comprise one or more graphical elements associated with the depth information, target location, orientation information, tissue identification information, or various other supplemental information. The graphical elements may be overlaid onto the optical microscopic image and/or the endoscope image with a beam splitter 708, for example. A graphical element can be directly overlaid onto an image of any object visible in the optical microscopic image. A graphical element may also include any shape, boundary, or contour surrounding an image of any object in the optical microscopic image. The object may be, for example, an instrument inserted into the eye (e.g., probe), a portion of the probe, target tissues as described herein, and the like.

Figure 16:
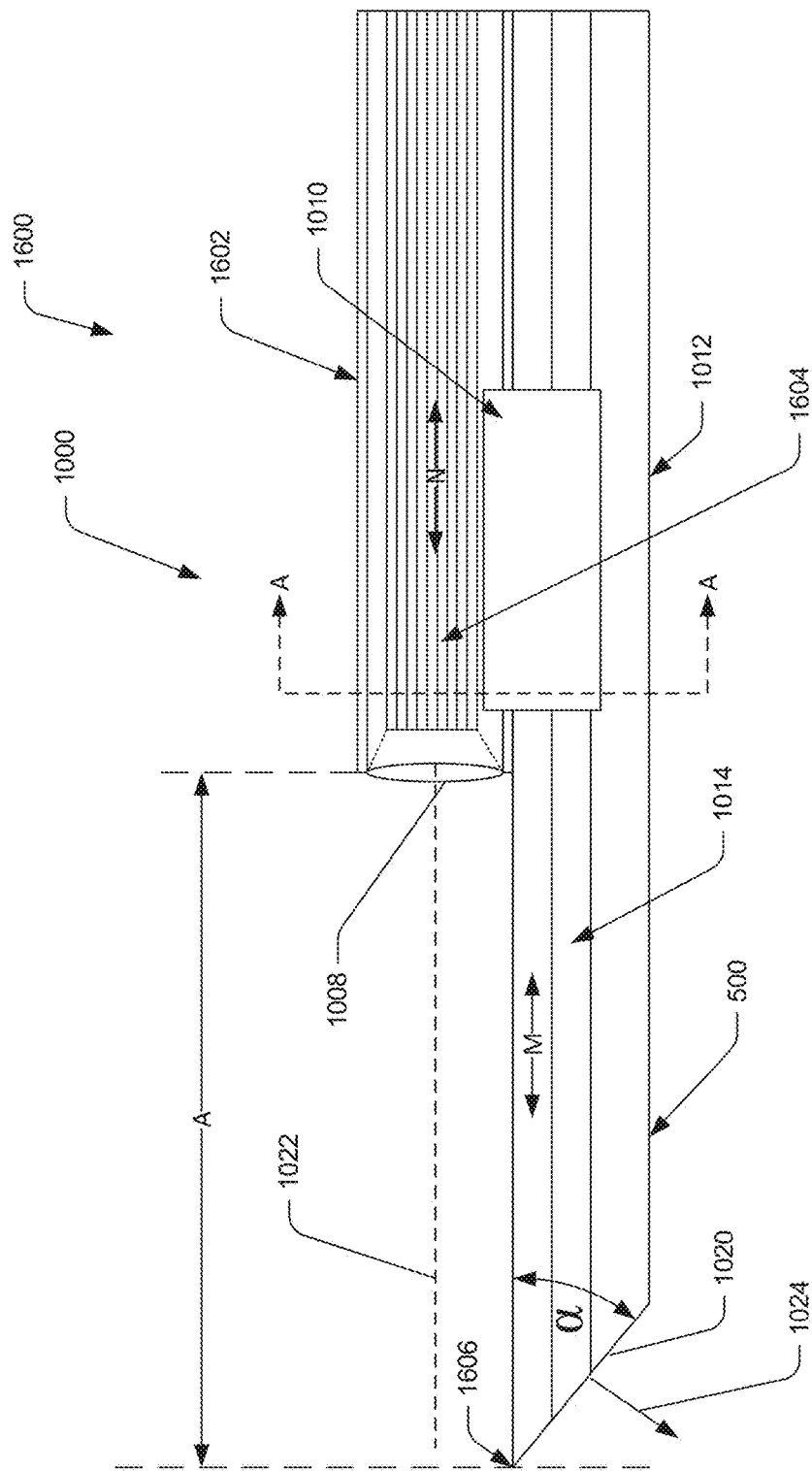
FIG. 16 shows an example of a treatment probe and a fiber optic array coupled to each other with a fastener, in accordance with some embodiments.

With reference to FIG. 16 an example treatment probe 500 and endoscope 1600 are illustrated in accordance with some embodiments. The endoscope 160 is contained within an endoscope housing 1602 and comprises a lens 1008 and a fiber optic array 1604. As described elsewhere herein, a detector array that receives light from the fiber optic array 1604 may comprise an array with any suitable resolution for example of within a range from 200×200 to 300×300 pixels, for example.

A fastener 1010 such as a clip may be used to couple the endoscope housing 1602 to a treatment optical fiber housing 1012. The treatment optical fiber housing 1012 may at least partially enclose a treatment optical fiber 1014 configured to delivery light energy to a treatment site. The optical fiber housing 1012 and the treatment optical fiber 1014 may comprise components of a treatment probe 500 and the endoscope and endoscope housing 1602 may comprise components of an imaging probe. The optical fiber housing 1012 may be configured with one or more structures that cooperate with the fastener 1010 to secure the treatment optical fiber housing 1012 and the endoscope housing 1602 in a fixed relative rotational orientation. In other words, the fastener 1010 may secure the endoscope housing 1602 and the optical fiber housing 1012 together such that neither the endoscope housing 1602 or the optical fiber housing 1012 can rotate substantially about their longitudinal axes independently of the other, for example no more than about 2 degrees. The fastener 1010 may be permanently affixed to either the endoscope housing 1602 or the optical fiber housing 1012 and selectively engage the other. Alternatively, the fastener 1010 may comprise a separate part configured to couple to the treatment probe 500 and the imaging probe 1000.

The distal end 1020 of the treatment probe 500 may be formed with an inclined surface having an angle relative to the longitudinal axis of the treatment probe 500. In some embodiments, the distal end of the treatment probe 500 or the distal end of the treatment optical fiber, or both, are inclined at an angle $\alpha$ of about 45 degrees to about 65 degrees and optionally at an angle $\alpha$ within a range from about 50 degrees to about 60 degrees. In some embodiments, the angle $\alpha$ of the distal end of the treatment probe 500 is substantially the same as the angle $\alpha$ of the distal end of the treatment optical fiber. In some embodiments, the angle $\alpha$ of the distal end of the treatment probe 500 is within 10 or fewer degrees of the angle $\alpha$ of the distal end of the optical fiber.

While the illustrated embodiment shows a single treatment optical fiber 1014, it should be appreciated that a bundle of treatment optical fibers could be used with the disclosed systems and methods. In some examples, the treatment probe 500 comprises a bundle of treatment optical fibers that each have a distal end at or near the angle of the distal end of the treatment probe 500.

In some embodiments, the endoscope housing 1602 can translate along its longitudinal axis in a direction N independently of the treatment optical fiber housing 1012. In some cases, the translation distance of the endoscope housing 1602 is fixed, such that there are limits to the translation distance of the endoscope housing 1602 relative to the treatment optical fiber housing 1012. In some embodiments, the distal end of the probe 1606 extends beyond the lens 1008 of the endoscope by a distance A within a range from about 2 mm to about 10 mm, or within a range from about 2.5 mm to about 5 mm. In embodiments, in which the endoscope can translate independently of the treatment optical fiber housing, the translation distance may be bounded by these dimensions, such that the lens of the endoscope can be moved to about 2 mm to about 10 mm from the distal end of the optical fiber housing. The travel limits may be provided by any suitable structure or mechanism, such as slots, grooves, protrusions, bosses, stops, and the like.

The treatment probe 500 may be translated in a direction M, and the endoscope housing 1602 may be secured to the treatment probe 500 such that the endoscope housing 1602 is translated along with the treatment probe 500. In some embodiments, the endoscope housing 1602 may selectively have a rigid attachment to the optical fiber housing 1012 that can be released to provide a degree of freedom for translating along its longitudinal axis within translational limits, as described herein.

In some embodiments, the endoscope 1600 of the imaging probe 1000 comprises an optical axis 1022. The optical axis 1022 may extend approximately parallel to an elongate axis of the treatment optical fiber 1014, for example parallel to within about 5 degrees. In some embodiments, the treatment optical fiber 1014 comprises an inclined distal 1020 end as described herein. The imaging fiber optic array 1604 may include individual fiber optics that are each aligned with the inclined distal end 1020 of the treatment probe 500, so that the images from the endoscope 1600 placed in the eye are aligned with the inclined distal end 1020 of the treatment probe 500. The inclined distal end 1020 of the treatment probe 500 may comprise a substantially flat surface that defines a surface normal vector 1024. The endoscope 1600 can be positioned in relation to the surface normal vector 1024 of the treatment probe 500 in many ways. In some embodiments the surface normal vector 1024 of the treatment probe 500 and the optical axis 1022 of the imaging probe 1000 extend along a common plane. In some embodiments, the inclined distal surface 1020 of the treatment probe 500 faces away from the optical axis 1022 of the imaging probe 1000, for example with the surface normal vector 1024 directed away from the optical axis 1022. In alternative embodiments, the inclined distal surface 1020 faces toward the optical axis 1022, for example with the surface normal vector 1024 directed toward the optical axis 1022.

In some embodiments, individual fibers of the imaging fiber optic array 1604 are aligned with the inclined distal end 1020 of the treatment probe 500, such that the imaging fiber optic array 1604 extends in a direction corresponding to the component of the surface normal vector 1024 extending away from the elongate axis of the optical fiber. Alternatively, individual fibers of the imaging fiber optic array 1604 can be rotated relative to the inclined distal end 1020 of the treatment fiber, and a processor can be used to rotate the image shown to the surgeon in order to align the image of the eye from the endoscope placed in the eye with the inclined distal end of the treatment probe 500. Although reference is made to a treatment probe 500 with an optical fiber 1014, the treatment probe 500 may comprise a probe with implants as described herein, and the processor used to rotate the image shown to the surgeon.

In some embodiments, the individual fibers of the imaging fiber optic array 1604 are constrained in their individual rotation about their elongate axes. That is, individual fibers are not free to rotate. This constraint may be helpful for forming and capturing images at the proximal end of the fiber optic array 1604. Additionally, in some embodiments, the imaging fiber optic array 1604 as a whole is constrained from rotating relative to the optical fiber housing 1012, thus helping the imaging provided to the surgeon to represent an accurate orientation of the endoscope housing 1602 relative to the optical fiber housing 1012.

Figure 17:
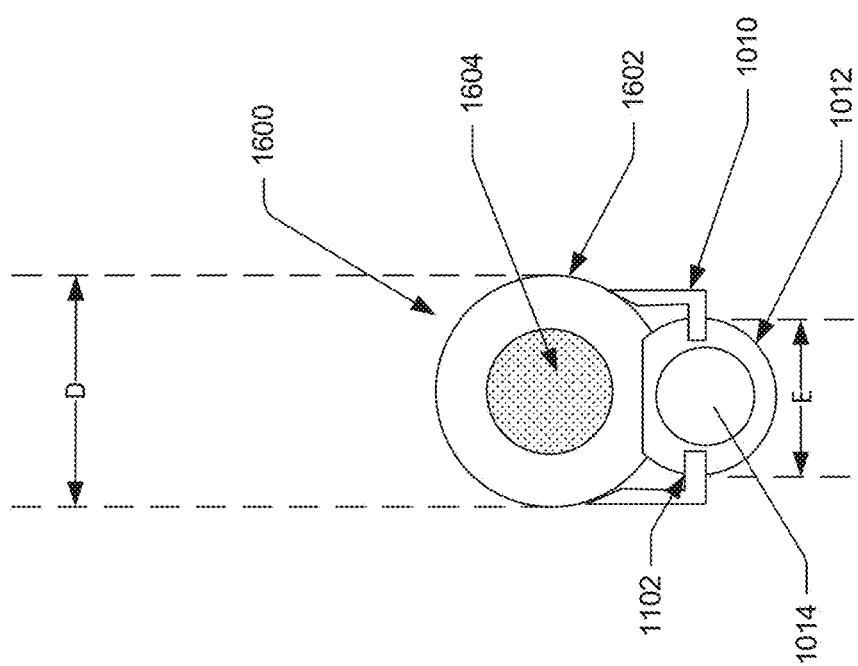
FIG. 17 shows a cross sectional schematic view of an example treatment probe and fiber optic array taken along the line A-A from FIG. 16 in accordance with some embodiments.

FIG. 17 is a cross-sectional schematic view of the probe of FIG. 16 taken along the line A-A. The imaging probe may have an endoscope 1600 comprising a lens 1008 and a fiber optic array 1604. An endoscope housing 1602 may comprise one or more optical fibers, such as the fiber optic array 1604. The treatment optical fiber housing 1012 may be affixed to the endoscope housing 1602 to prevent independent rotation of the endoscope housing 1602 or the optical fiber housing 1012.

According to some embodiments, a fastener 1010 may affix the treatment optical fiber housing 1012 to the endoscope housing 1602. The fastener 1010 may comprise a clip which may be secured in a longitudinal groove of the treatment optical fiber housing 1012. In some embodiments, the clip is affixed to the endoscope housing 1602 and comprises an engagement structure such as, for example, a flat engaging surface, a slot, a key, a groove, an aperture, a protrusion, or other suitable structure. In some embodiments, the clip couples the treatment optical fiber housing 1012 to the endoscope housing 1602 with a fixed angular orientation.

In some embodiments, the endoscope housing 1602 or the treatment optical fiber housing 1012, or both, have flat engaging surfaces to provide intimate surface contact between the endoscope housing 1602 and the optical fiber housing 1012, and to orient the optical fiber housing 1012 for receiving the fastener.

In some embodiments, the endoscope housing 1602 has a maximum dimension D to allow the endoscope housing 1602 the be inserted into the eye of a patient, which may be within the range of about 0.8 mm to about 1.2 mm. The treatment optical fiber housing 1012 may have a maximum cross-sectional dimension E within the range of from about 300 μm to about 600 μm, and in some embodiments, the dimension E is smaller than the dimension D. While the endoscope housing 1602 and the treatment optical fiber housing 1012 are represented schematically as having a generally cylindrical cross section, the respective housings may have any suitable cross-sectional shape, such as ovoid, hexagonal, octagonal, circular, or any suitable shape.

In some embodiments, the fastener 1010 may comprise a clip or an aperture to engage one or more of the endoscope housing 1602, the inserter housing 1215, or the treatment optical fiber housing 1012 and optionally the clip comprises the engagement structure sized and shaped to receive the endoscope housing, the inserter housing 1215, the optical fiber housing, or a combination.

The fastener 1010 may allow the endoscope housing 1602 to slide in relation to the inserter housing 1215 or the treatment optical fiber housing 1012 while the rotational orientation of the endoscope 1600 to the inserter housing 1215 or the optical fiber housing 1012 remains fixed.

The imaging probe comprising the endoscope 1600 may be fastened to the treatment probe 500 with the fastener, such that the rotational orientation of the endoscope relative to the rotational orientation of the instrument is fixed, that is, the endoscope 1600 cannot substantially rotate independently of the treatment probe 500, e.g. more than five degrees, for example no more than two degrees, e.g. no more than one degree. In some embodiments, the rotation orientation is fixed by use of cooperating structures that reduce the likelihood of relative rotation between the endoscope 1600 and the treatment probe 500. In some embodiments, a clip secures the endoscope 1600 to the treatment probe 500 and fixes the rotational orientation, for example prevents the endoscope 1600 from rotating relative to the instrument (e.g., the treatment probe 500). This may be accomplished by any suitable structure or method, but in some examples, is accomplished by one or more clips that fix the rotational of the endoscope relative to the probe. This may also be accomplished by abutting the fiber optic of the instrument against a flat surface of the endoscope 1600. In some embodiments a fastener 1010 couples the inserter housing 1215 or the optical fiber housing 1012 to the endoscope housing 1602 with a fixed angular or rotational orientation. The fastener 1010 may comprise an engagement structure which may be a flat surface, a slot, a key, a keyway, a groove, an aperture, a protrusion, a boss, or some other suitable structure for fixing the orientation of one or more of the optical fiber, the endoscope, or the inserter housing 1215.

In some embodiments, a fastener 1010 comprises a clip that engages the endoscope housing 1602, the inserter housing 1215, or the treatment optical fiber housing 1012 and in some cases, the clip engages with the endoscope housing 1602, the inserter housing 1215, or the optical fiber housing 1012 to provide a fixed orientation. Alternatively or in combination, the fastener comprises an aperture sized and shaped to receive the endoscope housing 1602, the inserter housing 1215, or the treatment optical fiber housing 1012 and to provide a fixed orientation. In some instances, the fastener allows the endoscope housing 1602 to slide relative to the inserter housing 1215 or the optical fiber housing 1012.

In some embodiments, the fastener fixes a distance between the distal end of the treatment probe 500 and the lens of the endoscope 1600. The fastener 1010 may comprise a stop, a pair of stops, an interlocking mechanism, a nesting mechanism, a circumferentially extending channel, a circumferentially extending protrusion, an annular protrusion, an annular recess, or some other suitable structure that provides a stop to limit the relative distance between the distal end of the probe 1606 and the lens 1008 of the endoscope. In some embodiments, a distance between the distal end of the probe 1606 and the lens 1008 are fixed, while in other cases there is relative movement therebetween up to the limits provided by the fastener.

FIG. 16 shows a length of the fastener extending along an elongate direction of the imaging probe and the treatment probe 500. FIG. 17 shows a first direction transverse to the elongate direction of the treatment probe 500 and the imaging probe. The fastener can be sized and shaped to extend around at least a portion of the endoscope housing 1602 and a portion of the inserter housing 1215 as described herein or the treatment optical fiber housing 1012 as described herein. The fastener 1010 may comprise a first distance transverse to the endoscope housing 1602 and the inserter housing 1215 or the optical fiber housing 1012, and a second distance transverse to the endoscope housing and the inserter housing 1215 or the optical fiber housing as shown in FIG. 17. The elongate distance of the fastener may comprise a third distance along an elongate axis of the endoscope housing 1602 and the inserter housing 1215 or the optical fiber housing 1012. In some embodiments, the second distance is less than the first distance, and the third distance is greater than the second distance and the first distance. In some embodiments, the first distance is within a range from about 1.0 mm to about 2 mm, the second distance within a range from about 0.8 to 1.5 mm and the third distance within a range from about 2 mm to about 20 mm, for example. In some embodiments these ranges are smaller, for example the first distance can be within a range from about 1.3 to about 1.7 mm, the second distance can be within a range from about 1.0 to 1.3 mm, and the third distance within a range from about from about 2 mm to about 10 mm. The third distance along the elongate direction can be longer than the first transverse distance and the second transverse distance to add stiffness to the coupling between the imaging probe and the treatment probe 500.

With reference to FIGS. 18A and 18B, an example of a treatment probe 500 and endoscope 1600 enclosed within an integrated housing 1202 is shown, in accordance with some embodiments. The treatment probe 500 comprises an integrated housing 1202 that encloses an optical fiber 1014 and an endoscope 1600. The endoscope 1600 may comprise a lens 1008, a fiber optic array 1604, a detector array, and circuitry to couple the endoscope 1600 to a controlling unit as described herein. The integrated housing 1202 may comprise an aperture to allow a lens 1008 of the endoscope 1600 to view features of interest. An optical axis 1022 extends through the lens 1008 toward the distal end of the probe 1606. The treatment optical fiber 1014 has a distal end that is spaced a distance from the lens 1008, as described herein.

FIG. 18B is a cross-sectional schematic view of the probe of FIG. 18A taken along the line B-B. The integrated housing 1202 has a maximum cross-sectional dimension D that is selected to allow insertion of the probe into the eye to access a treatment location, such as within the anterior chamber of a patient's eye. In some embodiments, the maximum dimension D is within the range of from about 0.5 mm to about 3 mm, or from about 1 mm to about 2 mm, for example In some embodiments, the probe comprises a length within a range from about 10 mm to about 50 mm sized for insertion into the eye. The length of the probe, in some cases, is selected to allow the probe to reach and compress the trabecular meshwork with the inclined distal end within the eye of a patient.

The treatment optical fiber core 1206 and cladding may be encased by an optical fiber housing 1012. The optical fiber housing 1012 may comprise any suitable material, but in some cases is stainless steel. The optical fiber housing 1012 has a maximum cross-sectional dimension E that may be within the range of from about 300 µm to about 600 µm. In some embodiments, the optical fiber housing 1012 has a diameter within a range from about 100 µm to about 300 µm and optionally within a range from about 150 µm to about 250 µm. The endoscope housing 1602 may comprise a maximum cross-sectional dimension within the range of from about 0.8 mm to about 1.2 mm. As shown in FIG. 12B, in some embodiments, the integrated housing 1202 encloses both the endoscope 1600 and the treatment optical fiber 1014 and may comprise any suitable cross-sectional shape and size. In some embodiments, the integrated housing 1202 is sized and shaped to deliver the endoscope 1600 and optical fiber 1014 to the anterior chamber of a patient's eye, and more specifically, deliver the optical fiber 1014 toward the trabecular meshwork to deliver laser energy to the trabecular meshwork. In some embodiments the treatment optical fiber 1014 comprises an inclined distal end 1020 to uniformly comprise the trabecular meshwork to form one or more openings into Schlemm's canal.

Figure 19:
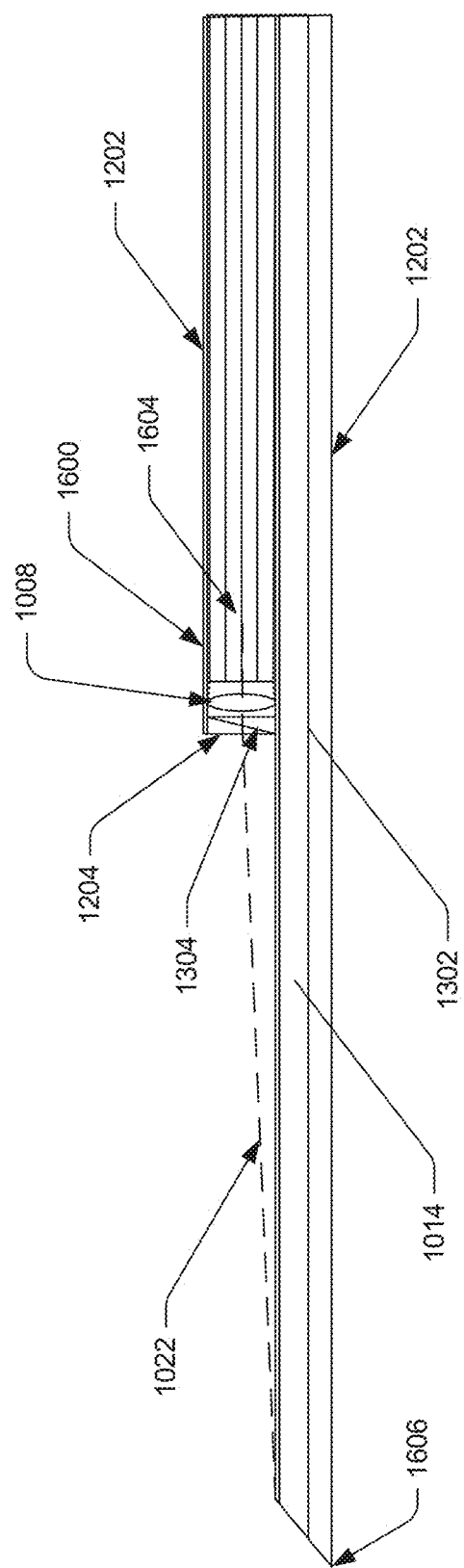
FIG. 19 shows an example of a treatment probe and a fiber optic array in accordance with some embodiments.

FIG. 19 shows a probe comprising an optical axis 1022 inclined relative to an elongate axis of the treatment probe 500. The inclined optical axis 1022 can decrease movement of out of focus tissue as the probe is advanced toward the target location, and may facilitate movement of the treatment probe 500 toward the target tissue. Although the treatment probe 500 is shown having an integrated housing 1202 that comprises an endoscope 1600 and a treatment optical fiber 1014, the treatment optical fiber 1014 and endoscope 1600 can be coupled to each other with a fastener as described herein, so as to incline the optical axis 1022 in relation to the distal end of the probe 1606. The inclined optical axis 1022 can be combined with the implant placement devices as described herein. For example, the optical axis 1022 can be oriented toward the distal tip of the implant placement probe or the implant on the distal end of the probe.

In some embodiments, a prism 1304 is located along the optical path to deflect the optical axis 1022. The prism 1304 may comprise a discrete optical element located along the optical path with the lens. Alternatively the prism 1304 may be located on a surface of the lens 1008. In some embodiments, the lens 1008 comprises a wedge in order to deflect light along the optical path 1022. In some embodiments, the lens 1008 comprises an eccentric lens with prism 1304 to deflect the optical axis 1022.

In some embodiments, the inclined optical axis 1022 of the lens 1008 may allow the endoscope 1600 to image an implant carried by the integrated housing 1202 with the implant approximately centered in the endoscope image. Alternatively or in combination, the inclined optical axis 1022 may allow the endoscope 1600 to image the distal tip 1606 of the treatment optical fiber 1014 or its housing approximately to be approximately centered in the image, in order to allow the surgeon to use the distal tip 1606 to aim the probe at the treatment site. In some embodiments, the endoscope 1600 is slidable relative to the integrated housing 1202, and the optical axis 1022 can thereby be moved, so as to pass through the distal tip 1606 of the optical fiber 1014 or beyond. For example, the imaging probe can be coupled to the treatment probe 500 with a slidable fastener as described herein. Alternatively, the endoscope 1600 can be slidable relative to the probe 500 within the integrated housing.

Figure 20:
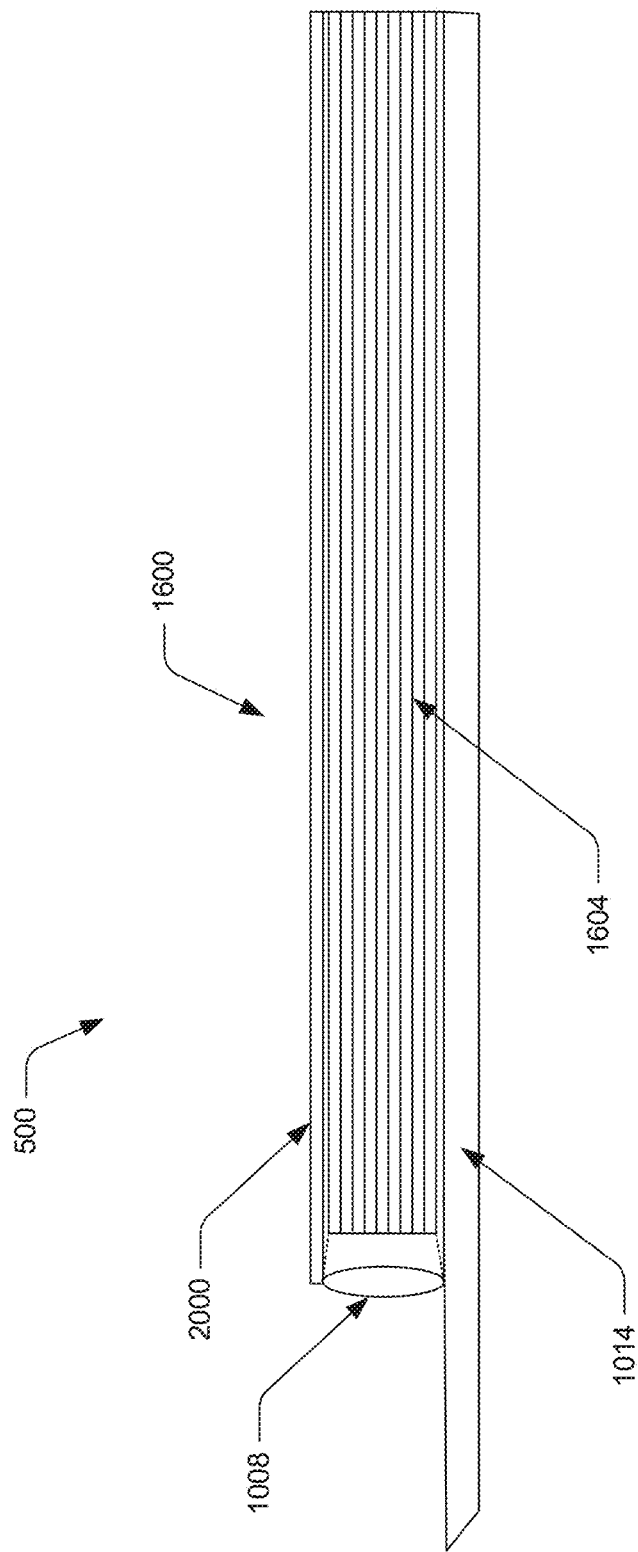
FIG. 20 shows an example of a treatment probe and a fiber optic array in accordance with some embodiments.

FIG. 20 shows a probe 500 comprising one or more illumination optical fibers, comprising an illumination bundle 2000. In some embodiments, the one or more of illumination optical fibers comprises a plurality of fiber bundles. For example, a probe may comprise fiber bundles corresponding to an illumination bundle 2000, a fiber optic array, and an optical fiber. Each of these devices may be formed of one or more optical fibers used to transmit light through total internal reflection. The fibers used with any embodiment described herein may individually be formed of any suitable material, such as glass, quartz, fused silica, or plastic for example. The optical fibers may comprise a core surrounded by transparent cladding material with a lower index of refraction and are designed to transmit light that enters one end of the optical fibers to a second end of the fibers. For example, the proximal end of some of the fibers may be coupled to a light source and used to provide illumination to the distal end of the treatment probe 500, while other fibers may be used to transmit light from the treatment site within a patient to a detector array that captures the light and generates a digital image. In some cases, one or more of the optical fibers is connected to an energy source and may be used to transmit laser energy to the treatment site.

The illumination bundle 2000 may comprise one or more illumination optical fibers that are used to deliver light to the treatment site to provide illumination for imaging purposes. The fiber optic array 1604 may comprise one or more optical fibers that are used to transmit light from the treatment site, to a detector array that creates digital images of the treatment site which can be provided to a user or surgeon as described herein. A lens 1008 may focus light onto the distal ends of individual fibers that make up the fiber optic array 1604. An optical fiber 1014, or a bundle of optical fibers, may be used to deliver energy, such as for cutting, resecting, cauterizing, or some other purpose at a treatment site. The illumination bundle 2000, fiber optic array 1604, and optical fiber 1014 may be disposed within a common housing and configured to be delivered to a treatment site, such as within an eye of a patient.

The illumination bundle 200 may be disposed within a common housing with the fiber optic array 1604. Alternatively or additionally, the illumination bundle 2000 may be disposed within a common housing with the optical fiber 1014. In some cases, an illumination bundle 2000 may provide illumination from various locations of the treatment probe 500 or the imaging probe or both.

A housing as described herein may enclose the treatment optical fiber 1004, the endoscope 1600 and the one or more illumination optical fibers and may further fix a rotational orientation between the endoscope 1600, the treatment optical fiber 1004 and the one or more illumination optical fibers 2000. The endoscope may include an ordered arrangement of a bundle of fibers. In some cases, the ordered arrangement of the bundle of fibers is maintained from the distal end of the bundle of fibers to the proximal end of the bundle of fibers. In some instances, the ordered arrangement remains consistent at the distal end and the proximal end of the bundle of fibers, and in some cases, does not maintain the ordered arrangement at a location between the distal end and the proximal end. The ordered arrangement of the bundle of fibers allows light entering the distal end of the bundle of fibers to maintain an orientation to preserve an orientation of an image captured at the proximal end of the bundle of fibers, such as by a detector array.

In some embodiments, an imaging system is delivered to a treatment site within a patient, such as within an eye of a patient. The imaging system may include components that are disposed within the patient and additionally or alternatively include components that are outside the patient. A camera is an example of an imaging system. A camera may be positioned at a treatment site within a patient as described herein. An endoscope is another example of an imaging system. Some components of the endoscope, such as a lens and a distal end of a fiber bundle, may be located at a treatment site, while other components of the endoscope, such as a detector array and a proximal end of the fiber bundle, may be located remotely from the treatment site, such as, for example, outside the patent. The imaging system may be coupled to the apparatus for eye surgery as described herein, which may be a wired or wireless connection.

The present disclosure includes the following numbered clauses, which are part of the present disclosure. Each clause can be combined with one or more other clauses to the extent that such a combination is consistent with the teachings disclosed herein.

Clause 1. An apparatus to treat an eye, comprising: a probe sized for insertion into the eye, the probe comprising a camera comprising a lens and an array detector, the array detector comprising a plurality of rows and columns; an implant located near a distal end of the probe, the implant comprising a distal portion sized and shaped for insertion into Schlemm's canal; and a processor coupled to the array detector, the processor configured with instructions to determine a location of Schlemm's canal in response to an image of one or more of a ciliary body band, a scleral spur, or a Schwalbe's line of the eye.

Clause 2. An apparatus to treat an eye, comprising: a probe sized for insertion into the eye, the probe comprising a camera comprising a lens and an array detector, the array detector comprising a plurality of rows and columns; an implant located near a distal end of the probe, the implant comprising a distal portion sized and shaped for insertion into a Schlemm's canal of the eye, the distal portion extending along an elongate insertion axis, the distal end coupled to the camera with a fixed rotational orientation relative to the inclined distal end of the fiber; and a processor coupled to the array detector, the processor configured with instructions to determine an angular orientation of the elongate insertion axis in response to an image of one or more of a ciliary body band, a scleral spur, or a Schwalbe's line of the eye.

Clause 3. An apparatus to treat an eye, comprising: a probe sized for insertion into the eye, the probe comprising an optical fiber and a camera, the camera comprising a lens and an array detector, the array detector comprising a plurality of rows and columns; and a processor coupled to the array detector, the processor configured with instructions to determine a location of Schlemm's canal in response to an image of one or more of a ciliary body band, a scleral spur, or a Schwalbe's line of the eye.

Clause 4. An apparatus to treat an eye, comprising: a laser; a probe comprising a camera and an optical fiber, the camera comprising a lens and an array detector, the array detector comprising a plurality of rows and columns, the optical fiber coupled to the laser, the optical fiber comprising an inclined distal end and a proximal end, the distal end coupled to the camera with a fixed rotational orientation relative to the inclined distal end of the fiber; and a processor coupled to the array detector, the processor configured with instructions to determine an angular orientation of the inclined distal end of the fiber in response to an image of one or more of a ciliary body band, a scleral spur, or a Schwalbe's line of the eye.

Clause 5. The apparatus of any one of clauses 6 or 9, wherein the processor is configured to display the angular orientation of the inclined distal end of the fiber in relation to the distal end on a heads up display of an operating microscope.

Clause 6. The apparatus of any one of clauses 6 or 9 wherein the angular orientation of the inclined distal end comprises one or more a rotation angle around an elongate axis of the probe or a rotation angle around an elongate axis of the camera.

Clause 7. The apparatus of any one of clauses 2, 6, 8 or 9, wherein the processor is configured with one or more of a convolutional neural network, a machine learning algorithm or an edge detection algorithm to identify the one or more of the ciliary body band or the scleral spur and determine the angular orientation.

Clause 8. The apparatus of any one of clauses 2, 6, 8 or 9, wherein the processor is configured with instructions to display a boundary of the ciliary body band on a display and optionally wherein the boundary of the ciliary body band is shown with a plurality of markers located along a curved line.

Clause 9. The apparatus of any one of clauses 2, 6, 8 or 9, wherein the processor is configured with instructions to display a boundary of the scleral spur on a display and optionally wherein the boundary of the scleral spur is shown with a plurality of markers located along a curved line.

Clause 10. The apparatus of any one of clauses 2, 6, 8 or 9, wherein the image on the array detector comprises an image of Schwalbe's line and the processor is configured with instructions to determine a location of Schwalbe's line in response to the image.

Clause 11. The apparatus of any one of clauses 2, 6, 8 or 9, wherein the image on the array detector comprises a visible image of Schlemm's canal, and the processor is configured with instructions to determine a location of Schlemm's canal in response to the visible image of Schlemm's canal and optionally wherein the visible image of Schlemm's canal comprises a contrast of greater than 5 percent (%).

Clause 12. The apparatus of any one of clauses 2, 6, 8 or 9, wherein the processor is configured with instructions to determine a location of Schlemm's canal in response to the one or more of the ciliary body band or the scleral spur and to display the location on a subsequent image from the detector array.

Clause 13. The apparatus of any one of clauses 2, 6, 8 or 9, wherein the probe comprises a maximum dimension across within a range from 0.5 mm to 3 mm and optionally within a range from 1 mm to 2 mm.

Clause 14. The apparatus of clause 20, wherein the probe comprises the maximum cross-sectional dimension over a longitudinal distance within a range from 10 mm to 50 mm, to access a trabecular meshwork of the eye and compress the trabecular meshwork with the inclined distal end.

Clause 15. The apparatus of clause 2, further comprising an inserter housing and a camera housing enclosing the camera with the fixed rotational orientation, the inserter housing enclosing one or more one or more movable components coupled to the implant.

Clause 16. The apparatus of clause 6, further comprising an inserter housing and a camera housing enclosing the camera with the fixed rotational orientation, the inserter housing enclosing one or more one or more movable components coupled to the implant.

Clause 17. The apparatus of clause 8, further comprising an optical fiber housing enclosing the optical fiber and a camera housing enclosing the camera with the fixed rotational orientation.

Clause 18. The apparatus of clause 9, further comprising an optical fiber housing enclosing the optical fiber and a camera housing enclosing the camera with the fixed rotational orientation.

Clause 19. The apparatus of claim any one of clauses 16, 17, or 18, further comprising a fastener to couple the inserter housing or the optical fiber housing to the camera housing with the fixed angular orientation structure, wherein the one or more of the fastener, the inserter housing, the optical fiber housing, or the camera housing comprises an engagement structure to fix the angular orientation and optionally wherein the structure comprises one or more of flat engaging surface, a slot, a key, a groove an aperture or a protrusion and optionally wherein the angular orientation comprises a fixed orientation and the fastener comprises the engagement structure.

Clause 20. The apparatus of clause 19, wherein the fastener comprises one or more of a clip or an aperture to engage one or more of the camera housing, the inserter housing, or the optical fiber housing and optionally wherein the clip comprises the engagement structure sized and shaped to receive the one or more of the camera housing, the inserter housing, or the optical fiber housing and optionally wherein fastener comprises the aperture with the aperture sized and shaped to receive the one or more of the camera housing, the inserter housing or the optical fiber housing with the fixed orientation.

Clause 21. The apparatus of clause 19, wherein the fastener is configured to allow the camera housing to slide in relation to the inserter housing or the optical fiber housing while the orientation of the of the camera to the inserter housing or the optical fiber housing remains fixed and optionally wherein the engagement structure comprises one or more elongate engagement structures to maintain the angle while the camera housing slides in relation to the inserter housing or the optical fiber housing and optionally wherein the elongate engagement structures comprises one or more of one or more axially elongate grooves, one or more axially elongate flat surfaces or one or more axially elongate protrusions.

Clause 22. The apparatus of clause 19, wherein the fastener is configured to fix a distance between the distal end of the probe and the array detector and optionally wherein the engagement structure comprises one or more of a stop, a pair of stops, an interlocking mechanism, a nesting mechanism, a circumferentially extending channel, a circumferentially extending protrusion, an annular protrusion or an annular recess.

Clause 23. The apparatus of clause 19, wherein the camera housing comprises a maximum distance across within a range from about 0.8 to 1.2 mm, the optical fiber housing comprises a maximum distance across within a range from about 300 um to about 600 um, the fastener sized and shaped to extend around at least a portion of the camera housing and a portion of the inserter housing or the optical fiber housing, wherein the fastener comprises a first distance transverse to the camera housing and the inserter housing or the optical fiber housing, a second distance transverse to the camera housing and the inserter housing or the optical fiber housing, and a third distance along an elongate axis the camera housing and the inserter housing or the optical fiber housing, the second distance less than the first distance, the third distance greater than the second distance and the first distance.

Clause 24. The apparatus of clause 23, wherein the first distance within a range from about 1.0 mm to about 2 mm, the second distance within a range from about 0.8 to 1.5 mm, the third distance within a range from about 2 mm to about 20 mm, the first distance optionally within a range from about 1.3 to about 1.7 mm, the second distance optionally within a range from about 1.0 to 1.3 mm, the third distance optionally within a range from about from about 2 mm to about 10 mm.

Clause 25. The apparatus of clause 9, further comprising a housing to enclose the optical fiber and the camera, the housing comprising an inclined distal end.

Clause 26. The apparatus of clause 25, wherein the inclined distal end of the housing extends circumferentially around at least a portion of the inclined distal end of the optical fiber.

Clause 27. The apparatus of clause 25, wherein the inclined distal end of the housing and the inclined distal end of the optical fiber are inclined at an angle to within about 10 degrees of each other and optionally wherein the inclined distal ends comprise flush surfaces.

Clause 28. The apparatus of clause 25, wherein the detector array comprises a side with a flat edge, and the optical fiber extends along the side with flat edge of the detector array.

Clause 29. The apparatus of any one of the preceding clauses, wherein the array detector comprises a number of pixels along a column within a range from about 200 pixels to about 500 pixels and a plurality of pixels along a row within a range from about 200 pixels to about 500 pixels and optionally wherein the number of pixels along the row is within a range from about 200 to 300 pixels and the number of pixels along the column is within a range from about 200 pixels to about 300 pixels.

Clause 30. The apparatus of anyone of the preceding clauses wherein the camera provides a spatial resolution within a range from about 10 um to about 80 um for tissue adjacent tissue contacting the inclined distal end of the probe and optionally wherein the resolution is within a range from about 20 um to about 40 um.

Clause 31. The apparatus of claim anyone of the preceding clauses, wherein the distal end of the probe extends beyond a distal most lens of the camera by a distance within a range from about 2 mm to about 10 mm and optionally within a range from about 2.5 mm to about 5 mm.

Clause 32. The apparatus of claim anyone of the preceding clauses, wherein the distal end of the probe extends beyond a distal most lens of the camera by a distance within a range from about 2 mm to about 10 mm and optionally within a range from about 2.5 mm to about 5 mm and optionally wherein the distance is dimensioned to visualize a portion of the distal end of the probe in the image of the one or more of ciliary body band or the scleral spur.

Clause 33. The apparatus of claim anyone of the preceding clauses, wherein the array detector is located a distance from the distal end of the probe, the distance within a range from about 2.5 mm to about 10.5 mm and optionally within a range from about 3 mm to about 6 mm.

Clause 34. The apparatus of claim any one of the preceding clauses, wherein the inclined end comprises an inclined surface to contact a trabecular meshwork of the eye, and wherein the inclined end comprises a surface normal vector pointing in a direction away from the camera and wherein one or more of the rows or the columns is aligned with a transverse component of the surface normal vector to within about 5 degrees and optionally wherein the transverse component of the surface normal vector extends in a direction transverse to the optical fiber.

Clause 35. The apparatus of claim any one of the preceding clauses, wherein the optical fiber comprises an elongate axis of the optical fiber, the elongate axis extending along a direction of light propagation along the optical fiber, and wherein the inclined distal end traverses the axis at an angle within a range from about 45 degrees to about 65 degrees an optionally wherein the angle is within a range from about 50 degrees to about 60 degrees.

Clause 36. The apparatus of any one of the preceding clauses, further comprising a rotational angle between the distal end of the probe and one or more of the rows or columns of the detector array and wherein the processor is configured with instructions to determine the angle between the elongate insertion axis or the inclined end of the fiber and the one or more of the ciliary body band or the scleral spur in response the image of one or more of a ciliary body band, a scleral spur, or a Schwalbe's line of the eye and the rotational angle.

Clause 37. The apparatus of any one of the preceding clauses, wherein the processor is configured with instructions to determine a rotational orientation angle between the elongate insertion axis or the inclined distal end of the optical fiber and one or more of the rows or columns of the detector array.

Clause 38. The apparatus of claim any one of the preceding clauses, wherein the optical fiber comprises a core and a cladding, the cladding comprising a diameter within a range from about 100 micrometers (um) to about 300 um and optionally within a range from about 150 um to about 250 um.

Clause 39. The apparatus of claim any one of the preceding clauses, wherein the optical fiber comprises a plurality of optical fibers, each comprising an inclined distal end, the distal ends aligned to engage tissue of the eye with similar angles to within about 10 degrees.

Clause 40. The apparatus of any one of the preceding clauses, further comprising an operating microscope to view an anterior portion of the eye from outside the eye, the operating microscope comprising a plurality of oculars for a user to view an optical image the anterior portion of the eye formed with a plurality of lenses, the operating microscope comprising a heads-up display to show the image from the camera when the camera has been place inside the eye in order for the user to view the anterior image of the eye through the operating and view the image of the eye from the camera in real time, and optionally wherein the image from the camera comprises one or more markers showing the location of the one or more of the ciliary body band, the scleral spur or Schlemm's canal.

Clause 41. The apparatus of any one of the preceding clauses, further comprising an operating microscope to view an anterior portion of the eye from outside the eye, the operating microscope comprising a plurality of oculars for a user to view an optical image the anterior portion of the eye formed with a plurality of lenses, the operating microscope comprising a heads-up display to show the image from the camera when the camera has been place inside the eye in order for the user to view the anterior image of the eye through the operating and view the image of the eye from the camera in real time, and optionally wherein the image from the camera on the heads-up display comprises an image of the implant.

Clause 42. The apparatus of claim any one of the preceding clauses, wherein the camera comprises an optical axis, the optical axis of the camera aligned with a tissue engaging structure on the probe to within about 5 degrees, wherein the tissue engaging structure comprises one or more of a distal end of a probe shaped to contact the trabecular meshwork, an inclined distal end of a probe shaped to contact the trabecular meshwork, a stylet sized and shaped to penetrate the trabecular meshwork, a tip of the stylet, an implant on the distal end of the probe, or a sharp end of an implant on the distal end of the probe.

Clause 43. An apparatus of any one of the preceding clauses, wherein an imaging system (e.g., camera, scope, probe, fiber, etc.) is configured to display an image of the anatomy of an interior of an eye and of a probe located within the interior of the eye, and is further configured to provide updated images concurrent with movement of the probe.

As detailed above, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. For example, one or more of the devices recited herein may receive image data of a sample to be transformed, transform the image data, output a result of the transformation to determine a process, use the result of the transformation to perform the process, and store the result of the transformation to produce an output image of the sample. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

A processor as described herein can be configured to perform one or more steps of any method described herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

Although reference is made to an imaging probe comprising a plurality of optical fibers, in some embodiments the imaging probe comprises a single optical fiber. For example, the imaging probe may comprise a single optical fiber configured to deflect with a scan pattern to image light from the eye. The optical fiber can be configured to transmit light to a plurality of locations to generate the internal image of the eye, or configured to deflect and receive light from a plurality of locations.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. An apparatus to treat an eye, comprising:
   a probe comprising an endoscope and a treatment element, the treatment element comprising a treatment optical fiber;
   a treatment optical fiber housing enclosing the treatment optical fiber;
   a camera housing enclosing a camera with a fixed rotational orientation;
   a fastener to couple the treatment optical fiber housing to the camera housing with the fixed rotational orientation, wherein one or more of the fastener, the treatment optical fiber housing, or the camera housing comprises an engagement structure to couple to the fastener, the fastener configured to allow the probe to slide in relation to the treatment optical fiber housing while the orientation of the of the probe to the treatment optical fiber housing remains fixed; and
   a processor coupled to the probe, the processor configured to display a position of a Schlemm's canal and, an angular orientation of the treatment element relative to the Schlemm's canal, the display position and angular orientation updating concurrent with movement of the probe.

2. The apparatus of claim 1, wherein the processor is configured with instructions to determine a location of Schlemm's canal in response to an image of one or more of a ciliary body band or a scleral spur or a Schwalbe's line of the eye.

3. The apparatus of claim 1, wherein the processor is configured with instructions to determine a location of a trabecular meshwork in response to an image of one or more of a ciliary body band, a scleral spur, or a Schwalbe's line of the eye.

4. The apparatus of claim 1, wherein the processor is configured with instructions to determine compression of a trabecular meshwork in response to an image of one or more of a ciliary body band, a scleral spur, a Schwalbe's line, or a change in position of the probe relative to the trabecular meshwork or the Schlemm's canal.

5. The apparatus of claim 1, wherein the treatment optical fiber is coupled to a laser, the treatment optical fiber comprising an inclined distal end and a proximal end, the inclined distal end coupled to an array detector with the fixed rotational orientation.

6. The apparatus of claim 5, wherein the processor is configured to display the angular orientation of the inclined distal end of the treatment optical fiber in relation to the Schlemm's canal on a display.

7. The apparatus of claim 5, wherein the angular orientation of the inclined distal end corresponds to a rotation angle around an elongate axis of the probe.

8. The apparatus of claim 1, wherein the fastener comprises one or more of a clip or an aperture to engage one or more of the treatment optical fiber housing or the camera housing.

9. The apparatus of claim 1, wherein the engagement structure comprises one or more elongate engagement structures to maintain the fixed rotational orientation while the probe slides in relation to the treatment optical fiber housing.

10. The apparatus of claim 1, wherein the fastener is configured to fix a distance between a distal end of the probe and an array detector.

11. The apparatus of claim 1, further comprising a handpiece coupled to the probe and wherein an array detector is positioned within the handpiece.

12. The apparatus of claim 1, wherein the probe housing has a maximum distance across within a range from about 0.8 to 1.2 mm, the treatment optical fiber housing comprises a maximum distance across within a range from about 300 um to about 600 um, the fastener sized and shaped to extend around at least a portion of the probe housing and a portion of the treatment optical fiber housing, wherein the fastener comprises a first distance transverse to the probe housing and the treatment optical fiber housing, a second distance transverse to the probe housing and the treatment optical fiber housing, and a third distance along an elongate axis of the probe housing and the treatment optical fiber housing, the second distance less than the first distance, the third distance greater than the second distance and the first distance.

13. The apparatus of claim 12, wherein the first distance is within a range from 1.0 mm to 2 mm, the second distance within a range from 0.8 to 1.5 mm, the third distance within a range from 2 mm to 20 mm.

* * * * *